United States Patent
Petasis et al.

(10) Patent No.: US 9,732,074 B2
(45) Date of Patent: Aug. 15, 2017

(54) METHODS, COMPOUNDS, AND COMPOSITIONS FOR THE TREATMENT OF ANGIOTENSIN-RELATED DISEASES

(71) Applicants: UNIVERSITY OF SOUTHERN CALIFORNIA, Los Angeles, CA (US); Nicos A. Petasis, Hacienda Heights, CA (US); Kathleen E. Rodgers, Long Beach, CA (US); Stan G. Louie, Fullerton, CA (US); Gere S. DiZerega, San Luis Obispo, CA (US); Kevin J. Gaffney, Los Angeles, CA (US)

(72) Inventors: Nicos A. Petasis, Hacienda Heights, CA (US); Kathleen E. Rodgers, Long Beach, CA (US); Stan G. Louie, Fullerton, CA (US); Gere S. DiZerega, San Luis Obispo, CA (US); Kevin J. Gaffney, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/773,041

(22) PCT Filed: Mar. 15, 2014

(86) PCT No.: PCT/US2014/030071
§ 371 (c)(1),
(2) Date: Sep. 4, 2015

(87) PCT Pub. No.: WO2014/145331
PCT Pub. Date: Sep. 18, 2014

(65) Prior Publication Data
US 2016/0016946 A1    Jan. 21, 2016

Related U.S. Application Data

(60) Provisional application No. 61/809,290, filed on Apr. 5, 2013, provisional application No. 61/802,259, filed on Mar. 15, 2013.

(51) Int. Cl.
| | | |
|---|---|---|
| *C07D 213/52* | (2006.01) | |
| *C07D 401/06* | (2006.01) | |
| *C07D 417/06* | (2006.01) | |
| *C07D 213/36* | (2006.01) | |

(52) U.S. Cl.
CPC ......... *C07D 417/06* (2013.01); *C07D 213/36* (2013.01); *C07D 213/52* (2013.01); *C07D 401/06* (2013.01)

(58) Field of Classification Search
None
See application file for complete search history.

(56) References Cited

U.S. PATENT DOCUMENTS

| | | |
|---|---|---|
| 5,395,844 A | 3/1995 | Duncia et al. |
| 5,834,432 A | 11/1998 | diZerega et al. |
| 5,955,430 A | 9/1999 | diZerega et al. |
| 6,096,709 A | 8/2000 | diZerega et al. |
| 6,110,895 A | 8/2000 | diZerega et al. |
| 6,165,978 A | 12/2000 | diZerega et al. |
| 6,177,407 B1 | 1/2001 | diZerega et al. |
| 6,239,109 B1 | 5/2001 | diZerega et al. |
| 6,248,587 B1 | 6/2001 | Rodgers et al. |
| 6,258,778 B1 | 7/2001 | diZerega et al. |
| 6,335,195 B1 | 1/2002 | Rodgers et al. |
| 6,444,646 B1 | 9/2002 | Rogers et al. |
| 6,455,500 B1 | 9/2002 | diZerega et al. |
| 6,455,501 B1 | 9/2002 | Rodgers et al. |
| 6,475,988 B1 | 11/2002 | Rodgers et al. |
| 6,482,800 B1 | 11/2002 | Rodgers et al. |
| 6,498,138 B1 | 12/2002 | Rodgers et al. |
| 6,730,775 B1 | 5/2004 | diZerega et al. |
| 6,747,008 B1 | 6/2004 | diZerega et al. |
| 6,762,167 B1 | 7/2004 | Rodgers et al. |
| 6,821,953 B1 | 11/2004 | diZerega et al. |
| 6,916,783 B2 | 7/2005 | Rodgers et al. |
| 7,022,675 B2 | 4/2006 | diZerega et al. |
| 7,118,748 B1 | 10/2006 | Rodgers et al. |
| 7,122,523 B2 | 10/2006 | Rodgers et al. |
| 7,173,011 B2 | 2/2007 | Rodgers et al. |
| 7,176,183 B2 | 2/2007 | diZerega et al. |
| 7,288,522 B1 | 10/2007 | diZerega et al. |
| 7,338,938 B2 | 3/2008 | Rodgers et al. |

(Continued)

FOREIGN PATENT DOCUMENTS

| | | |
|---|---|---|
| WO | 99/42123 A1 | 8/1999 |
| WO | 0001389 A1 | 1/2000 |

(Continued)

OTHER PUBLICATIONS

Supplementary European Search Report for European Application No. EP14763703 performed Dec. 7, 2016.

Quan, Mimi L. "Balanced angiotensin II receptor antagonists. I. The effects of biphenyl "ortho"-substitution on AT1/AT2 affinities" Bioorganic & Medicinal Chemistry Letters, 1994, vol. 4, Issue 16, pp. 2011-2016.

Albrecht, D. (2007). Angiotensin-(1-7)-induced plasticity changes in the lateral amygdala are mediated by COX-2 and NO. Learning & Memory, 14(3), 177-184.

Balingit PP, Armstrong DG, Reyzelman AM, Bolton L, Verco SJ, Rodgers KE, Nigh KA, diZerega GS. NorLeu3-A(1-7) stimulation of diabetic foot ulcer healing: results of a randomized, parallel-group, double-blind, placebo-controlled phase 2 clinical trial. Wound Repair Regen. Jul.-Aug. 2012;20(4):482-90. doi: 10.1111.

(Continued)

*Primary Examiner* — Theodore R West
(74) *Attorney, Agent, or Firm* — McDonnell Boehnen Hulbert & Berghoff LLP

(57) ABSTRACT

Disclosed are small molecule non-peptidic compounds, as well as methods and compositions for the treatment of angiotensin-related diseases and disorders, including cardiovascular diseases, metabolic diseases, gastrointestinal diseases, renal diseases, inflammatory/autoimmune diseases, neurological diseases, bone marrow diseases and cancer.

22 Claims, 7 Drawing Sheets

(56) References Cited

U.S. PATENT DOCUMENTS

| | | | |
|---|---|---|---|
| 7,744,927 B2 | 6/2010 | Rodgers et al. | |
| 7,745,411 B2 | 6/2010 | Rodgers et al. | |
| 7,776,828 B2 | 8/2010 | diZerega et al. | |
| 7,786,085 B2 | 8/2010 | diZerega et al. | |
| 8,158,659 B2* | 4/2012 | Allegretti | C07D 213/64 |
| | | | 435/7.1 |
| 8,207,233 B1 | 6/2012 | Rodgers et al. | |
| 8,207,234 B1 | 6/2012 | Rodgers et al. | |
| 8,536,231 B2 | 9/2013 | Rodgers et al. | |
| 9,272,013 B2 | 3/2016 | Rodgers et al. | |
| 2002/0147129 A1 | 10/2002 | Mendelsohn et al. | |
| 2003/0130196 A1 | 7/2003 | Rodgers | |
| 2005/0032851 A1 | 2/2005 | Talley et al. | |
| 2008/0318951 A1* | 12/2008 | Allegretti | C07D 235/08 |
| | | | 514/234.5 |
| 2010/0055146 A1 | 3/2010 | Haas et al. | |
| 2010/0197604 A1 | 8/2010 | Bevec et al. | |
| 2011/0009409 A1 | 1/2011 | Blair | |
| 2012/0329784 A1 | 12/2012 | Kallander et al. | |
| 2014/0205631 A1 | 7/2014 | Larsen et al. | |
| 2015/0147283 A1 | 5/2015 | Rodgers et al. | |
| 2016/0016946 A1 | 1/2016 | Petasis et al. | |
| 2016/0051622 A1 | 2/2016 | Rodgers et al. | |

FOREIGN PATENT DOCUMENTS

| | | |
|---|---|---|
| WO | 2011/011232 A1 | 1/2011 |
| WO | 2011/088027 A1 | 7/2011 |
| WO | 2011/120032 A1 | 9/2011 |
| WO | 2012/135597 A1 | 10/2012 |

OTHER PUBLICATIONS

Benter IF, Yousif MH, Anim JT, Cojocel C, Diz DI (2006) Angiotensin-(1-7) prevents development of severe hypertension and end-organ damage in spontaneously hypertensive rats treated with L-NAME. Am J Physiol Heart Circ Physiol 290(2):H684-H691.

Benter IF, Yousif MH, Cojocel C, AL-Maghrebi M, Diz DI (2007) Angiotensin-(1-7) prevents diabetes-induced cardiovascular dysfunction. Am J Physiol Heart Circ Physiol 292(1):H666-672.

Dias-Peixoto MF, Santos RAS, Gomes ERM,. Alves MNM, Almeida PWM, Greco L, Rosa M, Fauler B, Michael Bader, Alenina N, Guatimosim S. Molecular Mechanisms Involved in the Angiotensin-(1-7)/Mas Signaling Pathway in Cardiomyocytes. Hypertension. 2008; 52: 542-548.

Dhaunsi, G. S., Yousif, M. H., Akhtar, S., Chappell, M. C., Diz, D. I., & Benter, I. F. (2010). Angiotensin-(1-7) prevents liabetes-induced attenuation in PPAR-$\gamma$ and catalase activities. European journal of pharmacology, 638(1), 108-114.

Ebermann L, Spillmann F, Sidiropoulos M, Escher F, Heringer-Walther S, Schultheiss HP, Tschope C, Walther T (2008) The angiotensin-(1-7) receptor agonist AVE0991 is cardioprotective in diabetic rats. Eur J Pharmacol 590 (1-3):276-280.

Kosugi, T., Heinig, M., Nakayama, T., Matsuo, S., & Nakagawa, T. (2010). eNOS knockout mice with advanced diabetic nephropathy have less benefit from renin-angiotensin blockade than from aldosterone receptor antagonists. The American journal of pathology, 176(2), 619-629.

Langeveld, B. , A. J. Roks , and R. A. Tio . et al. Rat abdominal aorta stenting: a new and reliable small animal model for in-stent restenosis. J Vasc Res 2004.41:377-386.

Loot AE, Roks AJ, Henning RH, Tio RA, Suurmeijer AJ, Boomsma F, van Gilst WH (2002) Angiotensin-(1-7) attenuates the development of heart failure after myocardial in rats Circulation 105(13):1548-1550.

Marcus, Y., et al., Angiotensin 1-7 as Means to Prevent the Metabolic Syndrome: Lessons From the Fructose-Fed Rat Model. Diabetes, 2013.62(4): p. 1121-1130.

Pham H, Schwartz BM, Delmore JE, Reed E, Cruickshank S, Drummond L, Rodgers KE, Peterson KJ, Dizerega GS. Pharmacodynamic stimulation of thrombogenesis by angiotensin (1-7) in recurrent ovarian cancer patients receiving gemcitabine and platinum-based chemotherapy. Cancer Chemother Pharmacol. Apr. 2013;71(4):965-72.

Ribeiro-Oliveira A, Nogueira AI, Pereira RM, Boas WW, Dos Santos RA, Simoes e Silva AC (2008) The renin-angiotensin system and diabetes: an update. Vasc Health Risk Manag 4(4):787-803.

Rodgers KE, Oliver J, diZerega GS. Phase I/II dose escalation study of angiotensin 1-7 [A(1-7)] administered before and after chemotherapy in patients with newly diagnosed breast cancer.Cancer Chemother Pharmacol. May 2006;57 (5):559-68.

Rodgers KE, Xiang S, diZerega GS. Accelerated recovery from irradiation injury by angiotensin peptides. Cancer Chemother Pharmacol. May 2002;49(5):403-11.

Santos RA, Simoes e Silva AC, Marie C, Silva DM, Machado RP, de Buhr I, Heringer-Walther S, Pinheiro SV, Lopes MT Bader M, Mendes EP, Lemos VS, Campagnole-Santos MJ, Schultheiss HP, Speth R, Walther T (2003) Angiotensin-(1-7) is an endogenous ligand for the G protein-coupled receptor Mas Proc Nati Acad Sci USA 100 (14):8258-8263.

Santos, R. A. S., and Ferreira, A. J. (2006). Pharmacological Effects of AVE 0991, a Nonpeptide Angiotensin-(1-7) Receptor Agonist. Cardiovascular Drug Reviews, 24(3-4), 239-246.

Santos, S. H. S., Braga, J. F., Mario, É. G., Pôrto, L. C. J., da Glória Rodrigues-Machado, M., Murari, A., & Santos, R. A. S. (2010). Improved lipid and glucose metabolism in transgenic rats with increased circulating angiotensin-(1-7). Arteriosclerosis, thrombosis, and vascular biology, 30(5), 953-961.

Singh K, Singh T, Sharma PL (2011) Beneficial effects of angiotensin-(1-7) in diabetic rats with cardiomyopathy. Ther Adv Cardiovasc Dis 5(3):159-167.

Steckelings, U. M., Larhed, M., Hallberg, A., Widdop, R. E., Jones, E. S., Wallinder, C., Namsolleck, P., Dahlö, B., and Unger, T. (2011). Non-peptide AT2-receptor agonists. Curr Opin Pharmacol, 11(2), 187-192.

Zhang, T., Li, Z., Dang, H., Chen, R., Liaw, C., Tran, T.-A., Boatman, P. D., Connolly, D. T., and Adams, J. W. (2012). Inhibition of Mas G-protein signaling improves coronary blood flow, reduces myocardial infarct size, and provides long-term cardioprotection. American Journal of Physiology—Heart and Circulatory Physiology, 302(1), H299-H311.

International Search Report for PCT/US2014/030071, mailed Aug. 5, 2014.

* cited by examiner

Angiotensin I      Asp-Arg-Val-Tyr-Ile-His-Pro-Phe-His-Leu

Angiotensin (1-9)  Asp-Arg-Val-Tyr-Ile-His-Pro-Phe-His

Angiotensin II     Asp-Arg-Val-Tyr-Ile-His-Pro-Phe

Angiotensin (1-7)  Asp-Arg-Val-Tyr-Ile-His-Pro

Angiotensin IV           Val-Tyr-Ile-His-Pro-Phe

Figure 2
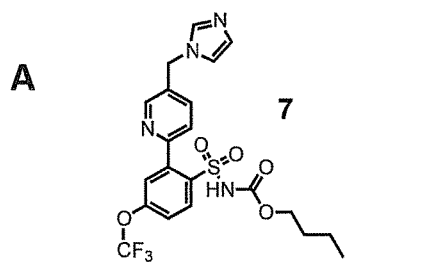
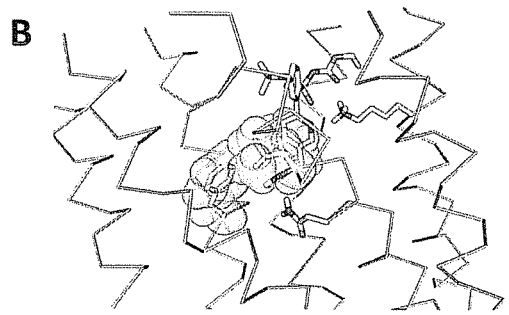
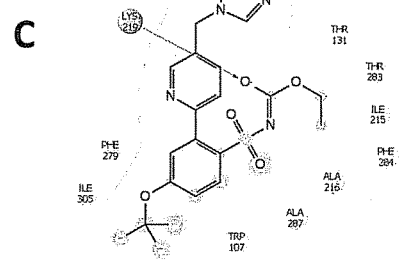
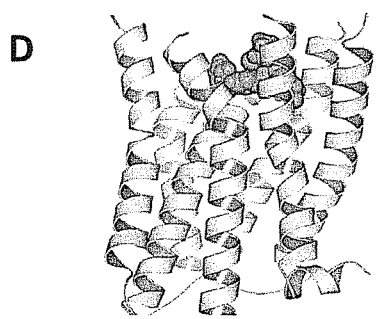
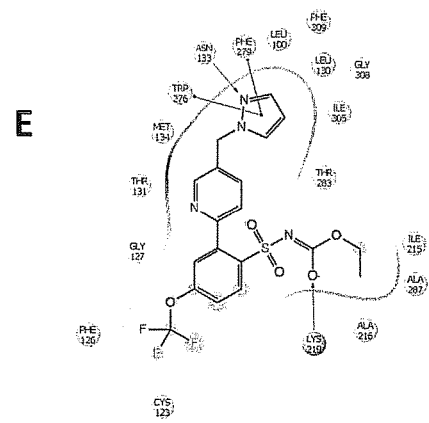
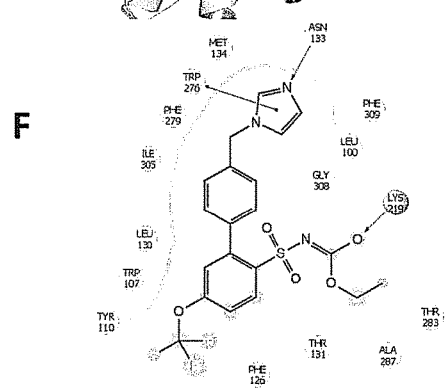
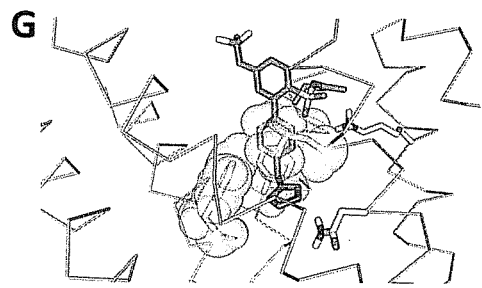
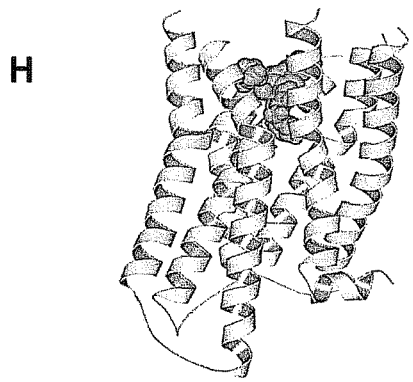

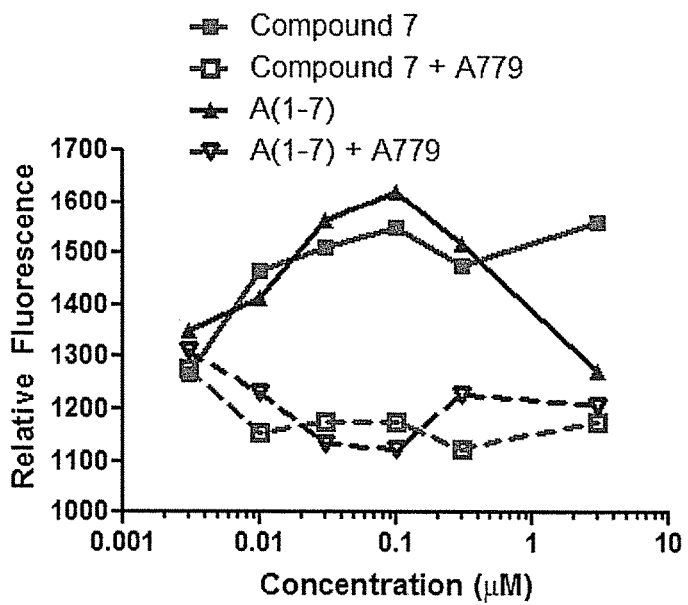
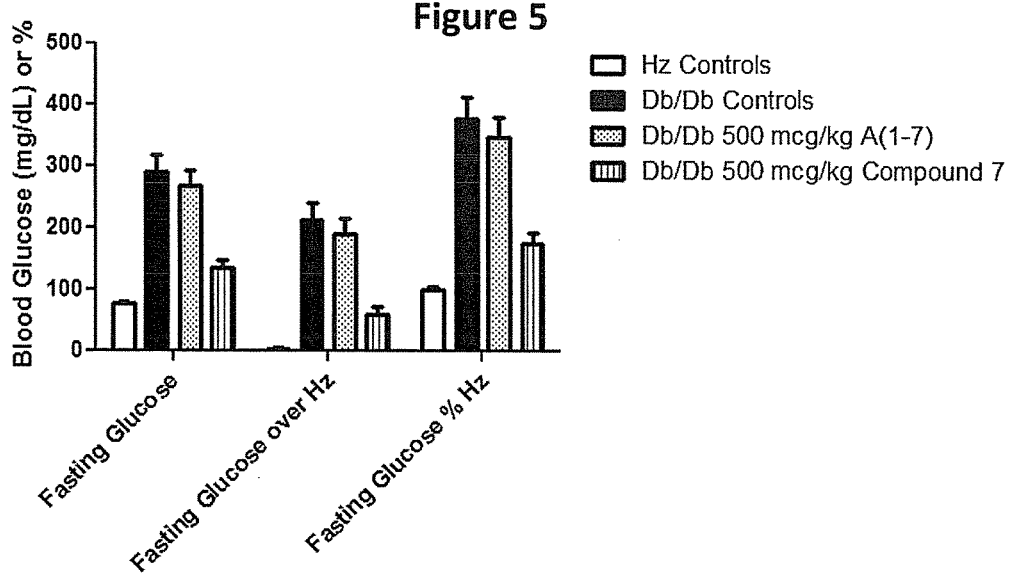

Figure 6
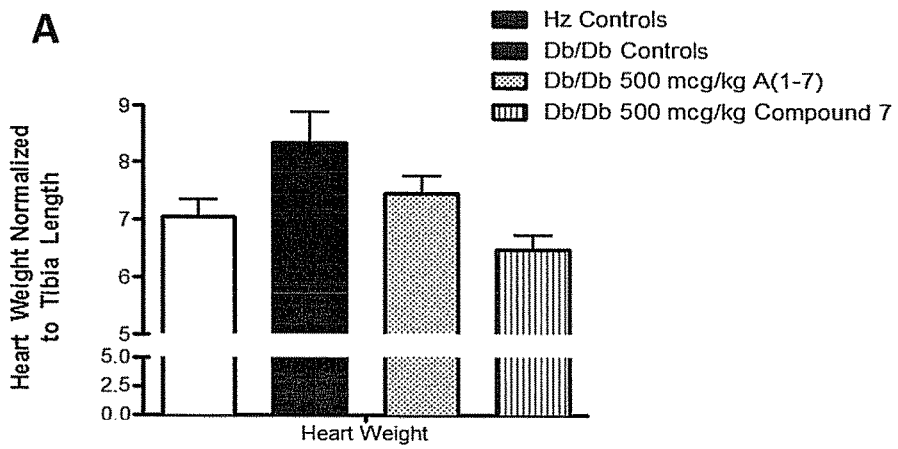
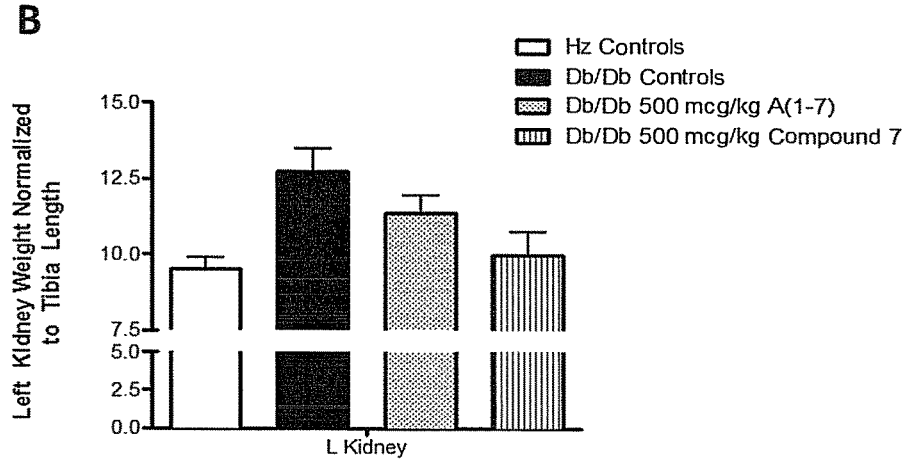
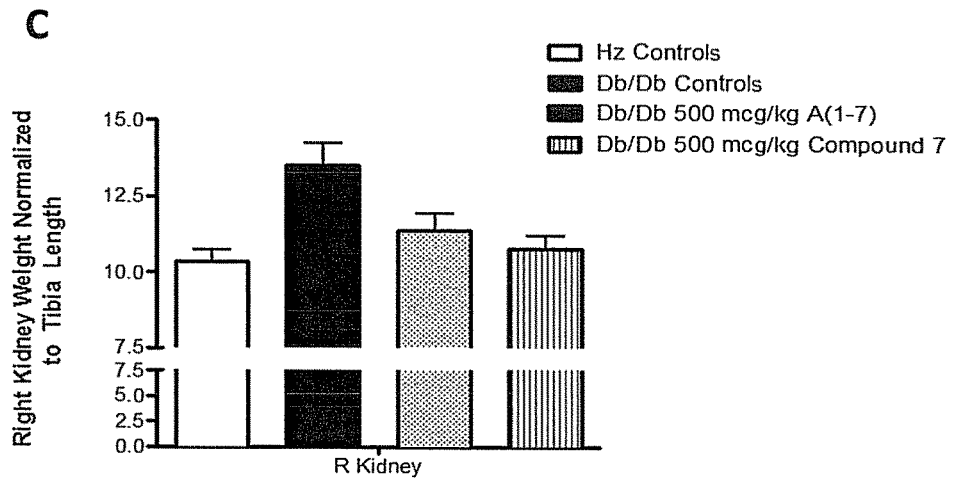

Compound 7 Treatment      Saline Treatment

METHODS, COMPOUNDS, AND COMPOSITIONS FOR THE TREATMENT OF ANGIOTENSIN-RELATED DISEASES

RELATED APPLICATIONS

This application is a U.S. national phase application of International Patent Application No. PCT/US2014/030071, filed on Mar. 15, 2014, which claims priority to U.S. Provisional Application Ser. No. 61/809,290 filed Apr. 5, 2013 and U.S. Provisional Application Ser. No. 61/802,259 filed Mar. 15, 2013, the disclosures of which are hereby incorporated by reference in their entireties.

FIELD OF THE INVENTION

This invention relates to novel heteroaryl non-peptidic compounds that mimic the heptapeptide angiotensin (1-7) [Ang(1-7)] and act as agonists of the Mas receptor, especially in a selective manner. The invention further relates to methods of using such compounds as therapeutic agents, in particular for the treatment of angiotensin-related diseases or disorders, to pharmaceutical compositions containing such compounds, and to synthetic routes for the preparation of such compounds.

BACKGROUND OF THE INVENTION

A wide range of physiological and pathophysiological conditions are related to the renin-angiotensin system (RAS), which is an important regulator of arterial blood pressure and involves the formation and actions of several angiotensin peptides (FIG. 1). The major angiotensin peptides include the decapeptide angiotensin I (Asp-Arg-Val-Tyr-Ile-His-Pro-Phe-His-Leu), the octapeptide angiotensin II (Asp-Arg-Val-Tyr-Ile-His-Pro-Phe), the heptapeptide angiotensin (1-7) (Asp-Arg-Val-Tyr-Ile-His-Pro) and the hexapeptide angiotensin IV (Val-Tyr-Ile-His-Pro-Phe).

The angiotensin peptides and the related enzymes and receptors play key roles in the cardiovascular system, the renal system, the hematopoietic system, the hepatobiliary system, the pulmonary system, the gastrointestinal system, the nervous system, and in many other critical physiological and pathophysiological pathways, in part, through stimulation of stem cell activity (FIG. 1). Renin acts on angiotensinogen to form angiotensin I (AngI), which is cleaved by angiotensin converting enzyme (ACE) to form angiotensin II (AngII), and by neutral endopeptidases to form Ang(1-7), which is also produced from AngII via cleavage by ACE2.

The three G-protein coupled receptors (GPCR) that mediate many of the actions of the angiotensin peptides are the AngII type 1 receptor (AT1R), the AngII type 2 receptor (AT2R), and the Mas receptor (Mas) known as the native receptor for Ang(1-7). The activation or deactivation of these receptors play major roles in numerous tissues, including the heart, blood vessels, liver, kidney and the brain. The development of selective antagonists for AT1R provided multiple important therapeutics for heart disease and other conditions. More recently, the elucidation of the beneficial actions of the AT2R led to selective agonists for AT2R as potential therapeutics.

This invention discloses a new class of small molecule mimetics of Ang(1-7) that are able to bind and activate the Mas receptor, and can serve as potential therapeutics for a wide range of angiotensin-related diseases. Ang(1-7) acts as an endogenous agonist of the Mas receptor, and was shown to have a number of important beneficial actions.

Ang(1-7) was shown to modulate pathways impacted by obesity and diabetes, and has been shown to exert beneficial effects in end organ damage in diabetes and hypertension (Benter et al., 2006; 2007; Singh et al., 2011). In a rat model of metabolic syndrome, elevated circulating levels of Ang (1-7) enhanced glucose tolerance, insulin sensitivity and decreased dyslipidemia (Santos et al., 2010; Marcus et al., 2012). Ang(1-7) further improves heart function in diabetic animals and after myocardial infarction and reverses diabetes-induced bone marrow suppression (Loot et al., 2002; Langeveld et al., 2008; Ebermann et al, 2008). In a Phase II clinical trial, a peptide analogue of Ang(1-7) was shown to reduce diabetic complication of non-healing foot ulcers (Balingat et al, 2012). Although this peptide may have potential use in the reduction of diabetes and insulin resistance, daily peptide injections may not be the optimal route of administration to ensure patient adherence in a chronic disease. Therefore, there remains a need for small molecule mimics of Ang(1-7) that can be effectively used to control diabetes with improved patient adherence.

Ang(1-7) and its peptide analogs are non-hypertensive regenerative factors in clinical trials for accelerating healing of hematopoietic and dermal injuries. A pharmaceutical formulation of Ang(1-7) was shown to be safe for clinical use, and was found to stimulate bone marrow and hematopoietic recovery (Rodgers et al, 2002, 2006 and Pham et al 2013). Ang(1-7) was shown to be active in several models of tissue regeneration. The actions of Ang (1-7) are hypothesized to occur through production of arachidonic acid metabolites, nitric oxide (NO), or bradykinin (BK) metabolites (Albrect 2007; Ribeirio-Olivera et al., 2008; Dias-Peixoto et al., 2008). NO is involved in protection from organ failure in diabetes and in the actions of modulators of the RAS in improved outcomes in diabetics (Kosugi et al., 2010). Ang(1-7) may also reduce end organ damage in diabetes through stimulation of PPARγ, the pathway stimulated by several therapeutics used to reduce insulin resistance in diabetes (Dhaunsi et al., 2010).

The native receptor for Ang(1-7) is the GPCR Mas, where the genetic deletion of Mas abolished Ang(1-7) binding. Accordingly, Ang(1-7) was able to bind to Mas-transfected cells and elicited arachidonic acid release. In addition, Mas KO mice do not have an anti-naturetic and water volume changes and Ang(1-7) binding in the kidney. Furthermore, Mas-deficient aortas lost their Ang(1-7)-induced relaxation response (Santos et al., 2003). The benefits of Ang(1-7) to accelerate recovery of myelosuppression and reduce chronic inflammation in diabetics are mediated through Mas.

Despite some progress and extensive efforts there is still a need for new therapeutics that might be effective in preventing diabetes, reducing diabetic complications, and treating diabetes-related conditions. The current treatment for diabetes includes the use of antidiabetic agents such as insulin, biguianides, thiazolidinediones, non-sulfonylurea secretagogues, and peptide analogs. Current treatment targets reduction of circulating glucose through supplementing insulin secretion or increase cellular sensitivity to insulin activation. Despite managing circulating glucose, the co-morbidity associated with diabetes continues, albeit at a slower progression. This includes development cardiovascular disorders such as atherosclerosis, hypertension, congestive heart failure, and cerebral ischemia. In ability to control diabetes have also been linked to other organ dysfunction including renal dysfunction, diabetic retinopathy, and neurological dysfunction. These co-morbid conditions may be a consequence of uncontrolled chronic inflammation that may be promoted by uncontrolled glucotoxicity or insulin-resistance.

Despite extensive efforts that led to the successful design and development of antagonists for the AngII receptor 1 (AT1R), known as angiotensin receptor blockers (ARBs), similar studies to identify agonists of AT2R and Mas receptors have been limited. A few notable examples are the AT2R agonist compound 21 and related compounds (Steckeling et al., 2011), the Mas agonist AVE-0991 (Santos et al., 2006), and certain Mas modulator derivatives (Zhang et al., 2012).

The discovery of effective mimetics of Ang(1-7) that activate the Mas receptor in a potent and selective manner has remained a challenge. Molecules of this type are of great interest, and are expected to find use for the treatment of several major diseases for which there is an unmet medical need.

BRIEF SUMMARY OF THE INVENTION

One aspect of this invention provides heteroaryl non-peptidic compounds that mimic the heptapeptide angiotensin (1-7) and act as agonists of the Mas receptor, especially in a selective manner. The invention further provides methods of using such compounds as therapeutic agents, in particular for the treatment of angiotensin-related diseases or disorders and related conditions. The invention also provides pharmaceutical compositions containing such compounds, and synthetic routes for their preparation.

In one embodiment, compounds according the present invention have general formula 1 and includes salts thereof:

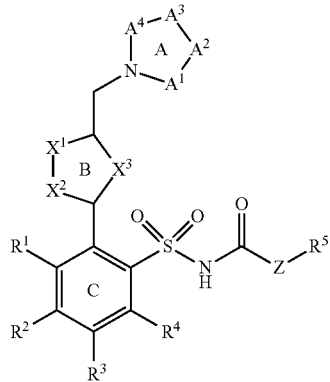

wherein:
ring A is a five-membered or six-membered heteroaryl or heterocyclyl ring containing either a combination of two non-adjacent nitrogen or oxygen atoms, or a combination of three or four nitrogen or oxygen atoms;
ring B is a five-membered or six-membered heteroaryl ring that contains at least one nitrogen atom;
ring C is an optionally substituted aryl ring;
$A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, or —[C($R^c$)($R^d$)]$_n$— with n being 1 or 2;
$X^1$—$X^2$ is ($R^6$)C—N, N—C($R^6$), N—N, N—O, O—N, N—S or S—N;
$X^3$ is ($R^7$)C=C($R^8$), O, S, or N($R^9$);
Z is O, NH or a bond to $R^5$;

$R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^a$ and $R^b$ can also join to form a ring of up to 6 atoms;
$R^c$ and $R^d$ are independently selected from a group consisting of hydrogen, alkyl, aryl, or heteroaryl, provided that $R^c$ and $R^d$ can also join to form a ring of up to 6 atoms;
$R^e$ is hydrogen, alkyl, aryl, heteroaryl, acyl, alkoxyacyl, aminoacyl, dialkylaminoacyl, or dialkylaminoacyl;
$R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, bromo, iodo, cyano, hydroxy, amino, alkylamino, alkoxy, aryloxy, alkoxyalkyl, or aryloxyalkyl;
$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;
$R^5$ is alkyl, aryl, heteroaryl, hydroxyalkyl, carboxyalkyl, alkoxyalkyl, or aryloxyalkyl; and
$R^9$ is hydrogen, alkyl, aryl, heteroaryl, acyl, alkoxyacyl, aminoacyl, dialkylaminoacyl, or dialkylaminoacyl.

In a second embodiment, the invention provides methods for the preparation of the provided compounds.

In a third embodiment, the invention provides pharmaceutical compositions comprising one or more provided compounds in a pharmaceutically acceptable carrier.

In a fourth embodiment, the invention provides compounds that act as non-peptidic mimetics of Ang(1-7) or as effective agonists of the Mas receptor.

In a fifth embodiment, the invention provides methods for the treatment of angiotensin-related diseases or disorders and related conditions.

In a sixth embodiment, the provided methods and compositions are employed in oral, parenteral, or topical administration comprising of a provided compound or a pharmaceutically acceptable salt, and a pharmaceutically acceptable carrier.

In particular, the invention provides methods and compositions for the treatment of angiotensin-related diseases or disorders and related conditions, upon oral, parenteral (e.g. subcutaneous, intrathecal, epidural, intravenous, intraocular) and topical administration.

BRIEF DESCRIPTION OF THE DRAWINGS

FIG. 2: Binding motifs of the provided compounds at a homology model of AT2R. (A) Chemical structure of exemplary compound 7. (B) Model of compound 7 docked into an AT2R homology model. For clarity, the models of this Figure show only an ethyl group in place of the butyl group of compound 7. (C) Contact residues at the binding site of compound 7 at AT2R. (D) Overall orientation of compound 7 in its binding site at AT2R. (E) Contact residues at the binding site of the pyrazole isomer of compound 7 at AT2R. (F) Contact residues at the binding site of a closely related compound to exemplary compound 7, where the pyridine ring is replaced with a benzene ring. (G) Model of the compound shown in (F) docked into an AT2R homology model. For clarity, the models of this Figure show only an ethyl group in place of the butyl group of compound 7. (H) Overall orientation of compound shown in (F) in its binding site at AT2R.

FIG. 4: Mas stably transfected CHO was compared Ang (1-7) with compound 7, revealing a concentration dependent increase in NO as measured by the level of fluorescence (A). Mas agonist activity was confirmed when co-administered with A779, an antagonist of Mas, blocked both Ang(1-7) and compound 7 back to baseline fluorescence.

FIG. 5: Fasting blood glucose (FBG) was evaluate in db/db animals treated for 14 days with vehicle, 500 µg/kg/day Ang(1-7) and compound 7. Compound 7 was able to reduce peripheral glucose >40% of levels found in vehicle or Ang(1-7) treated mice (A).

FIG. 6: Compound 7 can prevent organmegaly in db/db animals. These animals were treated with 14 days with vehicle, 500 µg/kg Ang(1-7), or 500 µg/kg/day compound 7. Compound 7 treated animals were able to prevent the development of cardiomegaly (A) and left kidney hypertrophy (B), where the difference between db/db controls was statistically significant (p<0.05). The right kidney trended to be similar to heterozygous control, and lower than db/db controls (C).

DETAILED DESCRIPTION OF THE INVENTION

A. Definitions

Figure 1:
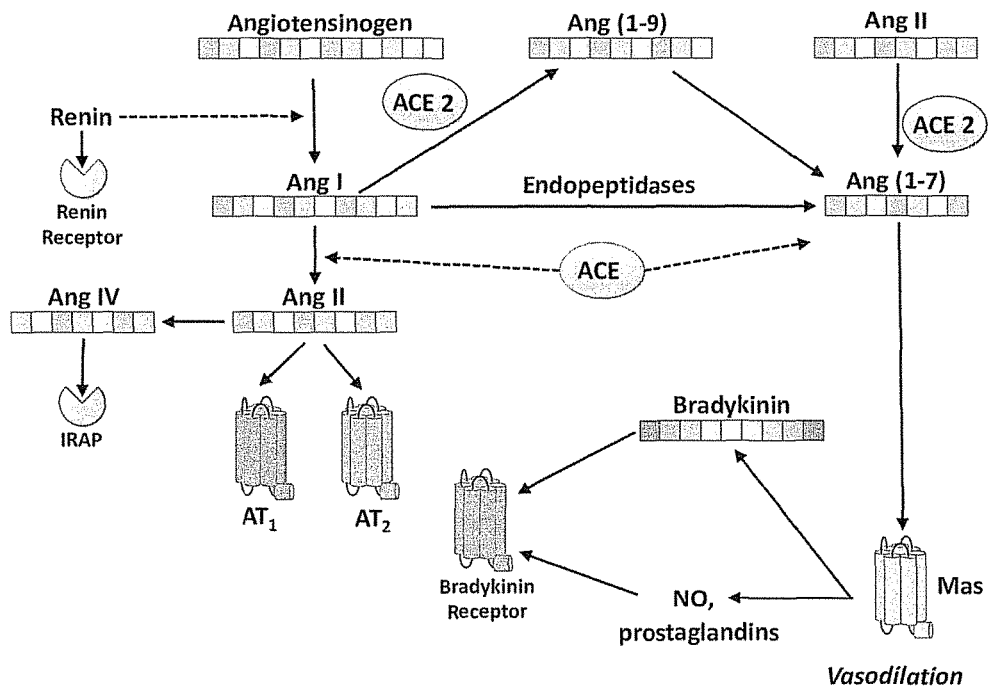
FIG. 1: The Renin-Angiotensin System (RAS). This figure lists the major RAS angiotensin peptides and highlights their biosynthesis and the target receptors that mediate these peptides' biological activities.

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section will control unless stated otherwise.

As used herein, the nomenclature alkyl, alkoxy, carbonyl, etc. is used as is generally understood by those of skill in the chemical art. As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multicyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals, which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

The term "alkenyl" refers to a branched or unbranched hydrocarbon having at least one carbon-carbon double bond.

The term "alkynyl" refers to a branched or unbranched hydrocarbon having at least one carbon-carbon triple bond.

The term "carboxy" refers to a —CO$_2$H group.

The term "hydroxy" refers to an —OH group.

The term "alkoxy" refers a group of the formula R—O— where R is an "alkyl" as defined herein.

The term "carbocycle" refers to a non-aromatic stable 3- to 8-membered carbon ring which may be saturated, mono-unsaturated or poly-unsaturated.

The term "amino" includes primary, secondary or tertiary amino groups.

The term "cyano" refers to the group —CN.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 4 to about 15 members where one or more, in one embodiment 1 to 4, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, triazolyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "aryloxy" refers to RO—, in which R is aryl, including lower aryl, such as phenyl.

As used herein, "acyl" refers to a —COR group, including for example alkylcarbonyl, cycloalkylcarbonyl, arylcarbonyl, or heteroarylcarbonyls, all of which may be optionally substituted.

As used herein "subject" is an animal, typically a mammal, including human, such as a patient.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, the term "treatment" means any manner in which one or more of the symptoms of a disease or disorder are ameliorated or otherwise beneficially altered. Treatment also encompasses any pharmaceutical use of the compositions herein, such as use for treating a disease as provided herein.

As used herein, amelioration of the symptoms of a particular disorder by administration of a particular compound or pharmaceutical composition refers to any lessening, whether permanent or temporary, lasting or transient that can be attributed to or associated with administration of the composition.

B. Compounds

As set forth above, this invention provides compounds, methods and compositions for the treatment of angiotensin-related diseases and disorders.

The provided compounds are able to act selectively at certain GPCR receptors.

This invention provides compounds of the general formula 1 and salts thereof:

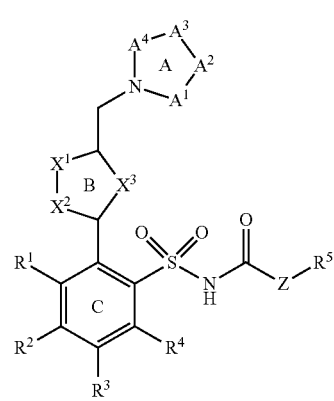

1 wherein:

ring A is a five-membered or six-membered heteroaryl or heterocyclyl ring containing either a combination of two non-adjacent nitrogen or oxygen atoms, or a combination of three or four nitrogen or oxygen atoms;

ring B is a five-membered or six-membered heteroaryl ring that contains at least one nitrogen atom;

ring C is an optionally substituted aryl ring;

$A^1$, $A^2$, $A^3$, M are independently selected from a group consisting of =N—, —C(=O)—, —C($R^a$)=, =C($R^b$)—, —C($R^c$)($R^d$)—N($R^e$)—, —C($R^c$)($R^d$)—O—, or —[C($R^c$)($R^d$)]$_n$— with n being 1 or 2;

$X^1$—$X^2$ is ($R^6$)C—N, N—C($R^6$), N—N, N—O, O—N, N—S or S—N;

$X^3$ is ($R^7$)C=C($R^8$), O, S, or N($R^9$);

Z is O, NH or a bond to $R^5$;

$R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^a$ and $R^b$ can also join to form a ring of up to 6 atoms;

$R^c$ and $R^d$ are independently selected from a group consisting of hydrogen, alkyl, aryl, or heteroaryl, provided that $R^c$ and $R^d$ can also join to form a ring of up to 6 atoms;

$R^e$ is hydrogen, alkyl, aryl, heteroaryl, acyl, alkoxyacyl, aminoacyl, dialkylaminoacyl, or dialkylaminoacyl;

$R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, bromo, iodo, cyano, hydroxy, amino, alkylamino, alkoxy, aryloxy, alkoxyalkyl, or aryloxyalkyl;

$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;

$R^5$ is alkyl, aryl, heteroaryl, hydroxyalkyl, carboxyalkyl, alkoxyalkyl, or aryloxyalkyl; and $R^9$ is hydrogen, alkyl, aryl, heteroaryl, acyl, alkoxyacyl, aminoacyl, dialkylaminoacyl, or dialkylaminoacyl.

In some preferred embodiments, $R^2$ is trifluoromethoxy.

In other preferred embodiments, Z is O, NH.

In exemplary embodiments, ring A includes but is not limited to a ring selected from a group consisting of:

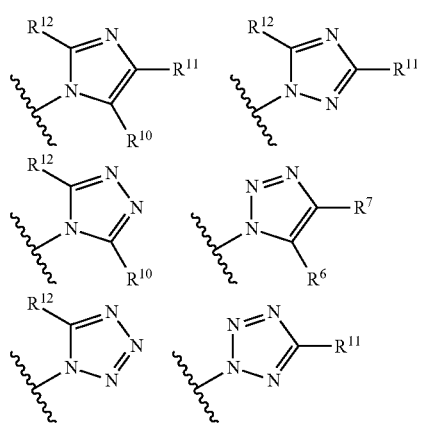

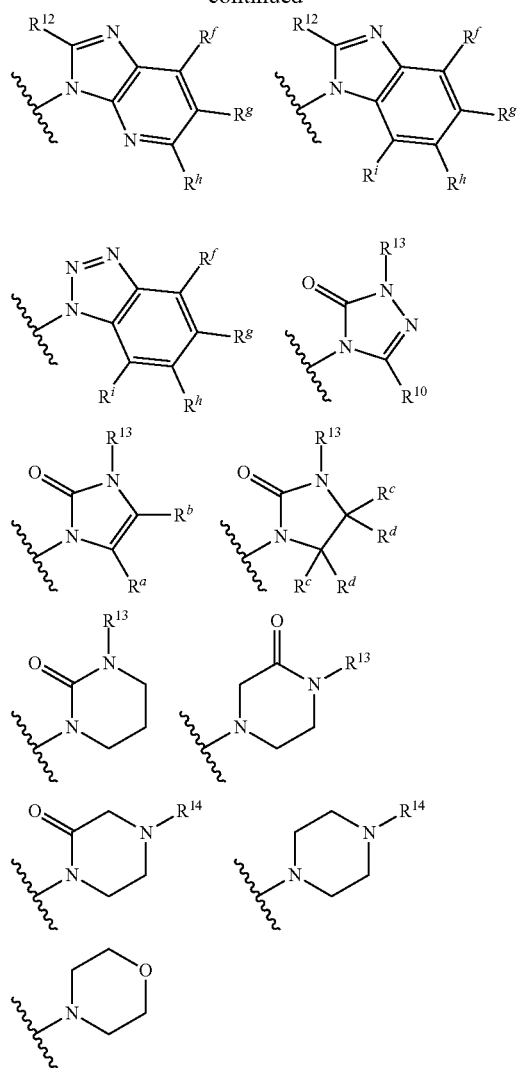

wherein:

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, or aryloxyalkyl.

In other exemplary embodiments, ring B includes but is not limited to a five- or six-membered heteroaryl ring selected from a group consisting of:

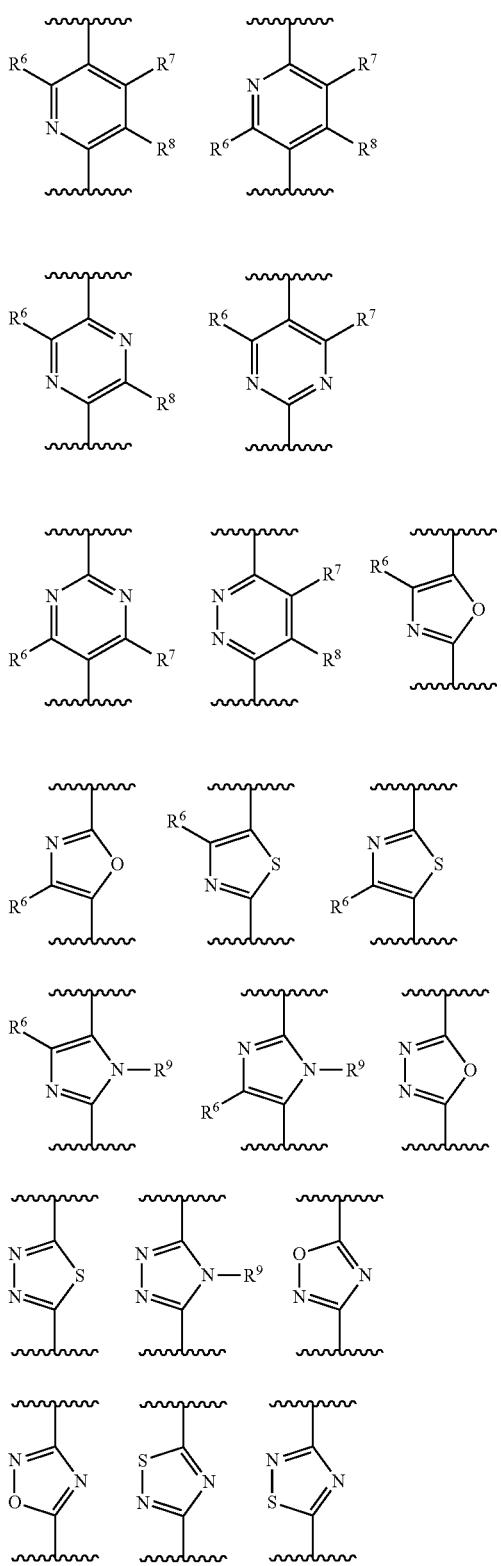
wherein groups $R^6$, $R^7$, $R^8$ and $R^9$ are defined as in general formula 1
In some exemplary embodiments, the provided compounds have the general formula selected from a group consisting of
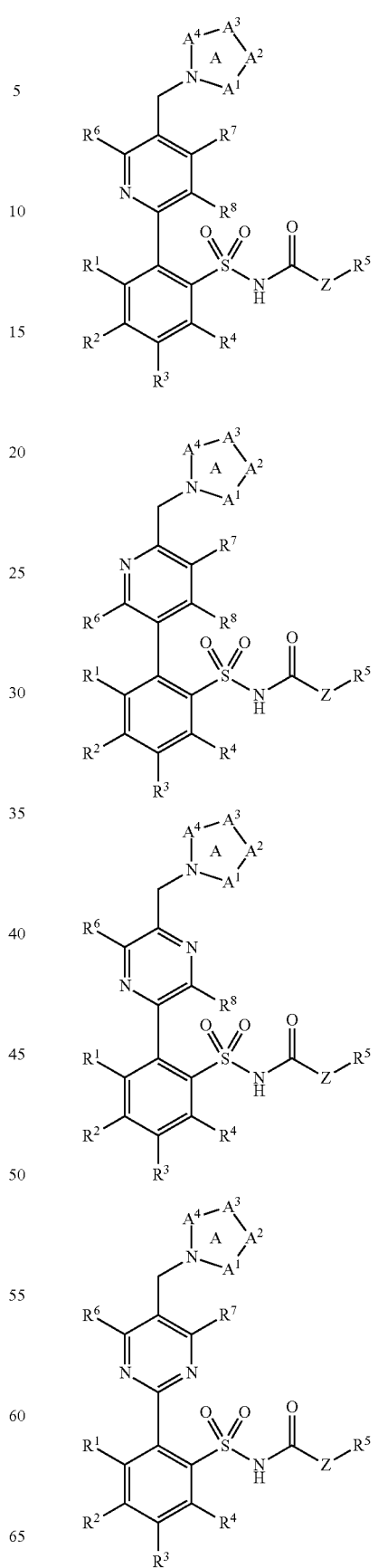

-continued
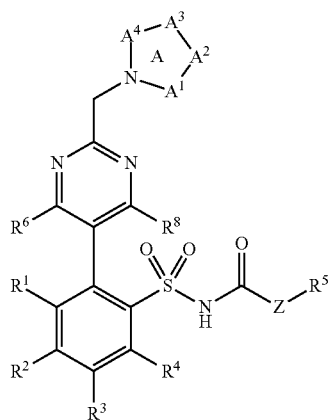
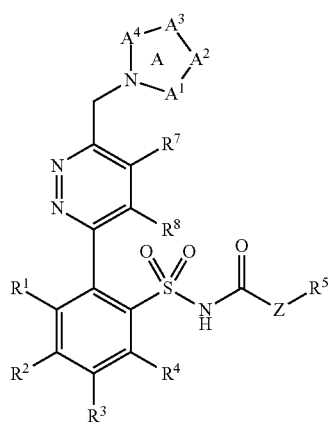
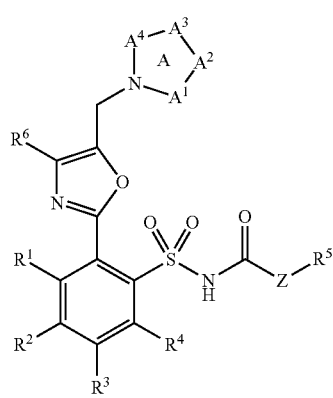
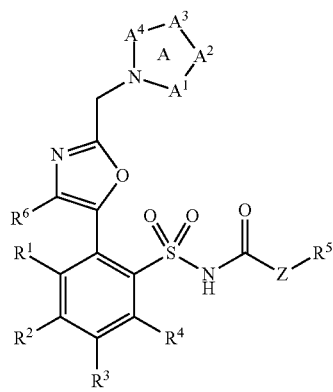
-continued
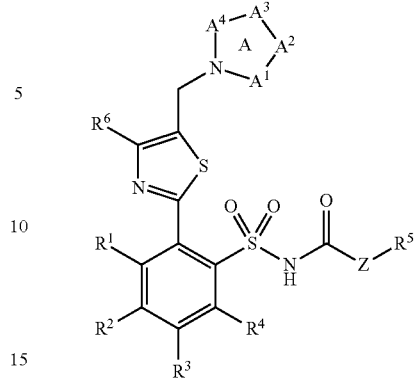
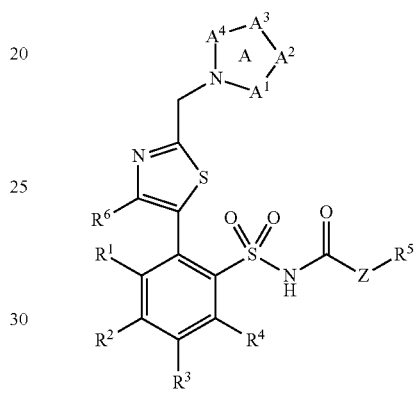
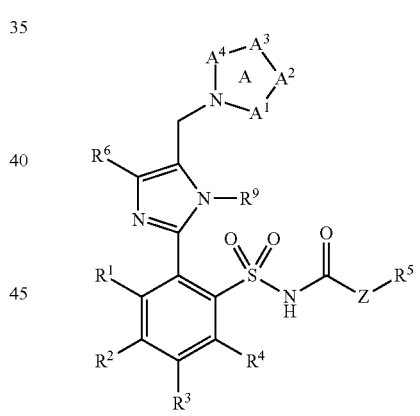
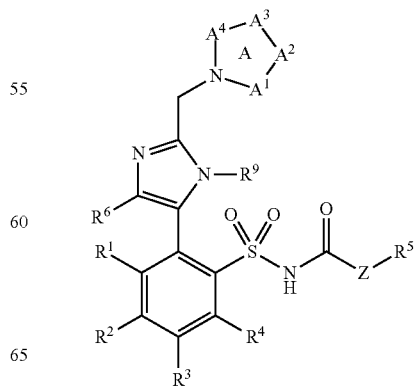

15
-continued
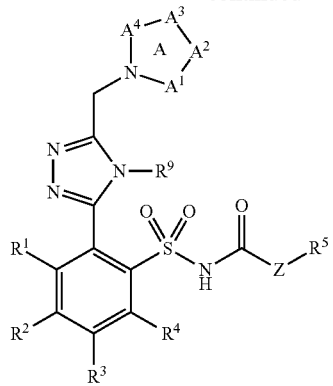
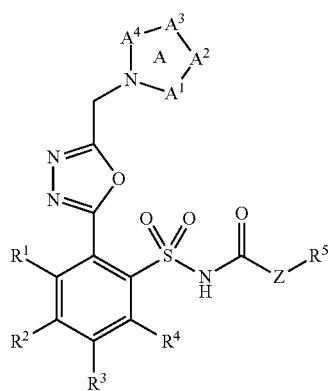
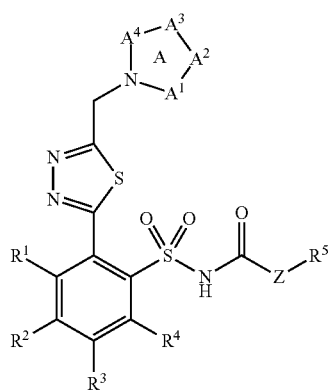
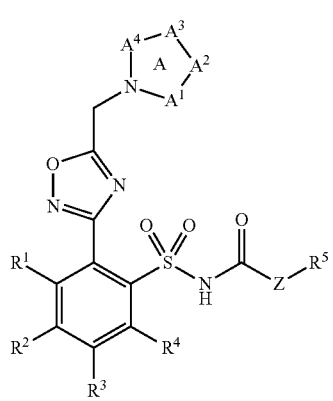
16
-continued
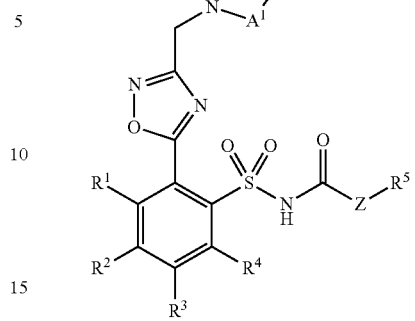
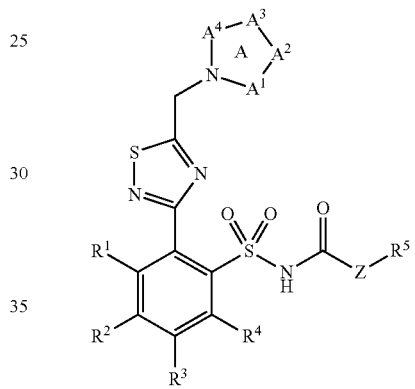
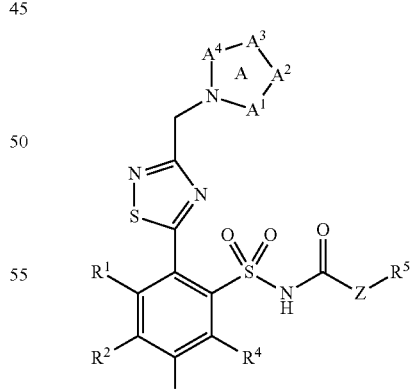
wherein groups $R^1$, $R^2$, $R^3$, $R^4$ $R^5$, $R^6$, $R^7$, $R^8$, $R^9$, $A^1$, $A^2$, $A^3$, $A^4$ and Z are defined as in general formula 1.
In other exemplary embodiments, the provided compounds have the general formula selected from a group consisting of:

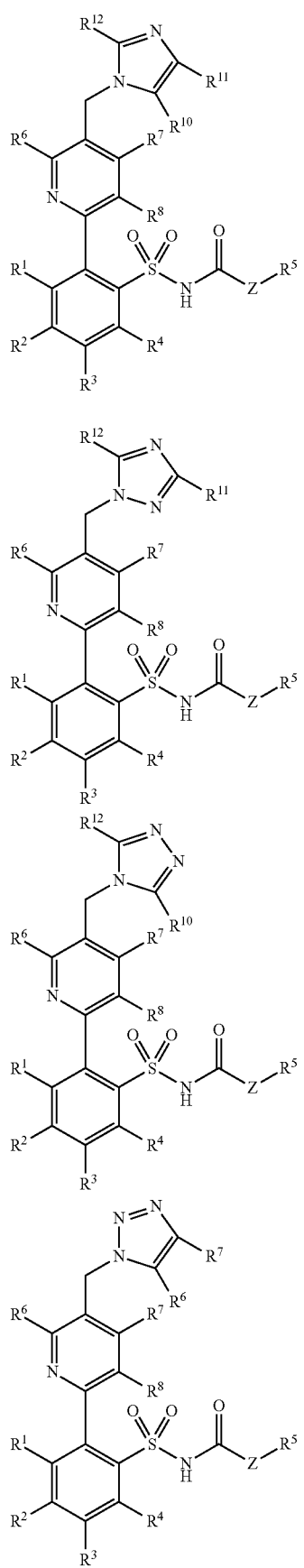
-continued
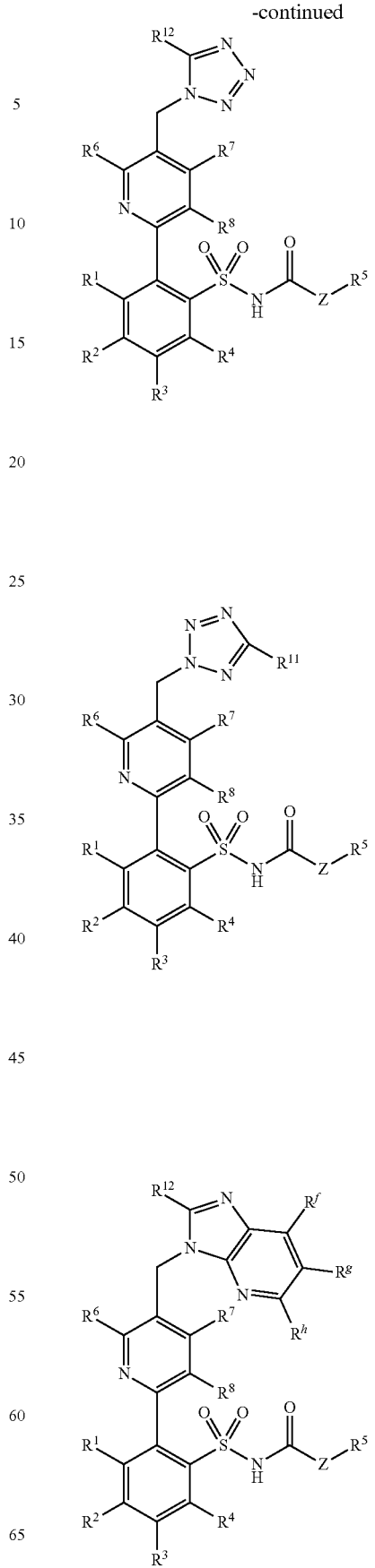

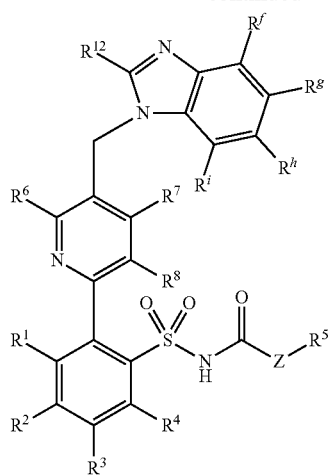
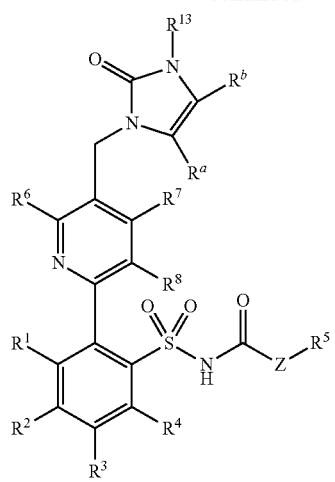
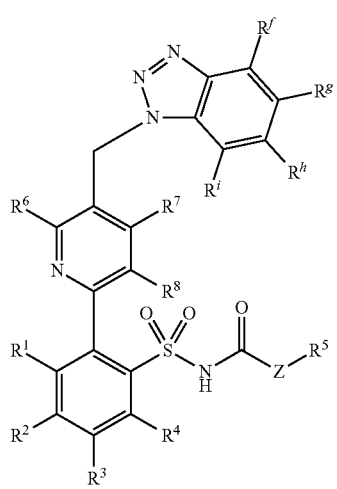
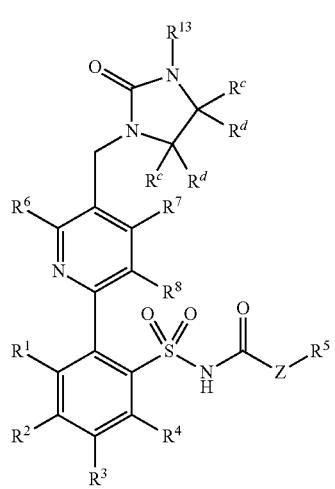
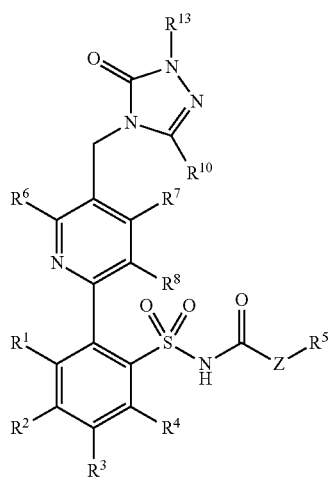
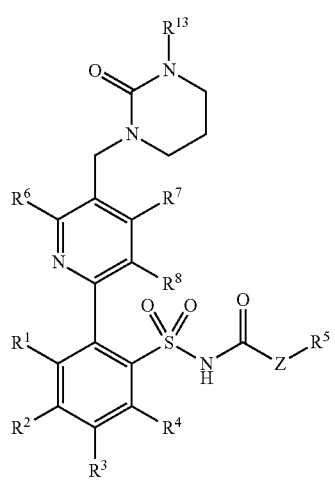

21
-continued

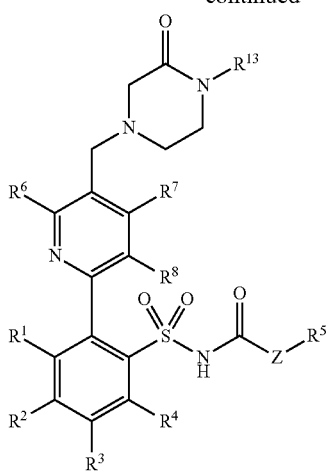

22
-continued

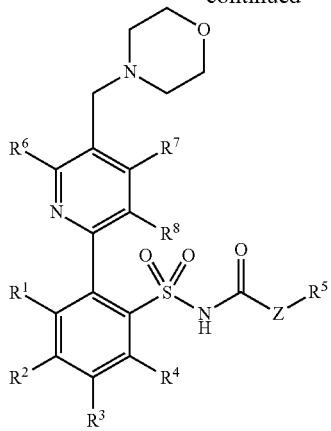

wherein:

$R^1$, $R^2$, $R^3$, $R^4$ $R^5$, $R^6$, $R^7$, $R^8$, $R^9$, $R^a$, $R^b$, $R^c$, $R^d$ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, or aryloxyalkyl.

In additional exemplary embodiments, the provided compounds have the general formula selected from a group consisting of:

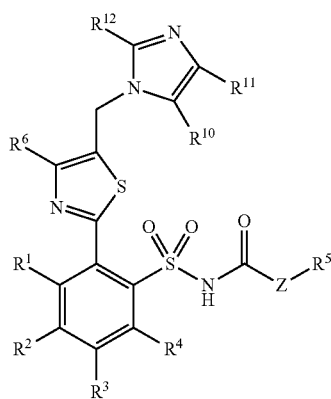

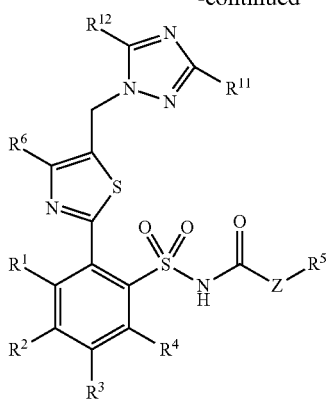
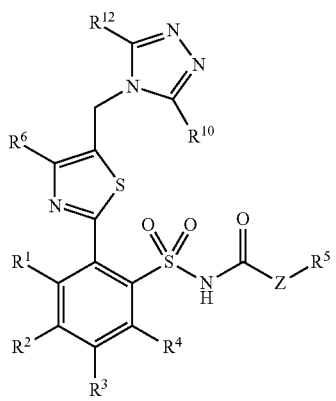
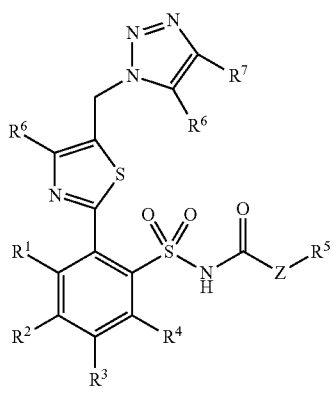
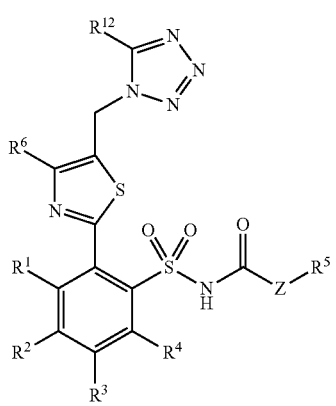
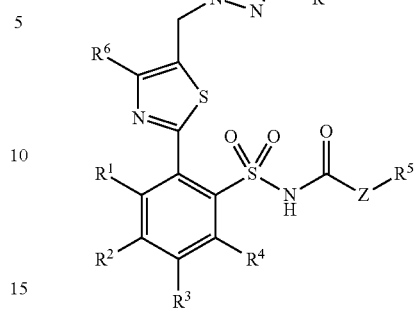
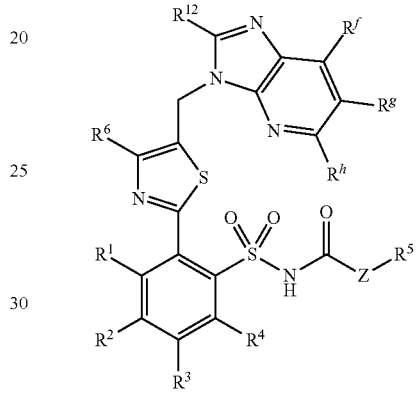
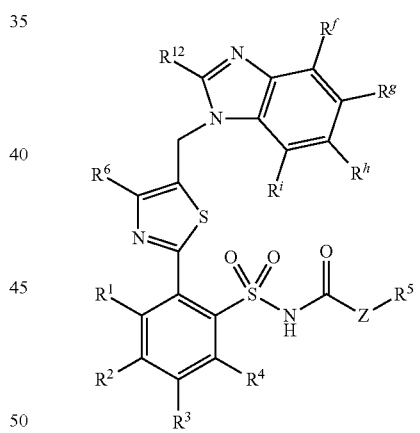
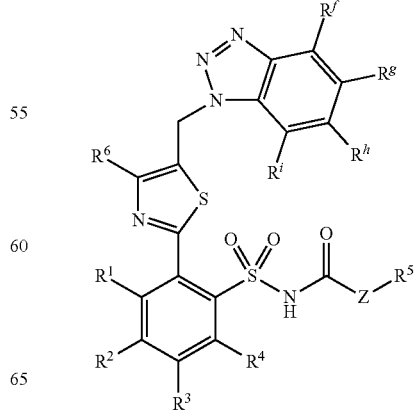

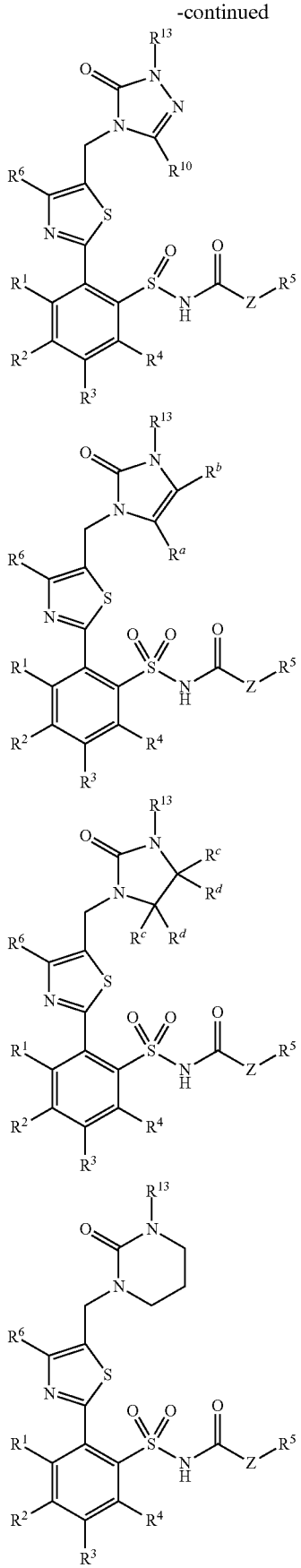
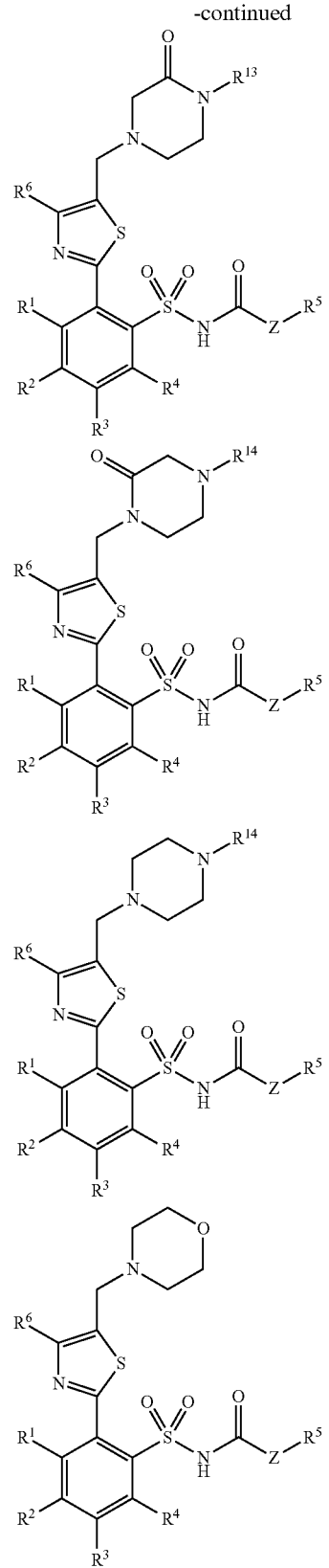
wherein:
R¹, R², R³, R⁴ R⁵, R⁶, R⁷, R⁸, R⁹, Rᵃ, Rᵇ, Rᶜ, Rᵈ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, or aryloxyalkyl.

In some preferred embodiments, the provided compounds have the general formula 2a,b or 3a,b:

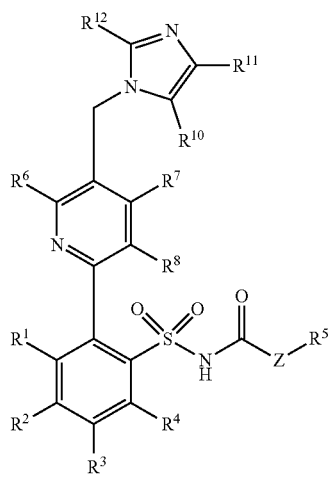

2a

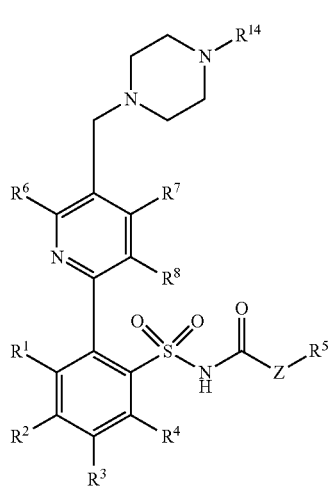

2b

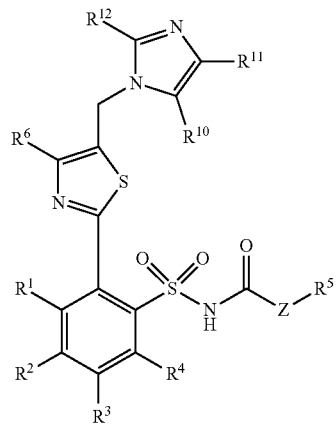

3a

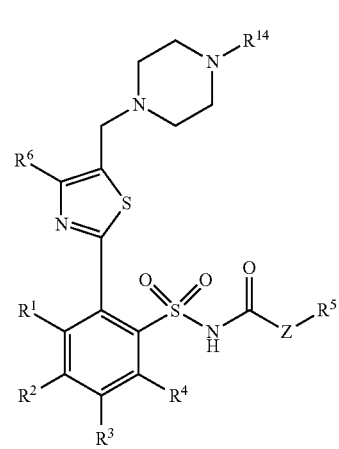

3b wherein:

$R^1$, $R^2$, $R^3$, $R^4$ $R^5$, $R^6$, $R^7$, $R^8$, $R^9$, $R^{10}$, $R^a$, $R^b$, $R^c$, $R^d$ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, or aryloxyalkyl.

In further preferred embodiments the invention provides compounds having the general formula 4a,b, 5a,b or 6a,b:

29

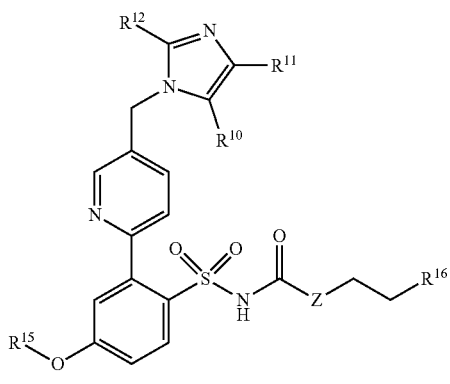
4a

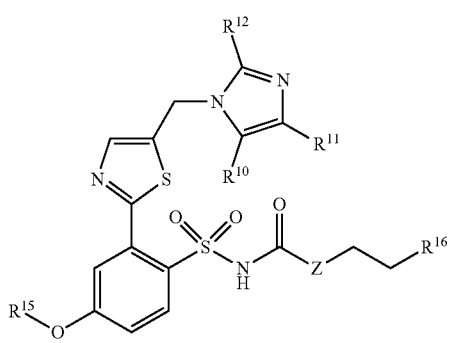
4b

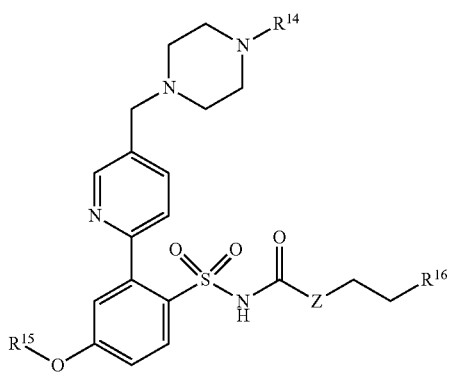
5a

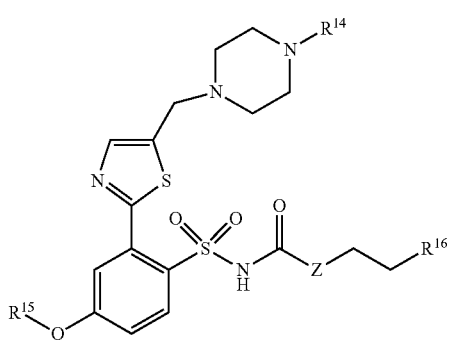
5b

30
-continued

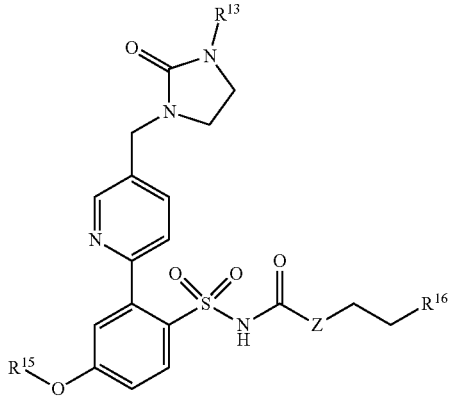
6a

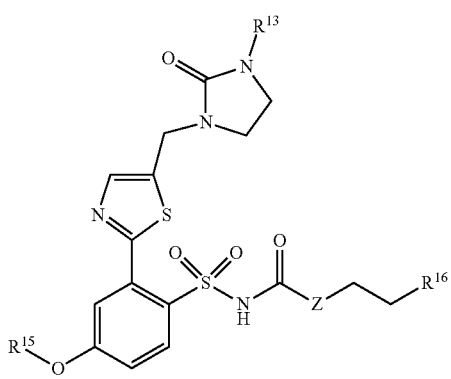
6b wherein:

$R^1$, $R^2$, $R^3$, $R^4$ $R^5$, $R^5$, $R^7$, $R^8$, $R^9$, $R^a$, $R^b$, $R^c$, $R^d$ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{14}$ is hydrogen, alkyl, aryl, heteroaryl, acyl, alkoxyacyl, aminoacyl, dialkylaminoacyl, or dialkylaminoacyl; and $R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

In some exemplary embodiments, the $R^{10}$, $R^{11}$ and $R^{12}$ are hydrogen, and $R^{14}$ is methyl.

In other exemplary embodiments, $R^{15}$ is trifluoromethyl and $R^{16}$ is ethyl.

Exemplary embodiments are provided by compounds 7, 8, 9, 10, and 11:

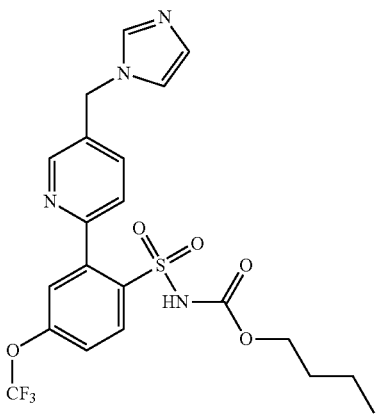

7

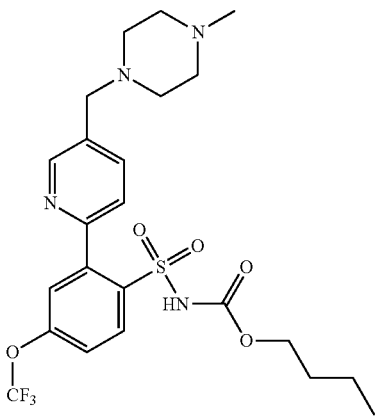

10

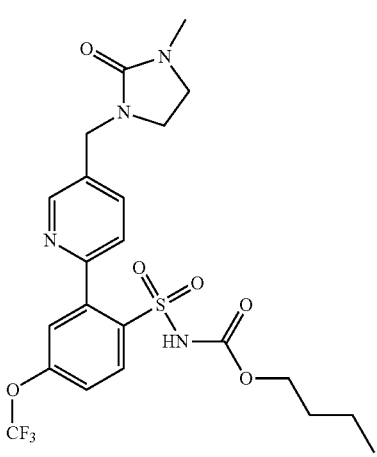

8

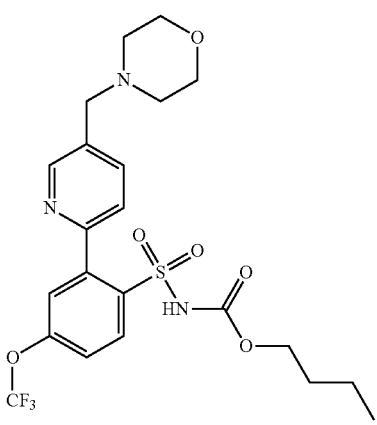

9

11

C. Preparation of the Compounds

The compounds provided herein may be prepared by methods known in the art or by the general methods known in the art and exemplified herein in the provided Examples 2-5.

The provided compounds of formula 1 can be prepared via two alternative methods, which involve combinations of two intermediates.

The first method for the preparation of compounds of formula 1 begins with Step 1 that involves the bromination of the heteroaryl bromide intermediate Ia to form intermediate Ib. In Step 2, intermediate Ib is reacted with the amine intermediate containing ring A of formula Ic to form intermediate Id. In Step 3, intermediate Id is reacted with the boronic acid or boronate intermediate of formula Ie (having a boron group B(OR)$_2$ wherein R is H, or alkyl) under palladium-mediated cross coupling conditions to form intermediate of formula If. In Step 4, the t-butyl protecting group of intermediate If is removed and the remaining functional group is introduced via methods known in the art to form compound of formula 1.

Step 1:

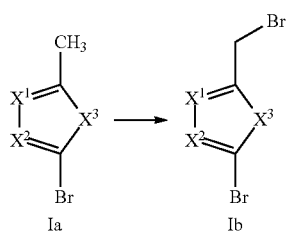

Step 2:

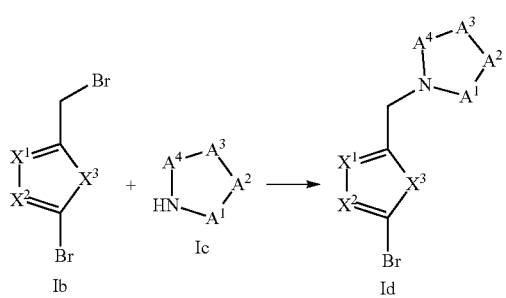

Step 3:

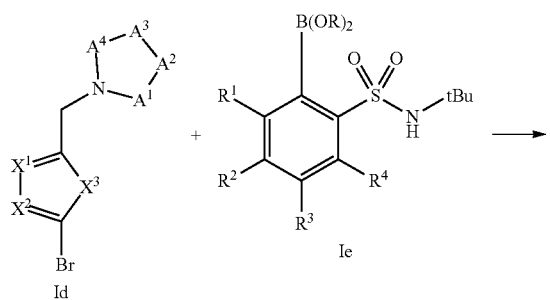

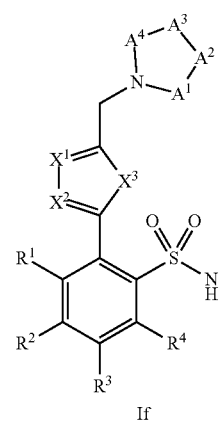

Step 4:

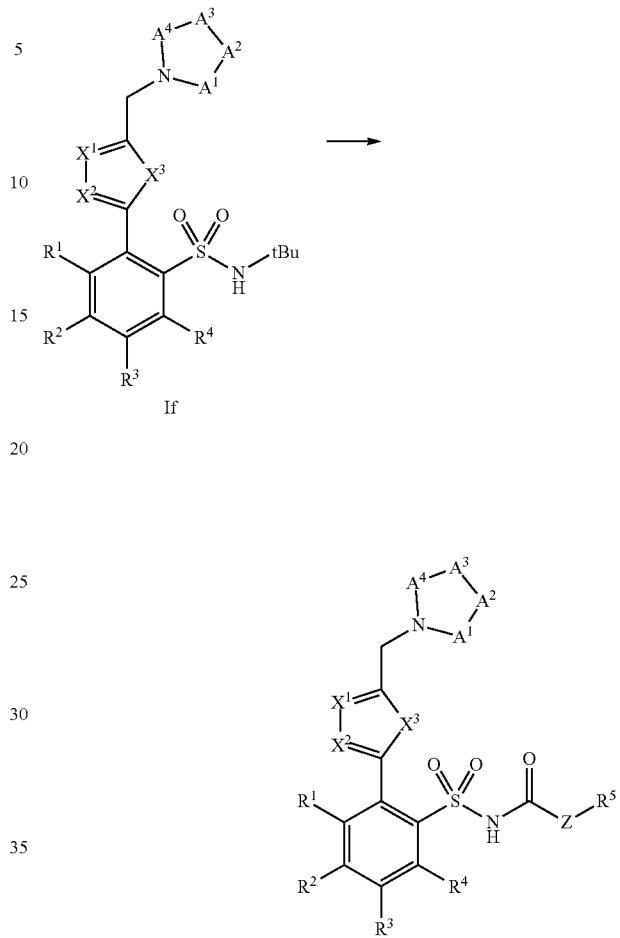

The second method involves a different order of these steps. In Step 1 the boronic acid or boronate intermediate of formula Ie is reacted with the heteroaryl bromide of formula Ia under palladium-mediated cross coupling condition to form intermediate Ig. In Step 2 intermediate Ig is brominated to form intermediate Ih. In Step 3 intermediate Ih is reacted with the amine intermediate containing ring A of formula Ic to form intermediate If. In Step 4, (described above) the t-butyl protecting group of intermediate If is removed and the remaining functional group is introduced via methods known in the art to form compound of formula 1.

Step 1:

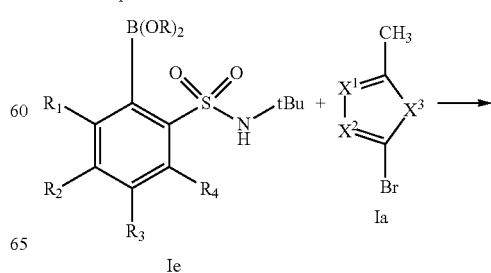

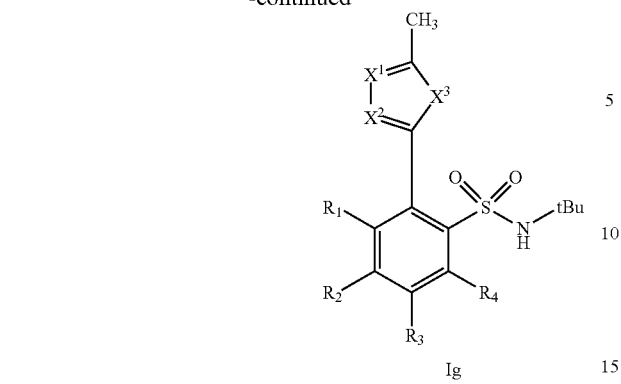
Ig
Step 2:
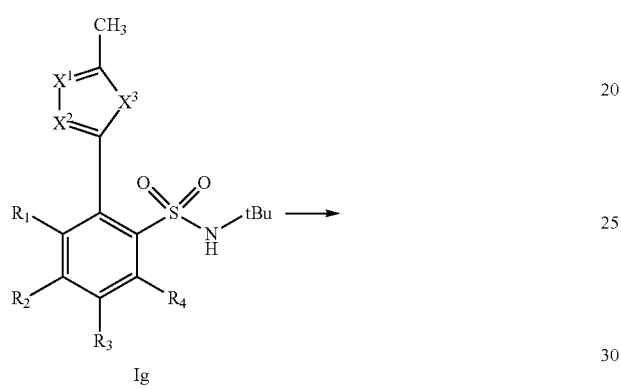
Ig
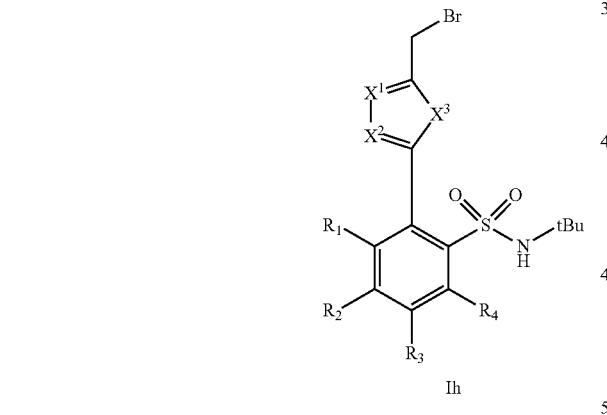
Ih
Step 3:
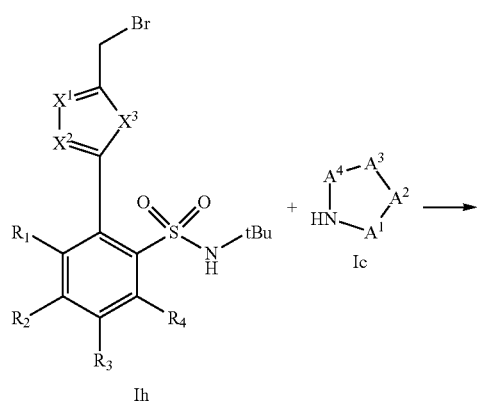
Ih
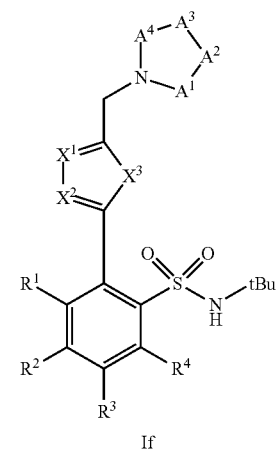
If
In a modified method intermediate Id is prepared via a reductive amination of aldehyde intermediate Ii with amine intermediate Ic.
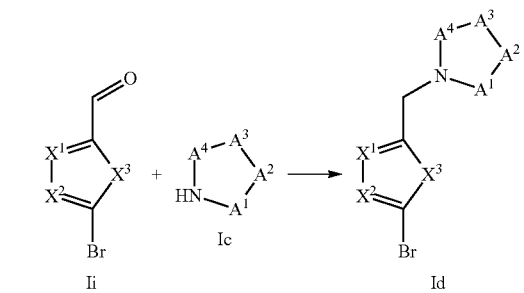
In another modified method intermediate If is prepared via a reductive amination of aldehyde intermediate Ij with amine intermediate Ic.
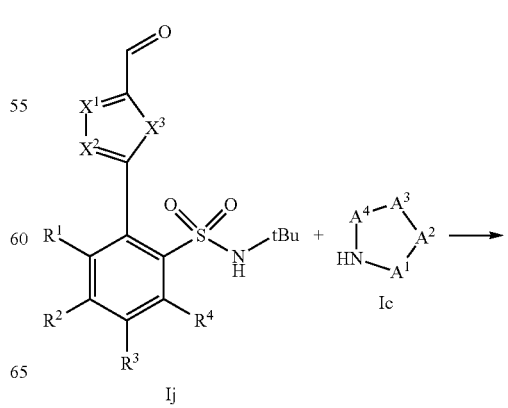
Ij

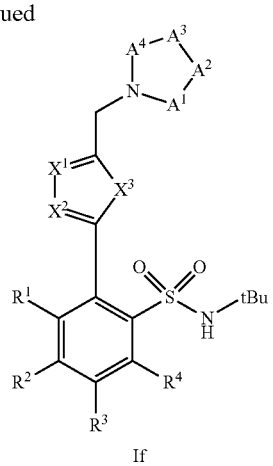

If

D. Formulation of pharmaceutical compositions

The pharmaceutical compositions provided herein contain therapeutically effective amounts of one or more of compounds provided herein or their salts thereof in a pharmaceutically acceptable carrier.

The compositions contain one or more compounds provided herein or their salts thereof. The compounds are preferably formulated into suitable pharmaceutical preparations such as solutions, suspensions, tablets, dispersible tablets, pills, capsules, powders, sustained release formulations or elixirs, for oral, buccal, intranasal, vaginal, rectal, ocular administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of conditions including, but not limited to, cardiovascular disease (myocardial infarction, congestive heart failure, diabetic cardiovascular disease, atrial fibrillation, hypertension, peripheral vascular disease, erectile dysfunction, stroke, pre-eclampsia, coated stents to inhibit restenosis, Marfan syndrome, and abdominal/thoracic aortic aneurysm), metabolic diseases (insulin resistance and metabolic syndrome), renal diseases (diabetic renal disease, drug-induced renal failure, and chronic renal failure), pulmonary diseases (pulmonary fibrosis, acute lung injury, pulmonary hypertension, and asthma), inflammatory and autoimmune diseases (arthritis, Crohn's disease, graft versus host disease, systemic sclerosis and multiple sclerosis), neurological diseases (depression, anxiety, dementia, Alzheimer's disease, neurodegenerative diseases, traumatic brain injury, peripheral neuropathy, spinal cord injury, and Huntington's disease), musculoskeletal diseases (muscular dystrophy and muscular injury), fibrotic diseases (scar reduction, pulmonary fibrosis, liver fibrosis and cardiac fibrosis), dermal diseases (wound healing, radiation mitigation, dermal repair, scar reduction, and alopecia), ocular diseases (macular degeneration, corneal scarring, and diabetic retinopathy), liver diseases (non alcoholic hepatosteatosis, hepatic fibrosis, hepatobilliary disease, fatty liver disease, cirrhosis, and liver fibrosis), oncology and related diseases (cancer and supportive care for oncology), gastrointestinal disease (stress ulcers and Crohn's disease), and bone marrow diseases (recovery from myelosuppression due to radiation or chemotherapy, autologous transplant, radiation mitigation, engraftment of transplant, allogenic transplant, engraftment, hematopoiesis and bone marrow injury, and myelodysplastic syndromes).

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated including but not limited to cardiovascular disease (myocardial infarction, congestive heart failure, diabetic cardiovascular disease, atrial fibrillation, hypertension, peripheral vascular disease, erectile dysfunction, stroke, pre-eclampsia, coated stents to inhibit restenosis, Marfan syndrome, and abdominal/thoracic aortic aneurysm), metabolic diseases (insulin resistance and metabolic syndrome), renal diseases (diabetic renal disease, drug-induced renal failure, and chronic renal failure), pulmonary diseases (pulmonary fibrosis, acute lung injury, pulmonary hypertension, and asthma), inflammatory and autoimmune diseases (arthritis, Crohn's disease, graft versus host disease, systemic sclerosis and multiple sclerosis), neurological diseases (depression, anxiety, dementia, Alzheimer's disease, neurode generative diseases, spinal cord injury, traumatic brain injury, peripheral neuropathy and Huntington's disease), musculoskeletal diseases (muscular dystrophy and muscular injury), fibrotic diseases (scar reduction, pulmonary fibrosis, liver fibrosis and cardiac fibrosis), dermal diseases (wound healing, radiation mitigation, dermal repair, scar reduction, and alopecia), ocular diseases (macular degeneration, corneal scarring, and diabetic retinopathy), liver diseases (non alcoholic hepatosteatosis, hepatic fibrosis, hepatobilliary disease, fatty liver disease, cirrhosis, and liver fibrosis), oncology and related diseases (cancer and supportive care for oncology), gastrointestinal disease (stress ulcers and Crohn's disease), and bone marrow diseases (recovery from myelosuppression due to radiation or chemotherapy, autologous transplant, radiation mitigation, engraftment of transplant, allogenic transplant, engraftment, hematopoiesis and bone marrow injury, and myelodysplastic syndromes).

Typically a therapeutically effective dosage should produce a serum or plasma concentration of active ingredient of from about 0.1 ng/ml to about 50-100 µg/ml. The pharmaceutical compositions typically should provide a dosage of from about 0.001 mg to about 100 mg of compound per kilogram of body weight per day. Pharmaceutical dosage unit forms are prepared to provide from about 1 mg to about 2,000 mg and preferably from about 10 to about 200 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions. Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with cardiovascular disease (myocardial infarction, congestive heart failure, diabetic cardiovascular disease, atrial fibrillation, hypertension, peripheral vascular disease, erectile dysfunction, stroke, pre-eclampsia, coated stents to inhibit restenosis, Marfan syndrome, and abdominal/thoracic aortic aneurysm), metabolic diseases (insulin resistance and metabolic syndrome), renal diseases (diabetic renal disease, drug-induced renal failure, and chronic renal failure), pulmonary diseases (pulmonary fibrosis, acute lung injury, pulmonary hypertension, and asthma), inflammatory and autoimmune diseases (arthritis, Crohn's disease, graft versus host disease, systemic sclerosis and multiple sclerosis), neurological diseases (depression, anxiety, dementia, Alzheimer's disease, neurodegenerative diseases, spinal cord injury, traumatic brain injury, peripheral neuropathy, and Huntington's disease), musculoskeletal diseases (muscular dystrophy and muscular injury), fibrotic diseases (scar reduction, pulmonary fibrosis, liver fibrosis and cardiac fibrosis), dermal diseases (wound healing, radiation mitigation, dermal repair, scar reduction, and alopecia), ocular diseases (macular degeneration, corneal scarring, and diabetic retinopathy), liver diseases (non alcoholic hepatosteatosis, hepatic fibrosis, hepatobilliary disease, fatty liver disease, cirrhosis, and liver fibrosis), oncology and related diseases (cancer and supportive care for oncology), gastrointestinal disease (stress ulcers and Crohn's disease), and bone marrow diseases (recovery from myelosuppression due to radiation or chemotherapy, autologous transplant, radiation mitigation, engraftment of transplant, allogenic transplant, engraftment, hematopoiesis and bone marrow injury, and myelodysplastic syndromes). The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, intravenously, vaginal, intranasal, buccal, sublingual, rectally, ocularly, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, hydroxyethyl cellulose (HEC), β-cyclodextin, hydroxypropyl β-cyclodextrin, carboxymethyl cellulose colloidal solutions, hydroxyethyl cellulose colloidal solutions polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In another embodiment, the bioactive lipid(s) are administered in a polymer formulation, including but not limited to Poly-D,L-Lactic-Co-Glycolic Acid (PLGA), poly-lactic acid (PLA), PLA-PLGA co-polymers, polycaprolactone particles, and chitosan nanoparticles.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical compositions of the present invention may be advantageously provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain, along with the active ingredient, a diluent such as lactose, sucrose, dicalcium phosphate, or carboxymethylcellulose; a lubricant, such as magnesium stearate, calcium stearate and talc; and a binder such as starch, natural gums, such as gum *acacia*, gelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time-release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, including but not limted to cardiovascular disease (myocardial infarction, congestive heart failure, diabetic cardiovascular disease, atrial fibrillation, hypertension, peripheral vascular disease, erectile dysfunction, stroke, pre-eclampsia, coated stents to inhibit restenosis, Marfan syndrome, and abdominal/thoracic aortic aneurysm), metabolic diseases (insulin resistance and metabolic syndrome), renal diseases (diabetic renal disease, drug-induced renal failure, and chronic renal failure), pulmonary diseases (pulmonary fibrosis, acute lung injury, pulmonary hypertension, and asthma), inflammatory and autoimmune diseases (arthritis, Crohn's disease, graft versus host disease, systemic sclerosis and multiple sclerosis), neurological diseases (depression, anxiety, dementia, Alzheimer's disease, neurodegenerative diseases, spinal cord injury, traumatic brain injury, peripheral neuropathy and Huntington's disease), musculoskeletal diseases (muscular dystrophy and muscular injury), fibrotic diseases (scar reduction, pulmonary fibrosis, liver fibrosis and cardiac fibrosis), dermal diseases (wound healing, radiation mitigation, dermal repair, scar reduction, and alopecia), ocular diseases (macular degeneration, corneal scarring, and diabetic retinopathy), liver diseases (non alcoholic hepatosteatosis, hepatic fibrosis, hepatobilliary disease, fatty liver disease, cirrhosis, and liver fibrosis), oncology and related diseases (cancer and supportive care for oncology), gastrointestinal disease (stress ulcers and Crohn's disease), and bone marrow diseases (recovery from myelosuppression due to radiation or chemotherapy, autologous transplant, radiation mitigation, engraftment of transplant, allogenic transplant, engraftment, hematopoiesis and bone marrow injury, and myelodysplastic syndromes). It is to be understood that such combination therapy constitutes a further aspect of the compositions and methods of treatment provided herein.

1. Compositions for Oral or Mucocutaneous Administration

Oral pharmaceutical dosage forms are solid, gel or liquid. The solid dosage forms are tablets, capsules, granules, and bulk powders. Types of oral tablets include compressed, chewable lozenges and tablets that may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules, suppositories, rapid dissolving forms (e.g. films, and redi-tablets) or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, *acacia* mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water-soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds, which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets, which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, *acacia*, tragacanth, bentonite, and surfactants such as polyoxyethylene sorbitan monooleate. Suspending agents include sodium carboxymethylcellulose, pectin, tragacanth, Veegum and *acacia*. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds, which produce a pleasant, taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Patent Nos. Re 28,819 and 4,358,603 (the relevant portions thereof are incorporated herein by reference). Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate-controlling step. The percentage of active compound contained in such parenteral compositions is highly dependent on the specific nature thereof, as well as the activity of the compound and the needs of the subject.

Parenteral administration of the compositions includes intradermal, intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Formulations contemplated herein also include lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient, which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-2,000 mg, preferably 100-500 mg) or multiple dosages of the compound for appropriate dosing. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma or other pulmonary conditions, the relevant portions thereof are incorporated herein by reference). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH ~5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives thereof can be packaged as articles of manufacture containing packaging material, a compound or pharmaceutically acceptable derivative thereof provided herein, which is used for treatment, prevention or amelioration of one or more symptoms associated the diseases including but not limited to cardiovascular disease (myocardial infarction, congestive heart failure, diabetic cardiovascular disease, atrial fibrillation, hypertension, peripheral vascular disease, erectile dysfunction, stroke, pre-eclampsia, coated stents to inhibit restenosis, Marfan syndrome, and abdominal/thoracic aortic aneurysm), metabolic diseases (insulin resistance and metabolic syndrome), renal diseases (diabetic renal disease, drug-induced renal failure, and chronic renal failure), pulmonary diseases (pulmonary fibrosis, acute lung injury, pulmonary hypertension, and asthma), inflammatory and autoimmune diseases (arthritis, Crohn's disease, graft versus host disease, systemic sclerosis and multiple sclerosis), neurological diseases (depression, anxiety, dementia, Alzheimer's disease, neurodegenerative diseases, spinal cord injury, traumatic brain injury, peripheral neuropathy, and Huntington's disease), musculoskeletal diseases (muscular dystrophy and muscular injury), fibrotic diseases (scar reduction, pulmonary fibrosis, liver fibrosis and cardiac fibrosis), dermal diseases (wound healing, radiation mitigation, dermal repair, scar reduction, and alopecia), ocular diseases (macular degeneration, corneal scarring, and diabetic retinopathy), liver diseases (non alcoholic hepatosteatosis, hepatic fibrosis, hepatobilliary disease, fatty liver disease, cirrhosis, and liver fibrosis), oncology and related diseases (cancer and supportive care for oncology), gastrointestinal disease (stress ulcers and Crohn's disease), and bone marrow diseases (recovery from myelosuppression due to radiation or chemotherapy, autologous transplant, radiation mitigation, engraftment of transplant, allogenic transplant, engraftment, hematopoiesis and bone marrow injury, and myelodysplastic syndromes) and a label that indicates that the compound or pharmaceutically acceptable derivative thereof is used for treatment, prevention or amelioration of one or more symptoms associated with the aforementioned diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252 (the relevant portions thereof are incorporated herein by reference). Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder associated with cardiovascular disease (myocardial infarction, congestive heart failure, diabetic cardiovascular disease, atrial fibrillation, hypertension, peripheral vascular disease, erectile dysfunction, stroke, pre-eclampsia, coated stents to inhibit restenosis, Marfan syndrome, and abdominal/thoracic aortic aneurysm), metabolic diseases (insulin resistance and metabolic syndrome), renal diseases (diabetic renal disease, drug-induced renal failure, and chronic renal failure), pulmonary diseases (pulmonary fibrosis, acute lung injury, pulmonary hypertension, and asthma), inflammatory and autoimmune diseases (arthritis, Crohn's disease, graft versus host disease, systemic sclerosis and multiple sclerosis), neurological diseases (depression, anxiety, dementia, Alzheimer's disease, neurodegenerative diseases, spinal cord injury, traumatic brain injury, peripheral neuropathy, and Huntington's disease), musculoskeletal diseases (muscular dystrophy and muscular injury), fibrotic diseases (scar reduction, pulmonary fibrosis, liver fibrosis and cardiac fibrosis), dermal diseases (wound healing, radiation mitigation, dermal repair, scar reduction, and alopecia), ocular diseases (macular degeneration, corneal scarring, and diabetic retinopathy), liver diseases (non alcoholic hepatosteatosis, hepatic fibrosis, hepatobilliary disease, fatty liver disease, cirrhosis, and liver fibrosis), oncology and related diseases (cancer and supportive care for oncology), gastrointestinal disease (stress ulcers and Crohn's disease), and bone marrow diseases (recovery from myelosuppression due to radiation or chemotherapy, autologous transplant, radiation mitigation, engraftment of transplant, allogenic transplant, engraftment, hematopoiesis and bone marrow injury, and myelodysplastic syndromes).

E. Methods of Use and Treatment Methods of the Compounds and Compositions

The provided compounds can act selectively at certain GPCR receptors and can be used as selective agonists of these receptors.

Compounds provided by the invention act as small molecule modulators of the actions of angiotensin-related peptides. The provided compounds can act as agonists of the Mas receptor, otherwise known as the receptor of the Ang (1-7) peptide. As part of, or in addition to or instead of their actions of the angiotensin receptors, the provided compounds can mimic the endogenous actions of the Ang(1-7) peptide and benefit from all of its beneficial activities and therapeutic actions.

In a preferred embodiment, the provided compounds may be used as selective agonists of the Mas receptor and do not act as agonists of the AngII receptor AT1R. In another preferred embodiment, the provided compounds may be used as agonists of the Mas receptor and/or as agonists of the AngII receptor AT2R, but do not act as agonists of the AngII receptor AT1R. In another preferred embodiment, the provided compounds act as agonists of the Mas receptor and/or as agonists of the AngII receptor AT2R, but do not act as antagonists of the AngII receptor AT1R.

In one embodiment, the invention provides pharmaceutical compositions containing a provided compound of formula 1 or its salt thereof and any acceptable carrier that are useful for therapeutic administration.

In another embodiment the invention provides a method of increasing NO production in a cell comprising contacting the cell with an effective amount of a compound according to formula 1 (or any formulas disclosed herein derived from formula 1, such as formulas 2-11) or salts thereof.

In another embodiment the invention provides a method of reducing blood glucose in a patient in need thereof comprising, administering to the patient in an effective amount of a compound according to formula 1 (or any formulas disclosed herein derived from formula 1, such as formulas 2-11) or salts thereof.

In a preferred embodiment, the provided method is used in a patient that has diabetes mellitus.

In another embodiment the invention provides a method for reducing fat accumulation in a patient in need thereof comprising, administering to the patient in an effective amount of a compound according to formula 1 (or any formulas disclosed herein derived from formula 1, such as formulas 2-11) or salts thereof.

In a preferred embodiment, the provided method is used in a patient that has non-alcoholic steatohepatitis.

In another embodiment the invention provides a method of enhancing bone marrow progenitor cell proliferation in a patient in need thereof comprising administering to the patient an effective amount of a compound according to formula 1 (or any formulas disclosed herein derived from formula 1, such as formulas 2-11) or salts thereof.

In a preferred embodiment, the provided method is used in a patient that has myelodysplastic syndrome.

In another embodiment the invention provides a method for treating a patient with cancer comprising, administering to the patient in an effective amount of a compound according to formula 1 (or any formulas disclosed herein derived from formula 1, such as formulas 2-11) or salts thereof.

In a preferred embodiment, the provided method is used in a patient that has breast cancer.

In another embodiment the invention provides a method of treating an angiotensin-related disease or disorder comprising: administering to a patient in need thereof an effective amount of a provided compound a provided compound of formula 1 (or any formulas disclosed herein derived from formula 1, such as formulas 2-11) or salts thereof, or a pharmaceutical composition containing a provided compound, wherein the amount of compound is effective to ameliorate at least one symptom associated with the disease or disorder, or to postpone or prevent the onset of at least one symptom of the disease.

In an exemplary embodiment, the invention provides compounds, methods and compositions for the treatment of diseases mediated by angiotensin II acting on its receptor type I (AT1R) or via other pathways. Accordingly, in one aspect, the invention features methods and compositions for modulating, ameliorating or treating diseases or conditions associated with the adverse actions of an angiotensin-related peptide, such as angiotensin II.

In another embodiment, the invention provides a method for the use of a provided compound a provided compound of formula 1 or its salt thereof and compositions for the treatment of diseases or disorders and related conditions mediated by the undesired actions of an angiotensin-related peptide, such as angiotensin II. In another embodiment, the invention provides a method for the use of the provided compounds and compositions for the treatment of disorders mediated by reduced stem/progenitor cell activity.

The invention provides small molecule non-peptidic compounds, as well as methods and compositions for the treatment of angiotensin-related diseases and disorders, including but not limited to cardiovascular disease (myocardial infarction, congestive heart failure, diabetic cardiovascular disease, atrial fibrillation, hypertension, peripheral vascular disease, erectile dysfunction, stroke, pre-eclampsia, coated stents to inhibit restenosis, Marfan syndrome, and abdominal/thoracic aortic aneurysm), metabolic diseases (insulin resistance and metabolic syndrome), renal diseases (diabetic renal disease, drug-induced renal failure, and chronic renal failure), pulmonary diseases (pulmonary fibrosis, acute lung injury, pulmonary hypertension, and asthma), inflammatory and autoimmune diseases (arthritis, Crohn's disease, graft versus host disease, systemic sclerosis and multiple sclerosis), neurological diseases (depression, anxiety, dementia, Alzheimer's disease, neurodegenerative diseases, spinal cord injury, traumatic brain injury, peripheral neuropathy and Huntington's disease), musculoskeletal diseases (muscular dystrophy and muscular injury), fibrotic diseases (scar reduction, pulmonary fibrosis, liver fibrosis and cardiac fibrosis), dermal diseases (wound healing, radiation mitigation, dermal repair, scar reduction, and alopecia), ocular diseases (macular degeneration, corneal scarring, and diabetic retinopathy), liver diseases (non alcoholic hepatosteatosis, hepatic fibrosis, hepatobilliary disease, fatty liver disease, cirrhosis, and liver fibrosis), oncology and related diseases (cancer and supportive care for oncology), gastrointestinal disease (stress ulcers and Crohn's disease), and bone marrow diseases (recovery from myelosuppression due to radiation or chemotherapy, autologous transplant, radiation mitigation, engraftment of transplant, allogenic transplant, engraftment, hematopoiesis and bone marrow injury, and myelodysplastic syndromes).

In a preferred embodiment, the invention provides compounds, methods and compositions for the treatment of metabolic diseases or disorders and related conditions, such as diabetes mellitus, diabetes-related cardiovascular disorders, diabetes-related dermal ulcerations, diabetes-related hypertension, diabetic ophthalmic diseases, and obesity-related diseases or conditions.

In an exemplary embodiment, the provided compounds, methods and compositions are used for the reduction in the consequences of hyperglycemia in diabetic patients without the effects of hypoglycemia.

In other exemplary embodiments, the provided compounds and compositions can be used to treat an angiotensin-related disease or disorder and related conditions, including: cardiovascular disease, renal disease, hematologic disease, fibrotic disease, liver disease, autoimmune/inflammatory disease, metabolic disease, pulmonary disease, diabetes, ophthalmic disease, neurologic disease, or cancer.

More particularly, the invention provides a method of using the provided compounds and pharmaceutical compositions for the treatment of multiple angiotensin-related diseases or disorders.

In one exemplary embodiment, the invention provides methods and compositions for the treatment of a known angiotensin-related disease.

In a preferred embodiment, the invention provides a method for the treatment of diabetes, obesity or another disease of the metabolic system.

Preferred methods and compositions include pharmaceutical compositions for topical, parenteral and oral administration comprising of a provided compound and derivatives or a pharmaceutically acceptable salt, and a pharmaceutically acceptable carrier. The invention also provides a method of use of the provided pharmaceutical compositions for the treatment of angiotensin-related diseases and disorders.

In an exemplary embodiment, the invention provides methods and compositions for the treatment of metabolic diseases and disorders, including diabetes and related conditions, upon oral, parenteral (e.g. subcutaneous, intrathecal, epidural, and intravenous) and topical administration, such as delivery to the skin, the eye, or the mucosa.

In another embodiment, the provided compounds, methods and compositions are employed in oral, parenteral, or topical administration comprising of a provided compound or a pharmaceutically acceptable salt, and a pharmaceutically acceptable carrier.

The invention will be further described in the following examples, which are illustrative only, and which are not intended to limit the scope of the invention described in the claims.

EXAMPLES

Example 1

Structure-Based Design and Identification of Non-Peptidic Small Molecules that Selectively Bind to the Mas Receptor The provided compounds were designed to have beneficial agonist activity at the Mas receptor, without adverse agonist activity at the AT1 receptor. Since there are no available X-ray crystal structures for the relevant angiotensin receptors, such as the AT1, AT2 and Mas receptors, the provided compounds were defined by using GPCR homology modeling to evaluate key structural features. Homology models of these receptors were generated using the Prime (Prime, v3.1, Schrödinger, LLC, New York, N.Y.) homology workflow. The sequence of AT1, AT2, and MAS were downloaded from Universal Protein Resource (UniProt). The sequence for the AT2R and MAS receptor was aligned with the sequence of the nociceptin/orphanin FQ receptor (PDB ID: 4EA3 Chain A) in the Prime homology workflow placing gaps in the loops regions. Prime was used to construct a homology model using a knowledge-based building method. The extracellular loops of the output homology structure were deleted in the Maestro workspace and Schrodinger's Protein Preparation Wizard tool was used to add hydrogens, correct bond orders, delete non-essential waters, predict side-chain protonation states, tautomers, and polar hydrogen orientations, and minimize the energy of the protein structure. The orthosteric site of the homology model was analyzed for polar residues capable of hydrogen bonding with the molecules.

Using these homology models, several exemplary series of compounds were modeled, optimized, prepared, and evaluated in binding displacement assays with Ang II and Ang(1-7), as well in other related assays. These studies resulted in the identification and validation of the key relevant structural features of the provided compounds.

A representative example involving a model related to the exemplary compound 7 is provided in FIG. 2. For clarity, these models show only an ethyl group in place of the butyl group of compound 7. In this example, the binding preference of compound 7 (FIG. 2A-D) at the AT2R is compared with the pyrazole isomer of compound 7 (FIG. 2E). Despite their small difference in structure, their binding orientation is significantly altered pointing to the importance of the more basic nitrogen atom in compound 7. In another comparison of compound 7 with the corresponding compound where the pyridine ring is replaced with a benzene ring (FIG. 2F-H), indicated that the presence of a basic nitrogen in compound 7, which is presumably protonated, prevents this compound from inserting itself into the non-polar environment of the sub-surface portion of these GPCRs, which is preferrd by the diphenyl structure (FIG. 2G-H). Instead, compound 7 is able to bind via an alternative orientation closer to the surface (FIG. 2B-D). An alterantive preference exists for the closely related compound where the pyridine ring is replaced with a benzene ring (FIG. 2F-H). The overall orientation of the bound compounds (FIGS. 2B vs 2G and 2D vs 2H), as well as the contact residues at the binding site of the transmembrane GPCRs (FIGS. 2C vs 2E and 2F), are dramatically altered with the presence of the basic nitrogen present in compounds such as 7, enabling these compounds to differentially bind to AT2R. The binding of these compounds to AT1R and the Mas receptor has analogous differences, resulting in differentiated activity profiles.

Overall, these models reveal key structural features required by the provided compounds to function as selective agonists of Mas, without significant agonist or antagonist activity of AT1R or AT2R. By adopting these differentiated binding preferences, the provided compounds are not able to properly bind to AT1R and AT2R, and they are expected to be unable to behave as effective agonists or antagonists of these receptors.

Figure 3:
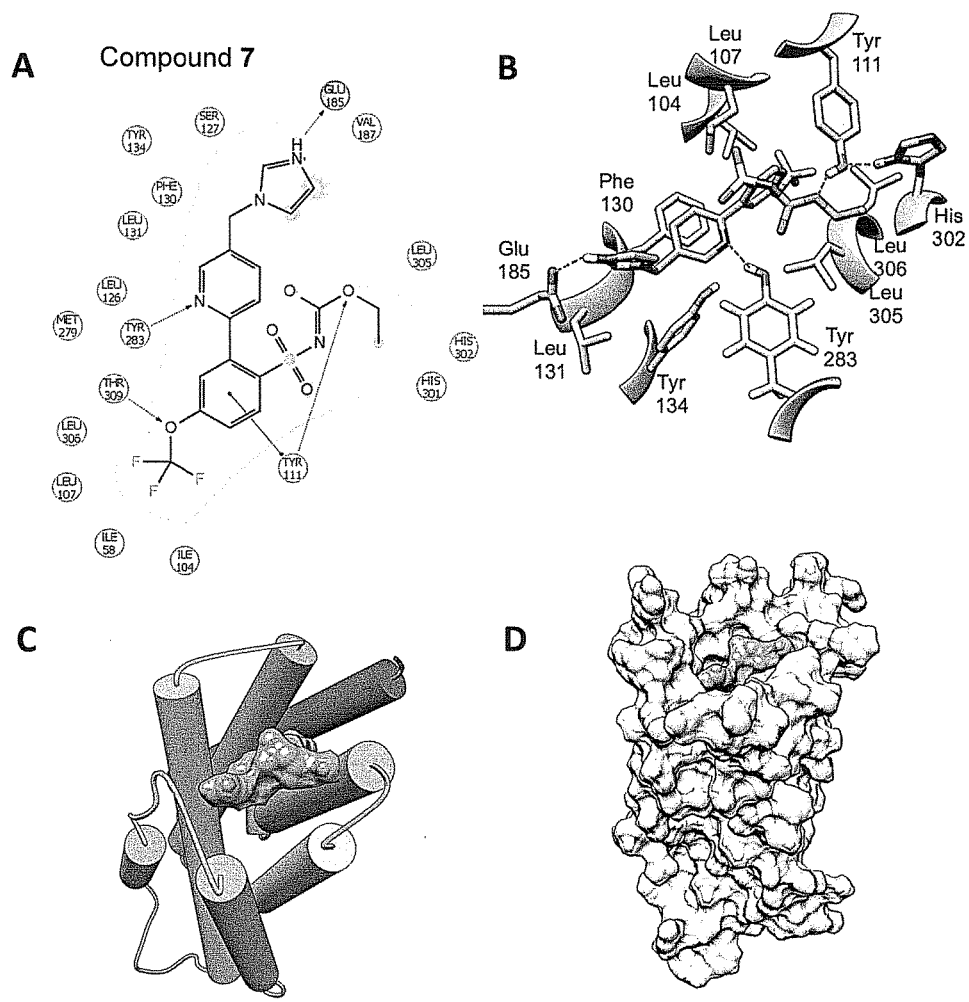
FIG. 3: Binding motifs of the provided compounds at a homology model of the Mas receptor. (A) Contact residues at the binding site of exemplary compound 7 at the Mas receptor. (B) Model of compound 7 docked into a Mas receptor homology model, showing selected residues involved in the binding site. For clarity, the models of this Figure show only an ethyl group in place of the butyl group of compound 7. (C)-(D) Overall orientation of compound 7 in its binding site at the Mas receptor.
Figure 7:
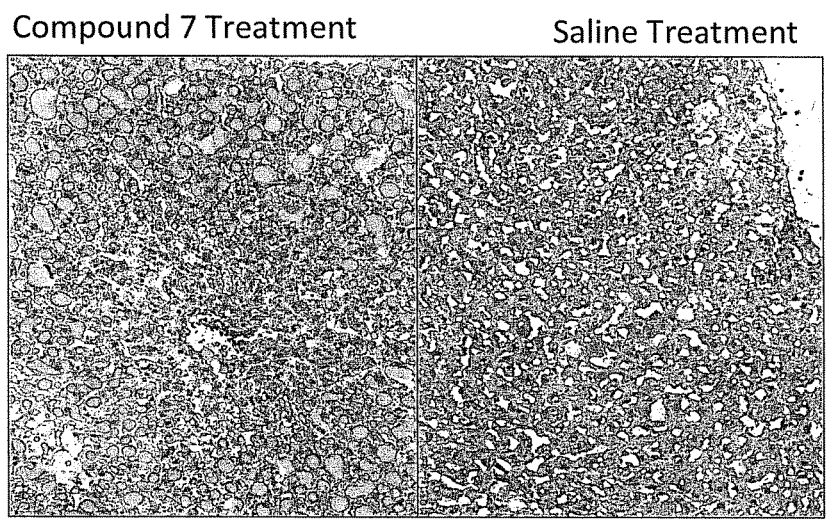
FIG. 7: Lipid levels in the liver was evaluated in db/db animals treated for 14 days with vehicle, 500 µg/kg/day Ang(1-7) and compound 7. Liver from compound 7 (right panel) treated mice had a reduced Oil Red staining (red droplets reflect lipid deposition) when compared with db/db controls (treated with saline) (left panel).

A representative example involving a model related to the postulated binding of exemplary compound 7 to the Mas receptor is provided in FIG. 3. For clarity, these models show only an ethyl group in place of the butyl group of compound 7. The postulated binding preference of compound 7 at a homology model of the Mas receptor revealed several strong binding interactions with polar residues at the binding site (FIG. 3B). The presence of a basic nitrogen, which is presumably protonated, as well as the other polar groups in compound 7 enables this compound to interact strongly at this polar site of the Mas Receptor. The contact residues at the binding site (FIG. 3A), and the overall orientation of the bound compound closer to the surface of the Mas receptor (FIG. 3C,D) point to the unique binding profile of the provided compounds that enables their ability to act as selective Mas receptor agonists. In contrast, similar compounds without such features are expected to act more differentially at the AT1R and/or AT2R without significant agonist activity at the Mas receptor.

These binding motifs that prevent effective binding to AT1R and AT2R, but at the same time enable effective selective binding to the Mas receptor are not known in the art, and provide strong support for the structural novelty of the provided exemplary compounds, which is also reflected in the corresponding exemplary binding data and the other exemplary biological data provided herein.

Example 2

Synthesis of Exemplary Compound 7(butyl(2-(5-((1H-imidazol-1-yl)methyl)pyridin-2-yl)-4-(trifluoromethoxy)phenyl)sulfonylcarbamate)

In the following synthetic examples, efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric. Starting materials used in these examples are generally either commercially available or can be readily prepared from commercially available reagents by a procedure involving one or more steps.

Step 1: Synthesis of 5-((1H-imidazol-1-yl)methyl)-2-bromopyridine. The starting material 2-bromo-5-(bromomethyl)pyridine was synthesized according to a published protocol (*Tetr. Lett.* 2002, 43, 1697). To a stirring solution of this compound (2 g, 8 mmol) in 20 mL of DMF was added imidazole (537 mg, 8 mmol, 1 eq) and $K_2CO_3$ (3.32 g, 24 mmol, 3 eq) and stirred overnight. The reaction was concentrated in vacuo. The crude mixture was dissolved in EtOAc and 10 mL of 10% citric acid and extracted. The organic layer was washed with $H_2O$ then brine, dried with $MgSO_4$, concentrated in vacuo, and purified by automated chromatography to yield 1.35 g of an off-white solid (71% yield, $R_f$=0.30 in 10% MeOH in DCM). $^1H$ NMR (400 MHz, CDCN) d 8.26 (d, J=2.4 Hz, 1H), 7.61 (s, 1H), 7.51 (d, J=8.2 Hz, 1H), 7.45 (dd, J=8.3, 2.5 Hz, 1H), 7.04 (s, 1H), 6.97 (s, 1H), 5.15 (s, 2H).

Step 2: Synthesis of N-(tert-butyl)-4-(trifluoromethoxy)benzene-sulfonamide. To a 500 mL round bottom flask equipped with a stirbar was added 4-(trifluoromethoxy)benzene-1-sulfonyl chloride, (25 g, 95.9 mmol) and 100 mL of THF and the flask was cooled to 0° C. Tert-butylamine (100 mL, 959 mmol, 10 eq) was dissolved in 100 mL of THF in an Erlenmeyer flask. The first 50 mL of the tert-butylamine solution was added dropwise to the sulfonyl chloride solution with the remaining poured directly from the Erlenmeyer Flask. After the reaction was stirred for 2 hours in the ice bath, the bath was removed and the reaction stirred at room temperature for 1 hour. The reaction was concentrated under vacuum to yield a white solid which was dissolved in $H_2O$ and EtOAc, placed in a separatory funnel, and extracted. The organic layer was washed with $H_2O$, a 10% aqueous solution of HCl, saturated $NaHCO_3$ solution, brine, dried with $MgSO_4$, filtered through cotton, and concentrated in vacuo to yield 28.26 g (quantitative) of a yellow oil which solidified under vacuumed stirring to a yellow crystalline solid. $^1H$ NMR (400 MHz, $CDCl_3$) d 7.90 (d, J=8.8 Hz, 2H), 7.23 (d, J=8.3 Hz, 2H), 5.32 (s, 1H), 1.15 (s, 9H). $^{13}$C NMR (101 MHz, CDCl$_3$) d 151.80 (q, J=1.8 Hz), 142.04, 129.12, 120.87 (d, J=1.0 Hz), 120.35 (q, J=259.1 Hz), 55.01, 30.15. $^{19}$F NMR (376 MHz, CDCl$_3$) d −57.87.

Step 3: Synthesis of (2-(N-(tert-butyl)sulfamoyl)-5-(trifluoromethoxy)phenyl)boronic acid. N-(tert-butyl)-4-(trifluoromethoxy)benzenesulfonamide (28.26 g, 95 mmol) was placed in a 500 mL round bottom flask equipped with a stir bar and placed under high vacuum with stirring. A solid yellow crystalline solid formed which was broken up with a large NMR tube and placed under additional high vacuum. 300 mL of DriSolv® THF was cannulated into the flask. The pressure was equilibrated with an argon balloon and the flask was cooled to ~−78° C. in an acetone and dry ice bath. 2.5 M n-butyl lithium (114 mL, 285 mmol, 3 eq) was added drop wise to the flask while maintaining the acetone and dry ice bath. The flask was quickly transferred to an acetonitrile and dry ice bath and stirred for 3.5 hours. (Place the reaction in the crushed dry ice then add the acetonitrile). The reaction was then cooled to ~−78° C. in an acetone and dry ice bath and triisopropyl borate (33 mL, 142.5 mmol, 1.5 eq) slowly at first then quickly. The reaction was stirred over night without the addition of any more dry ice. The flask was opened and 200 mL of 2N HCl was quickly added. The reaction mixture was extracted and the aqueous was extracted with EtOAc and combined with the reaction organic layer, dried with MgSO$_4$, filtered through cotton, and concentrated in vacuo to yield 48.26 g of a crude yellow oil which was carried on to the next step without further purification.

Step 4: Synthesis of 2-(5-((1H-imidazol-1-yl)methyl) pyridin-2-yl)-N-(tert-butyl)-4-(trifluoromethoxy)benzenesulfonamide. The bromide product of Step 1 (1.35 g, 5.6 mmol) and the boronic acid product from Step 3 (7.6 g, 22.4 mmol, 4 eq) were combined in a 200 mL round bottom flask. Pd(PPh$_3$)$_4$ (1.3 g, 0.2 mmol, 1.12) was added to the flask under an atmosphere of N$_2$, the flask was placed under high vacuum, and 60 mL of toluene, 10 mL of EtOH, and 33 mL of a 1M aqueous NaOH. The reaction was stirred at 85° C. overnight and concentrated in vacuo. The residue was dissolved in EtOAc, extracted with brine, the organic layer was dried with MgSO$_4$, filtered through cotton, concentrated onto Celite®, and purified by automated chromatography to yield 670 mg (26% yield). $^1$H NMR (400 MHz, CD$_3$OD) d 8.61 (s, 1H), 8.25 (d, J=8.8 Hz, 1H), 7.81 (d, J=7.9 Hz, 1H), 7.68 (d, J=7.9 Hz, 1H), 7.56 (df, J=8.8, 2.4, 1.1 Hz, 1H), 7.45 (d, J=2.0 Hz, 1H), 5.42 (s, 2H), 1.22 (s, 9H). $^{13}$C NMR (101 MHz, CD$_3$OD) d 156.32, 151.07, 147.22, 140.70, 140.47, 136.58, 132.95, 130.94, 124.91, 123.91, 120.29 (q, J=257.6 Hz), 120.15, 54.33, 28.92. $^{19}$F NMR (376 MHz, CD$_3$OD) d −59.36. MS (ESI): m/z=455.0 [M+H]$^+$.

Step 5: Synthesis of 2-(5-((1H-imidazol-1-yl)methyl) pyridin-2-yl)-4-(trifluoromethoxy)benzenesulfonamide. The product of Step 4 (670 mg, 1.47 mmol) was refluxed overnight in 3 mL of TFA. The reaction was cooled to room temperature, neutralized with a saturated NaHCO$_3$ solution, extracted with EtOAc, dried with MgSO$_4$, filtered through cotton, dried on Celite®, and purified by automated chromatography with a 0% to 8% gradient of MeOH in DCM to yield 271 mg of the desired product (46% yield). $^1$H NMR (400 MHz, CD$_3$OD) d 8.59 (s, 1H), 8.25 (d, J=8.7 Hz, 1H), 7.85 (s, 1H), 7.79 (dd, J=8.0, 1.5 Hz, 1H), 7.62 (d, J=8.1 Hz, 1H), 7.54 (d, J=8.7 Hz, 1H), 7.47 (s, 1H), 7.23 (s, 1H), 7.06 (s, 1H), 5.37 (s, 2H). $^{13}$C NMR (101 MHz, CD$_3$OD) d 157.93, 152.57, 152.55, 148.69, 141.91, 141.50, 138.13, 134.20, 131.89, 125.63, 125.14, 121.71 (q, J=515.7, 257.8 Hz), 121.66, 48.66. $^{19}$F NMR (376 MHz, CD$_3$OD) d −59.28. MS (ESI): m/z=399.0 [M+H]$^+$.

Step 6: Synthesis of butyl(2-(5-((1H-imidazol-1-yl) methyl)pyridin-2-yl)-4-(trifluoromethoxy)phenyl)sulfonylcarbamate. To a stirring solution of the product from Step 5 (271 mg, 0.68 mmol) and 4-(dimethylamino)pyridine (91 mg, 0.75 mmol, 1.1 eq) in 10 mL of pyridine was added butyl chloroformate (1.76 mL, 13.6 mmol, 20 eq). The reaction was stirred at room temperature overnight, and concentrated in vacuo. The residue was dissolved in 20 mL of a 10% citric acid solution and EtOAc. The organic layer was extracted three times with EtOAc and dried with MgSO$_4$, filtered through cotton, concentrated onto Celite®, and purified by automated chromatography with a 0% to 20% gradient of MeOH in DCM to yield 289 mg of a white foam (58% yield). $^1$H NMR (400 MHz, CD$_3$OD) d 8.60 (s, 1H), 8.32 (d, J=8.8 Hz, 1H), 7.84 (d, J=7.4 Hz, 1H), 7.71 (d, J=8.0 Hz, 1H), 7.62-7.53 (m, 1H), 7.46 (s, 1H), 7.36 (d, J=1.6 Hz, 1H), 7.30 (s, 1H), 5.49 (s, 2H), 3.98 (t, J=6.5 Hz, 2H), 1.58-1.44 (m, 2H), 1.30 (dt, J=15.2, 7.3 Hz, 3H), 0.98-0.83 (m, 3H). $^{19}$F NMR (376 MHz, CDCl$_3$) d −55.37. MS (ESI): m/z=499.0 [M+H]$^+$.

Example 3

Synthesis of Exemplary Compound 8 (butyl(2-(5-((3-methyl-2-oxoimidazolidin-1-yl)methyl)pyridin-2-yl)-4-(trifluoromethoxy)phenyl) sulfonylcarbamate).

Step 1: Synthesis of 5-((1H-imidazol-1-yl)methyl)-2-bromopyridine. The starting material 2-bromo-5-(bromomethyl)pyridine was synthesized according to a published protocol (*Tetr. Lett.* 2002, 43, 1697). To a 50 mL round bottom flask containing 1-methyl-2-imidazolidinone (250 mg, 2.5 mmol) and NaH 60% dispersion in mineral oil (110 mg, 2.75 mmol, 1.1 eq) at 0° C. was added 3 mL of DriSolv® DMF. The reaction turned into a cloudy white solid, then warmed to room temperature, and stirred for an hour. 2-bromo-5-(bromomethyl)pyridine (750 mg, 1.2 mmol, 3 eq) was dissolved in 1 mL of DriSolv® DMF and the reaction was stirred overnight at room temperature. The reaction was concentrated in vacuo, dissolved in EtOAc and a saturated solution of NH$_4$Cl, and extracted. The organic layer was concentrated in vacuo, and purified by automated chromatography to yield 173 mg (26%) of a light brown oil R$_f$=0.15 in 75% EtOAc in hexanes/1% MeOH). $^1$H NMR (600 MHz, CD$_3$OD) d 8.26 (d, J=2.4 Hz, 1H), 7.62 (dd, J=8.2, 2.5 Hz, 1H), 7.56 (d, J=8.2 Hz, 1H), 4.33 (s, 2H), 3.36-3.31 (m, 2H), 3.28-3.23 (m, 2H), 2.77 (s, 3H). $^{13}$C NMR (151 MHz, CD$_3$OD) d 150.70, 141.72, 140.28, 134.46, 129.45, 45.97, 45.95, 43.46, 31.40.

Step 2: Synthesis of N-(tert-butyl)-2-(5-((3-methyl-2-oxoimidazolidin-1-yl)methyl)pyridin-2-yl)-4-(trifluoromethoxy)benzenesulfonamide. The bromide product of Step 1 (173 mg, 0.64 mmol) and the boronic acid product from Step 2 of Example 2 (874 mg, 2.54 mmol, 4 eq) were combined in a round bottom flask. Pd(PPh$_3$)$_4$ (462 mg, 0.4 mmol, 0.63 eq) was added to the flask under an atmosphere of N$_2$, the flask was placed under high vacuum, and 20 mL of toluene, 5 mL of EtOH, and 3.84 mL of a 1N aqueous NaOH. The reaction was stirred at 90° C. for 2 days, concentrated in vacuo, dissolved in EtOAc and H$_2$O, and extracted. The organic layer was washed with brine, filtered through Celite®, concentrated onto Celite®, and purified by automated chromatography to yield 232 mg (75%) of a tan oil R$_f$=0.25 in 80% EtOAc in hexanes with 1% MeOH). $^1$H NMR (400 MHz, CD$_3$OD) d 8.46 (d, J=2.4 Hz, 1H), 8.12 (d, J=8.7 Hz, 1H), 7.74 (dd, J=8.2, 2.3 Hz, 1H), 7.53 (d, J=8.1

Hz, 1H), 7.46-7.37 (m, 1H), 7.33 (d, J=2.6 Hz, 1H), 4.34 (s, 2H), 3.33-3.13 (m, 4H), 2.69 (s, 3H), 1.09 (s, 9H). $^{19}$F NMR (376 MHz, CD$_3$OD) d −59.16. MS (ESI): m/z=487.0 [M+H]$^+$.

Step 3: Synthesis of 2-(5-((3-methyl-2-oxoimidazolidin-1-yl)methyl)-pyridin-2-yl)-4-(trifluoromethoxy)benzenesulfonamide. The product of Step 2 (232 mg, 0.47 mmol) was stirred for 2 days at room temperature in 10 mL of TFA. The reaction was neutralized with a saturated NaHCO$_3$ solution, extracted with EtOAc, dried and purified by automated chromatography with a 0% to 2.8% gradient of MeOH in DCM to yield 121.4 mg (60%) of an off-white powder. $^1$H NMR (400 MHz, CD$_3$OD) d 9.16 (d, J=2.2 Hz, 1H), 8.78 (d, J=8.7 Hz, 1H), 8.45 (dd, J=8.1, 2.2 Hz, 1H), 8.20 (dd, J=8.1, 0.9 Hz, 1H), 8.12 (ddd, J=8.8, 2.5, 1.2 Hz, 1H), 8.07 (d, J=2.5 Hz, 1H), 5.02 (s, 2H), 3.98-3.84 (m, 4H), 3.34 (s, 3H). $^{19}$F NMR (376 MHz, CD$_3$OD) d −57.66.

Step 4: Synthesis of butyl((2-(5-((3-methyl-2-oxoimidazolidin-1-yl)methyl)pyridin-2-yl)-4-(trifluoromethoxy)phenyl)sulfonyl)carbamate.

Prepared similarly to Step 6 of Example 2. $^1$H NMR (400 MHz, CD$_3$OD) d 8.43 (dd, J=2.3, 0.9 Hz, 1H), 8.23 (d, J=8.9 Hz, 1H), 7.73 (dd, J=8.0, 2.2 Hz, 1H), 7.54-7.44 (m, 2H), 7.30-7.24 (m, 1H), 4.37 (s, 2H), 3.92 (t, J=6.5 Hz, 2H), 3.33-3.23 (m, 4H), 2.72 (s, 3H), 1.48-1.37 (m, 2H), 1.26-1.15 (m, 2H), 0.80 (t, J=7.4 Hz, 3H). $^{19}$F NMR (376 MHz, CD$_3$OD) d −59.29. MS (ESI): m/z=531.0 [M+H]$^+$.

Example 4

Synthesis of Compound 9 (butyl(2-(5-(morpholinomethyl)pyridin-2-yl)-4-(trifluoromethoxy)phenyl)sulfonylcarbamate), and compound 10 (butyl(2-(5-((4-methylpiperazin-1-yl)methyl)pyridin-2-yl)-4-(trifluoromethoxy)phenyl)sulfonylcarbamate)

Step 1: Synthesis of N-(tert-butyl)-2-(5-methylpyridin-2-yl)-4-(trifluoromethoxy)benzenesulfonamide. 2-Bromo-5-methylpyridine (1.23 mg, 7.15 mmol) and the boronic acid product from Step 2 of Example 2 (4.9 g, 14.3 mmol, 2 eq) were combined in a round bottom flask. Pd(PPh$_3$)$_4$ (1.65 g, 1.43 mmol, 0.2 eq) was added to the flask under an atmosphere of N$_2$, the flask was placed under high vacuum, and 100 mL of toluene, 20 mL of EtOAc, and 42 mL of a 1N aqueous NaOH. The reaction was stirred at 90° C. for 2 days, concentrated in vacuo, dissolved in EtOAc and H$_2$O, and extracted. The organic layer was washed with NaHCO$_3$, dried with MgSO$_4$, filtered, concentrated onto Celite®, and purified by automated chromatography with a 5% to 40% gradient of EtOAc in hexanes to yield 3.027 g (R$_f$=0.3 in 20% EtOAc in hexanes). $^1$H NMR (400 MHz, CDCl$_3$) δ 8.15 (dt, J=2.3, 0.8 Hz, 1H), 7.95 (d, J=8.7 Hz, 1H), 7.69-7.64 (m, 1H), 7.38 (ddd, J=8.0, 2.3, 0.9 Hz, 1H), 7.12 (dd, J=8.0, 0.8 Hz, 1H), 7.06 (ddd, J=8.7, 2.5, 1.2 Hz, 1H), 2.08 (d, J=1.0 Hz, 3H), 1.04 (s, 9H). $^{19}$F NMR (376 MHz, CDCl$_3$) δ −57.76. MS (ESI): m/z: [M+H]$^+$ calculated 389.11. found 389.0. MS (ESI): m/z=389.0 [M+H]$^+$.

Step 2: Synthesis of 2-(5-(bromomethyl)pyridin-2-yl)-N-(tert-butyl)-4-(trifluoromethoxy)benzenesulfonamide. A solution of the product of Step 1 (3.027 g, 7.8 mmol) and N-bromosuccinimide (1.526 g, 8.6 mmol, 1.1 eq) in 100 mL of DCM and 100 mL of H$_2$O was stirred under UV irradiation at 80-90° C. in a round bottom flask outfitted with a reflux condenser for 48 hours. The reaction was then cooled to room temperature, poured into a separatory funnel, and extracted. The organic layers were dried with MgSO$_4$, filtered through cotton, concentrated onto Celite®, and flushed through an silica gel column via automated chromatography with a 5% to 40% gradient of EtOAc in hexanes to yield 517 mg of a crude mixture that was carried on to the next step without further purification. MS (ESI): m/z: 466.9 [M+H]$^+$.

Step 3: Synthesis of N-(tert-butyl)-2-(5-(morpholinomethyl)pyridin-2-yl)-4-(trifluoromethoxy)benzenesulfonamide. To a stirring solution of the product of Step 2 (186 mg, 0.4 mmol) in 3 mL of DMF was added morpholine (0.104 mL, 1.19 mmol, 3 eq) and K$_2$CO$_3$ (329 mg, 2.39 mmol, 6 eq) and stirred at room temperature for 2 days. The reaction was concentrated in vacuo onto Celite and purified by automated chromatography with a gradient 0% to 100% EtOAc in hexanes to yield 67 mg of a clear film (35% yield, R$_f$=0.3 in 50% EtOAc in hexanes). $^1$H NMR (400 MHz, CD$_3$OD) d 8.63 (d, J=1.5 Hz, 1H), 8.27 (d, J=8.8 Hz, 1H), 7.97 (dd, J=8.1, 2.2 Hz, 1H), 7.67 (dd, J=8.0, 0.7 Hz, 1H), 7.56 (ddd, J=8.8, 2.5, 1.2 Hz, 1H), 7.47 (dd, J=2.4, 0.7 Hz, 1H), 3.78-3.70 (m, 4H), 3.66 (s, 2H), 2.59-2.50 (m, 4H), 1.25 (s, 9H). $^{19}$F NMR (376 MHz, CD$_3$OD) d −59.27. MS (ESI): m/z: 474.0 [M+H]$^+$.

Step 4: Synthesis of butyl((2-(5-(morpholinomethyl)pyridin-2-yl)-4-(trifluoromethoxy)phenyl)sulfonyl)carbamate. The product of Step 3 (67 mg, 0.14 mmol) was stirred for 2 days at room temperature in 10 mL of TFA. The reaction was stirred at room temperature for 2 days, concentrated in vacuo, and dissolved in MeOH and concentrated in vacuo 3 times. To the resulting crude product was added 4-(dimethylamino)pyridine (48.8 mg, 0.4 mmol, 2.85 eq), butyl chloroformate (0.361 mL, 2.8 mmol, 20 eq), and 5 mL of pyridine. The reaction was stirred at room temperature for 2 days and concentrated in vacuo. To the residue was 300 mg of citric acid then EtOAc and H$_2$O. The organic layer was extracted three times with EtOAc and dried with MgSO4, filtered through cotton, concentrated onto Celite®, and purified by automated chromatography to yield 44.5 mg the pure product (61% yield). $^1$H NMR (400 MHz, CD$_3$OD) d 8.57 (s, 1H), 8.31 (d, J=8.8 Hz, 1H), 7.90 (d, J=7.8 Hz, 1H), 7.75 (d, J=8.0 Hz, 1H), 7.59-7.48 (m, 1H), 7.34 (d, J=2.6 Hz, 1H), 3.92 (t, J=6.5 Hz, 2H), 3.81-3.71 (m, 4H), 2.71-2.61 (m, 4H), 1.51 (dd, J=8.9, 5.8 Hz, 2H), 1.32 (dt, J=11.3, 3.7 Hz, 2H), 0.91 (t, J=7.3 Hz, 3H). $^{19}$F NMR (376 MHz, CD$_3$OD) d −59.27. MS (ESI): m/z: 518.0 [M+H]$^+$.

Step 5: Synthesis of N-(tert-butyl)-2-(5-((4-methylpiperazin-1-yl)methyl)pyridin-2-yl)-4-(trifluoromethoxy)benzenesulfonamide. To a stirring solution of the product of Step 2 (136 mg, 0.29 mmol) in 3 mL of DMF was added 1-methylpiperazine (98.6 µL, 0.87 mmol, 3 eq) and K$_2$CO$_3$ (240 mg, 1.74 mmol, 6 eq) and stirred at room temperature for 2 days. The reaction was concentrated in vacuo onto Celite and purified by automated chromatography with a gradient 0% to 20% MeOH in DCM to yield 41 mg of a clear film (29% yield, R$_f$=0.2 in 10% MeOH in DCM). $^1$H NMR (400 MHz, CD$_3$OD) d 8.61 (d, J=1.6 Hz, 1H), 8.26 (d, J=8.8 Hz, 1H), 7.95 (dd, J=8.1, 2.2 Hz, 1H), 7.66 (dd, J=8.1, 0.6 Hz, 1H), 7.56 (ddd, J=8.8, 2.5, 1.2 Hz, 1H), 7.46 (d, J=1.8 Hz, 1H), 3.68 (s, 2H), 2.58 (s, 8H), 2.34 (s, 3H), 1.24 (s, 9H). $^{19}$F NMR (376 MHz, CD$_3$OD) d −59.32. MS (ESI): m/z: 487.2 [M+H]$^+$.

Step 6: Synthesis of butyl((2-(5-((4-methylpiperazin-1-yl)methyl)pyridin-2-yl)-4-(trifluoromethoxy)phenyl)sulfonyl)carbamate. The product of Step 6 (41 mg, 0.07 mmol) was stirred for 2 days at room temperature in 4.5 mL of TFA. The reaction was stirred at room temperature for 2 days, concentrated in vacuo, and dissolved in MeOH and concentrated in vacuo 2 times. To the resulting crude product was added 4-(dimethylamino)pyridine (9 mg, 0.14 mmol, 1 eq), butyl chloroformate (0.191 mL, 1.48 mmol, 20 eq), and pyridine. The reaction was stirred at room temperature for 2 days and concentrated in vacuo. To the residue was 300 mg of citric acid then EtOAc and H₂O. The organic layer was extracted three times with EtOAc and dried with MgSO4, filtered through cotton, concentrated onto Celite®, and purified by automated chromatography to yield 44 mgs of an off-white foam (quantitative, $R_f$=0.1 in 20% MeOH in DCM). $^1$H NMR (400 MHz, CD₃OD) d 8.58 (s, 1H), 8.27 (d, J=8.8 Hz, 1H), 7.91 (s, 1H), 7.63-7.49 (m, 2H), 7.33 (d, J=3.1 Hz, 1H), 3.97 (t, J=6.4 Hz, 2H), 3.75 (s, 2H), 2.81 (p, J=15.8, 15.2 Hz, 19H), 1.47 (q, J=6.9 Hz, 2H), 1.27 (dq, J=14.8, 7.5, 6.8 Hz, 4H), 0.85 (t, J=7.3 Hz, 3H). $^{19}$F NMR (376 MHz, CD₃OD) d −59.25. MS (ESI): m/z: 531.1 [M+H]⁺.

Example 5

Synthesis of Exemplary Compound 11 (butyl(2-(5-((1H-imidazol-1-yl)methyl)thiazol-2-yl)-4-(trifluoromethoxy) phenyl)sulfonylcarbamate)

Step 1: Synthesis of 2-bromo-5-(bromomethyl)thiazole. A solution of 2-bromo-5-methylthiazole (1 g, 5.6 mmol) and N-bromosuccinimide (1.1 g, 6.18 mmol, 1.1 eq) in 40 mL of DCM and 40 mL of H₂O was stirred under UV irradiation at 90° C. in a round bottom flask outfitted with a reflux condenser for 3 hours. The reaction was then cooled to room temperature, poured into a separatory funnel, and extracted. The aqueous layer was extracted twice more with DCM, the organic layers combined, dried with MgSO₄, filtered through cotton, concentrated and purified by automated chromatography with a 0% to 3% gradient of EtOAc in hexanes to yield 1.24 g (78%). $^1$H NMR (400 MHz, CDCl₃) d 7.46 (d, J=0.9 Hz, 1H), 4.57 (d, J=0.9 Hz, 3H). $^{13}$C NMR (101 MHz, CDCl₃) d 141.92, 139.80, 137.39, 22.37. MS (ESI): m/z: 255.8 [M+H]⁺.

Step 2: Synthesis of 5-((1H-imidazol-1-yl)methyl)-2-bromothiazole. To a stirring solution of the product of Step 1 (765 mg, 2.98 mmol) in 20 mL of DMSO was added imidazole (202 mg, 2.98 mmol, 1 eq) and K₂CO₃ (1.23 g, 8.94 mmol, 3 eq) and stirred overnight. The reaction was extracted with brine and EtOAc and concentrated in vacuo, and purified by automated chromatography to yield 306.6 nag (42%) of the desired product. MS (ESI): m/z: 243.9 [M+H]⁺.

Step 3: Synthesis of 2-(5-((1H-imidazol-1-yl)methyl)thiazol-2-yl)-N-(tert-butyl)-4-(trifluoromethoxy)benzenesulfonamide. The bromide product of Step 2 (306.6 nag, 1.26 mmol) and the boronic acid product from Step 2 of Example 2 (1.29 g, 3.78 mmol, 3 eq) were combined in a round bottom flask. Pd(PPh₃)₄ (290 mg, 0.25 mmol, 0.2 eq) was added to the flask under an atmosphere of N₂, the flask was placed under high vacuum, and 10 mL of toluene, 3 mL of EtOH, and 1.26 mL of a 2M aqueous Na₂CO₃. The reaction was stirred at 90° C. for 2 days, filtered through Celite©, concentrated onto Celite®, and purified by automated chromatography to yield 157 mg of a brown oil (27% yield, $R_f$=0.30 in 5% MeOH in DCM).

Step 4: Synthesis of 2-(5-((1H-imidazol-1-yl)methyl)thiazol-2-yl)-4-(trifluoromethoxy)benzenesulfonamide. The product of Step 3 (157 mg, 0.34 mmol) was stirred for 2 days at room temperature in 10 mL of TFA. The reaction was neutralized with a saturated NaHCO₃ solution, extracted with EtOAc, dried on Celite®, and purified by automated chromatography with a 0% to 10% gradient of MeOH in DCM to yield 107 mg of an off-white powder (78% yield). MS (ESI): m/z: 404.9 [M+H]⁺.

Step 5: Synthesis of butyl((2-(5-((1H-imidazol-1-yl) methyl)thiazol-2-yl)-4-(trifluoromethoxy)phenyl)sulfonyl) carbamate. To a stirring solution of the product from Step 4 (64.6 mg, 0.16 mmol) and 4-(dimethylamino)pyridine (19.5 mg, 0.16 mmol, 1 eq) in 3 mL of pyridine was added butyl chloroformate (0.407 mL, 3.2 mmol, 20 eq). The reaction was stirred at room temperature for 2 days and concentrated in vacuo. To the residue was 300 mg of citric acid then EtOAc and H₂O. The organic layer was extracted three times with EtOAc and dried with MgSO4, filtered through cotton, concentrated onto Celite®, and purified by automated chromatography with a 0% to 20% gradient of MeOH in DCM to yield 40.7 mg (50% yield). $^1$H NMR (600 MHz, CD₃OD) d 8.46 (s, 1H), 8.22 (d, J=8.8 Hz, 1H), 7.87 (s, 1H), 7.56-7.34 (m, 3H), 7.26 (s, 1H), 5.61 (s, 2H), 3.84 (t, J=6.5 Hz, 2H), 1.46-1.32 (m, 2H), 1.25-1.09 (m, 2H), 0.76 (t, J=7.4 Hz, 3H). $^{19}$F NMR (564 MHz, CD₃OD) d −59.35. MS (ESI): m/z=504.9 [M+H]⁺ MS (ESI): m/z: 505.0 [M+H]⁺.

Example 6

Inability of Exemplary Compound 7 to Compete with Ang II on Angiotensin Receptors AT1R and AT2R Compound 7 was evaluated in vitro for its ability to compete with radiolabeled Ang II or analogs in a displacement assay for AT1R and AT2R receptors. The results, showed that compound 7 had very weak activity at the AT1 receptor, displacing Ang II with an EC50 greater than 10 μM, suggesting that compound 7 is not an effective agonist or antagonist of AT1R. In the same AT1R assay, a compound similar to 7, wherein the pyridine ring was replaced by a benzene ring had a similar activity, replacing Ang II with an EC50 greater than 10 μM. In the AT2R displacement assay compound 7 displaced Ang II with an EC50 greater than 10 μM, suggesting that it is not an effective agonist or antagonist of AT2R. In the same AT2R assay, a compound similar to 7, wherein the pyridine ring was replaced by a benzene ring was able to replace Ang II with an EC50 lower than 0.5 μM.

These results point to the inherent selectivity of exemplary compound 7 and indicate that compound 7 at submicromolar concentrations does not bind effectively to either AT1R or AT2R and therefore is not an effective agonist or antagonist of these receptors. These results also indicate that the overall design of exemplary compound 7 does not allow compounds of this type to effectively bind to AT1R, while the presence of a basic nitrogen in the middle aromatic ring (e.g. pyridine) significantly reduces the ability of the compound to bind to AT2R.

Example 7

Activity of Exemplary Compounds 7, 8, 9, 10, and 11 in a Competition Binding Assay Involving the Displacement of Fluorescent Ang(1-7)

CHO cells stably transfected with recombinant Human mast proto-oncogen driven by the human cytomegalovirus were grown to 80% confluency. The cells were detached with trypsin and harvested by centrifugation. Cells were washed three times in progressively colder buffers. The final number of cells per assay was 5×10⁵. All subsequent steps were performed on ice. Test compound was added to the cells for 10 minutes prior to addition of fluorescently labeled A(1-7). After 10 minutes further incubation, the cells were washed to remove unbound A(1-7) and the fluorescence bound was read at an excitation of 490 nm and an emission of 520 nm.

In this binding assay, exemplary compounds 7, 8, 9, 10, and 11 were able to displace fluorescent Ang(1-7) as follows:

| Compound | % Displacement |
| --- | --- |
| Compound 7 | 28.1% |
| Compound 8 | 18.6% |
| Compound 9 | 17.3% |
| Compound 10 | 22.0% |
| Compound 11 | 23.0% |

These results indicate that exemplary compounds 7, 8, 9, 10, and 11 are able to effectively displace Ang(1-7) from Mas receptor with variable efficiency, suggesting that the provided compounds behave as mimics of Ang(1-7) that is able to bind onto Mas receptor. Taken together, the results from Examples 6 and 7, indicate that the provided compounds are able to selectively bind to the receptor of Ang(1-7) but not to the receptors of Ang II, i.e. AT1R or AT2R.

Example 8

Activity of Exemplary Compound 7 Involving the Mas Receptor

Transfected cells that express Mas were used to identify and evaluate provided compounds as Mas agonists, by promoting NO production as readouts. CHO cells stably transfected with pTEJ-8 vector containing recombinant Human Mas1 clone were grown to confluency. Cells were washed three times for 30/5/5 minutes with prewarmed (37° C.) Tyrodes Salts (supplemented with 1 g/L NaHCO$_3$, and 1.9 g/L d-Glucose). Cells were incubated for a short time in 700 µL of supplemented Tyrodes salts containing 10 µM PTIO, 100 µM DAN, and 1 mM L-arginine. When using antagonist for competition assays, cells were exposed to the inhibitor at $1 \times 10^{-7}$ M for 15 minutes, before additional drugs are added.

Chemicals ($10^{-8}$ to $10^{-6}$ M or the maximum concentration found not to cause cytotoxicity) to be screened were added to the cell medium and the plates were agitated for 1 minute before being placed into the incubator for 2 hours. After 2 hours, cellular supernatants were transferred to opaque 96 well plates, and the fluorescence intensity was recorded at an ex/em of 380/425.

Compound 7 was found to be a potent and selective agonist of Mas, where its ability to enhance NO production was shown to be similar to that of A(1-7) (FIG. 4). In this assay, the EC50 was found to be 10 nM. To confirm that Compound 7 is a selective Mas agonist, co-administration of A779, a selective Mas antagonist, was able to reduce NO production back to baseline.

Example 9

Activity of Exemplary Compound 7 Reduces Blood Glucose in Diabetes

Mice homozygous for the diabetes spontaneous mutation Lepr$^{db}$ (BKS.Cg-Dock7$^m$+/+Lepr$^{db}$/J), which is an obese model of type 2 diabetes as a consequence of truncation of the leptin receptor, have verified plasma glucose levels >500 mg/dL prior to initiation of treatment. Food and water were available ad libitum, and all mice were kept on a 12-hour light/dark cycle. BKS.Cg-Dock7$^m$+/+Lepr$^{db}$/J mice and their heterozygous controls (n=6/group) were administered either saline (control), Ang-(1-7) (500 mcg/kg/day), or Compound 7 500 mcg/kg/day for two weeks by subcutaneous (SC) injection. Mice were fasted overnight prior to assessment of plasma glucose levels. Blood was taken from the saphenous vein and tested for glucose levels by a glucometer.

In this model, Compound 7 treated group revealed that fasting blood glucose (FBG) measured at the end of the study was significantly lower (p<0.05) than db/db mice treated with saline (FIG. 5). The glucose of Compound 7 treated mice were statistically significantly lower than either db/db controls or db/db-treated with Ang(1-7). Compound 7 was able to reduce peripheral glucose >40% of levels found in vehicle or A(1-7) treated mice. In terms of the excess blood glucose over non-diabetic controls, Compound 7 was able to reduce FBG by 72%.

Example 10

Activity of Exemplary Compound 7 Involving Preventing Organmegaly in Diabetes and Metabolic Syndrome Compound 7 (500 mcg/kg/day) or Ang(1-7) (500 mcg/kg/day) treated db/db mice were euphanized after 14 days of treatment. At necropsy, organs were collected for histology and weights. In FIG. 6A to 6C, hearts, left and right kidney normalized to tibia length were weight where db/db treated with Compound 7 were lower than db/db-controls (saline) and db/db treated with Ang(1-7). In this model, Compound 7 prevented the development of cardiomegaly (A) and left kidney hypertrophy (B), where the difference between db/db controls was statistically significant (p<0.05).

Example 11

Activity of Exemplary Compound 7 is Able to Prevent Fat Accumulation in the Liver of Diabetic Mice The lipid levels found in the liver was evaluated in db/db animals treated for 14 days with vehicle, 500 mcg/kg/day Ang(1-7) or Compound 7. Livers isolated from mice were harvested. Liver tissue sections were washed with cold saline and frozen in the presence of optimum cutting temperature (OCT) formulation. Tissues were then cut into 10-µm sections using a cryostat. Oil Red O staining and H&E staining were performed according to published procedures (Yang et al., 2013). The tissues were observed and images acquired using a light microscope (Olympus BX51) (FIG. 6). Compound 7 (FIG. 6 right panel) reduced Oil Red staining (red droplets reflect lipid deposition) compared with db/db controls (FIG. 6 left panel).

Example 12

Activity of Exemplary Compound 7 is Able to Enhance Bone Marrow Progenitor Cells Proliferation The femurs and tibia were collected from db/db mice treated 500 mcg/kg/day Ang(1-7) or Compound 7 subcutaneously for 14 days were euphanized and the bone marrow were collected by flushing with PBS containing 2% fetal calf serum. After collection of the bone marrow, the red blood cells will be lysed with a hypotonic solution (described above), mixed with 0.04% trypan blue and the number of nucleated cells was assessed by hematocytometer under light microscopy. Aliquots of cells were then resuspended at $1 \times 10^6$ cells/ml (GM and GEMM, bone marrow), $1.5 \times 10^6$ cells/ml (BFU-E, bone marrow). One hundred µl of each suspension was added to 900 µl of semisolid medium containing 0.9% methyl cellulose in Iscove's MDM, 15% fetal calf serum, 1% bovine serum albumin, 10 µg/ml bovine pancreatic insulin, 200 μg/ml human transferrin, 10⁻⁴ M 2-mercaptoethanol, 2 mM glutamine, 10 ng/ml recombinant murine interleukin 3, 10 ng/ml recombinant human interleukin 6, 50 ng/ml recombinant murine stem cell factor and 3 units/ml erthropoietin. This mixture was then added to duplicate wells of a 24 well plate. The cultures were then placed at 37° C. in a humidified atmosphere of 5% $CO_2$ in air. At day 14, the number of progenitor colonies formed was enumerated under phase contrast microscopy.

The bone marrow cells were also cultured to assess the number of MSCs by a CFU-F assay. $2.5 \times 10^5$ cells/ml, 2 ml per well, were diluted into Mesencult medium (Stem Cell Technologies, Vancouver, BC, Canada) and 2 mL were placed in each well of a 24 well plate. The cultures were then incubated at 37° C. in a humidified atmosphere of 5% $CO_2$ in air. At days 2, 5 and 8, the number of progenitor colonies formed was enumerated under phase contrast microscopy.

Figure 8:
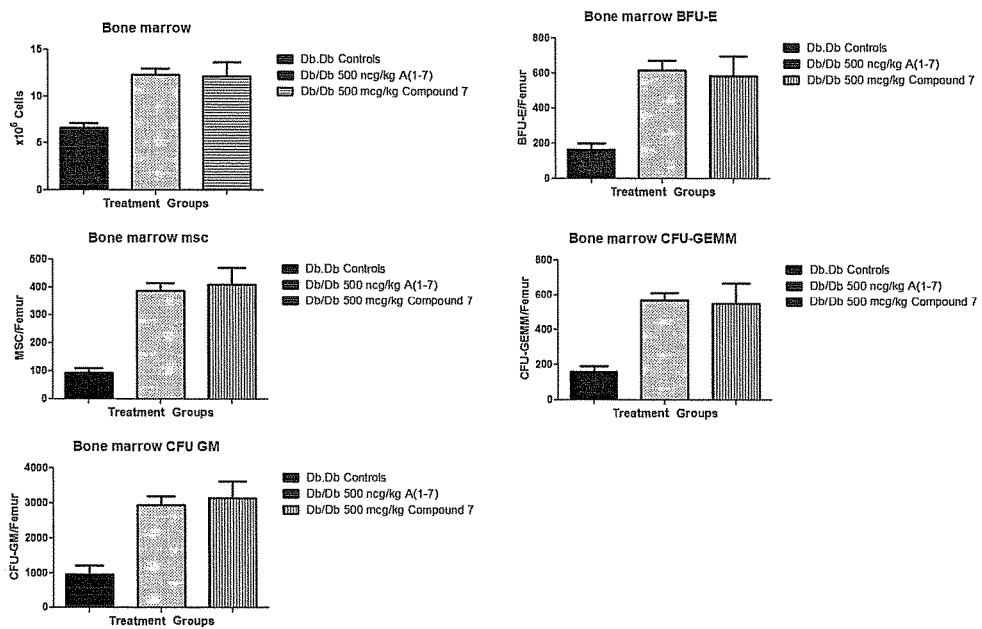
FIG. 8: Diabetes causes a reduction in the health of the bone marrow, the source of a number of progenitors that participate in healing, particularly blood cells (red cells, platelets and leukocytes). Treatment with both Ang(1-7) and compound 7 increased the bone marrow counts is (A). Additionally Compound 7 was comparable to Ang(1-7) in the increase in bone marrow cell number as well as early progenitors (CFU-GEMM), myeloid progenitors (CFU-GM), erythroid progenitors (BFU-E) and mesenchymal stem cells (MSC) (B-E).

Diabetes causes a reduction in the health of the bone marrow, the source of a number of progenitors that participate in healing, particularly blood cells (red cells, platelets and leukocytes). Treatment with both Ang(1-7) and Compound 7 was able to increase bone marrow counts. Compound 7 was comparable to Ang(1-7) with regards to increasing in bone marrow cell number as well as early progenitors (CFU-GEMM), myeloid progenitors (CFU-GM), erythroid progenitors (BFU-E) and mesenchymal stem cells (MSC) (FIG. 8).

Example 13

Activity of Exemplary Compound 7 in Antitumor Activity

Figure 9:
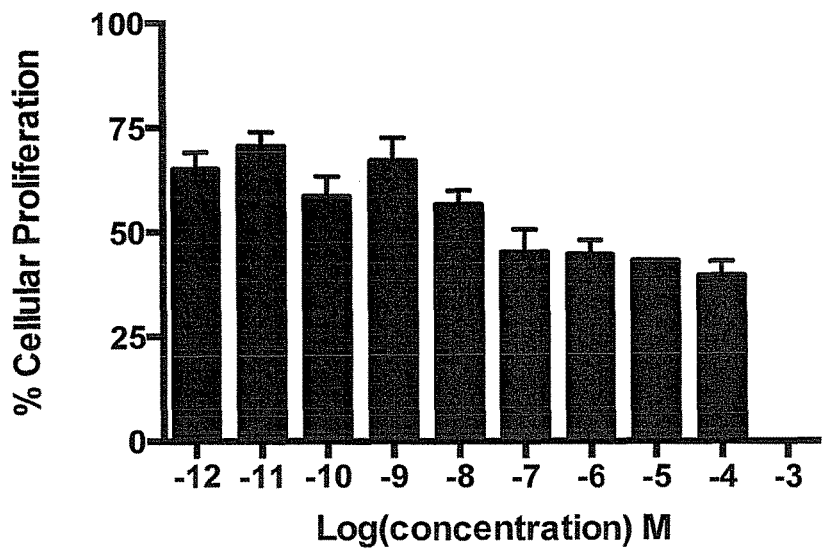
FIG. 9: The effect of compound 7 on tumor cell proliferation was evaluated using MDA MB 231 in a concentration escalation design. Compound 7 did not increase proliferation of MDA MB 231 breast cancer cell line. Rather compound 7 inhibited tumor proliferation with an IC50 calculated to be 58 µM.

Compound 7 was evaluated for its ability to modulate cancer proliferation using MDA MB 231 breast cancer cell line. MDA MB 231 was treated with increasing concentration of Compound 7 ranged from $1 \times 10^{-12}$ to $1 \times 10^{-3}$ M, where the cells were incubated for 48 hours. After the incubation, cellular viability was evaluated using 3-(4,5-dimethylthiazol-2-yl)-2,5-diphenyltetrazolium bromide or MTT, where viable cells are able to reduce MTT to formazan and form an insoluble crystal. The solubilized crystal can be spectrometrically determine, where cellular viability is compared to cells treated with vehicle. The cellular viability of MDA MB 231 is summarized (FIG. 9). The addition of Compound 7, a potential Mas agonist, did not increase breast cancer cell proliferation and thus does not enhance tumor proliferation. Rather at $1 \times 10^{-12}$ M (1 pmole) of Compound 7, the cellular proliferation was only 70% of vehicle treated. Additionally, MDA MB 231 viability decreased in a concentration dependent manner, where the IC50 was established at $5.82 \times 10^{-8}$ M (58 μM) when using a Hill-slope analysis.

Example 14

Figure 10:
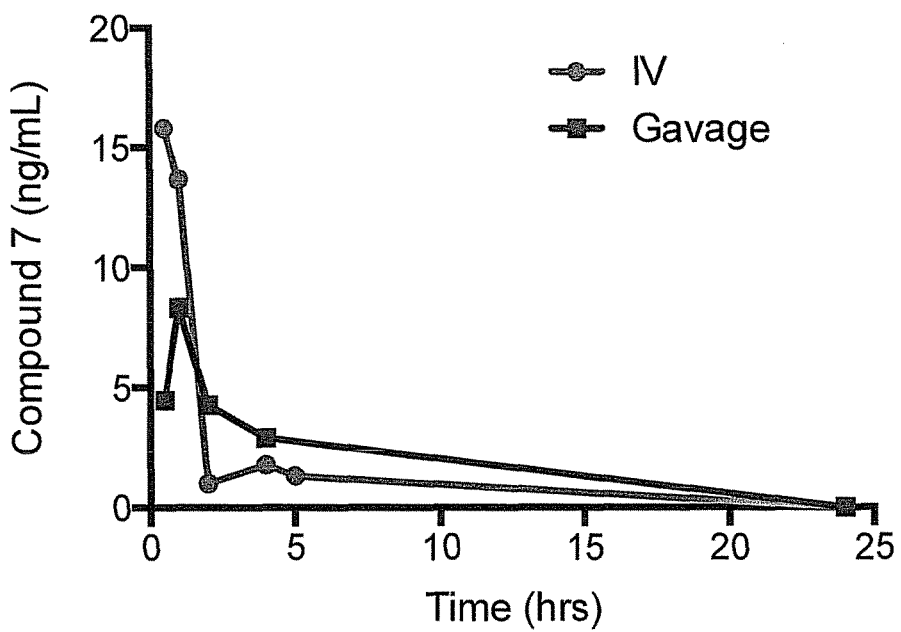
FIG. 10: The uptake and distribution of intravenous of compound 7 was measured in the blood of C57Bl/6 mice. Animals were euthanized at various time points after administration of compound 7 and blood collected and processed to plasma. Concentrations of compound 7 were measured by LC-MS/MS methodology. The oral bioavailability of compound 7 was 30%.

Compound 7 was evaluated for oral bioavailability at 500 μg/kg in C57Bl/6 mice. The drug was given by intravenous injection or by oral gavage and blood was collected at 0.5, 1, 2, 4, 8, 24 hours into heparinized tubes. The level of drug in the blood was measured by liquid chromatograph-mass spectrometry. Bioavailability was determined using the following ratio $AUC_{IG}/AUC_{IV}$ (FIG. 10). These pharmacokinetics studies showed that Compound 7 has a 30% bioavailability after oral gavage and can be formulated to further enhance its bioavailability.

Example 15

Compound 7 was evaluated for acute toxicity at 500 μg/kg in C57Bl/6 mice that was given as either a subcutaneous or intravenous injection, and its safety was evaluated for 7 days after treatment. No overt signs of toxicity, no gross lesions or changes in organ weight or hematology were seen in this range finding study

REFERENCES

Albrecht, D. (2007). Angiotensin-(1-7)-induced plasticity changes in the lateral amygdala are mediated by COX-2 and NO. *Learning & Memory*, 14(3), 177-184.

Balingit P P, Armstrong D G, Reyzelman A M, Bolton L, Verco S J, Rodgers K E, Nigh K A, diZerega G S. NorLeu3-A(1-7) stimulation of diabetic foot ulcer healing: results of a randomized, parallel-group, double-blind, placebo-controlled phase 2 clinical trial. Wound Repair Regen. 2012 July-August; 20(4):482-90. doi: 10.1111

Benter I F, Yousif M H, Anim J T, Cojocel C, Diz D I (2006) Angiotensin-(1-7) prevents development of severe hypertension and end-organ damage in spontaneously hypertensive rats treated with L-NAME. *Am J Physiol Heart Circ Physiol* 290(2):H684-H691.

Benter I F, Yousif M H, Cojocel C, AL-Maghrebi M, Diz D I (2007) Angiotensin-(1-7) prevents diabetes-induced cardiovascular dysfunction. *Am J Physiol Heart Circ Physiol* 292(1):H666-672.

Dias-Peixoto M F, Santos R A S, Gomes E R M, Alves M N M, Almeida P W M, Greco L, Rosa M, Fauler B, Michael Bader, Alenina N, Guatimosim S. Molecular Mechanisms Involved in the Angiotensin-(1-7)/Mas Signaling Pathway in Cardiomyocytes. Hypertension. 2008; 52: 542-548

Dhaunsi, G. S., Yousif, M. H., Akhtar, S., Chappell, M. C., Diz, D. I., & Benter, I. F. (2010). Angiotensin-(1-7) prevents diabetes-induced attenuation in PPAR-γ and catalase activities. *European journal of pharmacology*, 638(1), 108-114.

Ebermann L, Spillmann F, Sidiropoulos M, Escher F, Heringer-Walther S, Schultheiss H P, Tschope C, Walther T (2008) The angiotensin-(1-7) receptor agonist AVE0991 is cardioprotective in diabetic rats. *Eur J Pharmacol* 590(1-3):276-280.

Kosugi, T., Heinig, M., Nakayama, T., Matsuo, S., & Nakagawa, T. (2010). eNOS knockout mice with advanced diabetic nephropathy have less benefit from renin-angiotensin blockade than from aldosterone receptor antagonists. *The American journal of pathology*, 176(2), 619-629.

Langeveld, B., A. J. Roks, and R. A. Tio. et al. Rat abdominal aorta stenting: a new and reliable small animal model for in-stent restenosis. J Vasc Res 2004. 41:377-386

Loot A E, Roks A J, Henning R H, Tio R A, Suurmeijer A J, Boomsma F, van Gilst W H (2002) Angiotensin-(1-7) attenuates the development of heart failure after myocardial infarction in rats *Circulation* 105(13):1548-1550.

Marcus, Y., et al., Angiotensin 1-7 as Means to Prevent the Metabolic Syndrome: Lessons From the Fructose-Fed Rat Model. Diabetes, 2013. 62(4): p. 1121-1130.

Pham H, Schwartz B M, Delmore J E, Reed E, Cruickshank S, Drummond L, Rodgers K E, Peterson K J, Dizerega G S. Pharmacodynamic stimulation of thrombogenesis by angiotensin (1-7) in recurrent ovarian cancer patients receiving gemcitabine and platinum-based chemotherapy. Cancer Chemother Pharmacol. 2013 April; 71(4):965-72.

Ribeiro-Oliveira A, Nogueira A I, Pereira R M, Boas W W, Dos Santos R A, Simoes e Silva A C (2008) The renin-angiotensin system and diabetes: an update. *Vasc Health Risk Manag* 4(4):787-803.

Rodgers K E, Oliver J, diZerega G S. Phase I/II dose escalation study of angiotensin 1-7 [A(1-7)] administered before and after chemotherapy in patients with newly diagnosed breast cancer. Cancer Chemother Pharmacol. 2006 May; 57(5):559-68.

Rodgers K E, Xiong S, diZerega GS. Accelerated recovery from irradiation injury by angiotensin peptides. Cancer Chemother Pharmacol. 2002 May; 49(5):403-11.

Santos R A, Simoes e Silva A C, Marie C, Silva D M, Machado R P, de Buhr I, Heringer-Walther S, Pinheiro S V, Lopes M T, Bader M, Mendes E P, Lemos V S, Campagnole-Santos M J, Schultheiss H P, Speth R, Walther T (2003) Angiotensin-(1-7) is an endogenous ligand for the G protein-coupled receptor Mas *Proc Natl Acad Sci USA* 100(14):8258-8263.

Santos, R. A. S., and Ferreira, A. J. (2006). Pharmacological Effects of AVE 0991, a Nonpeptide Angiotensin-(1-7) Receptor Agonist. *Cardiovascular Drug Reviews*, 24(3-4), 239-246.

Santos, S. H. S., Braga, J. F., Mario, É. G., Pôrto, L. C. J., da Glória Rodrigues-Machado, M., Murari, A., & Santos, R. A. S. (2010). Improved lipid and glucose metabolism in transgenic rats with increased circulating angiotensin-(1-7). *Arteriosclerosis, thrombosis, and vascular biology*, 30(5), 953-961.

Singh K, Singh T, Sharma P L (2011) Beneficial effects of angiotensin-(1-7) in diabetic rats with cardiomyopathy. *Ther Adv Cardiovasc Dis* 5(3):159-167.

Steckelings, U. M., Larhed, M., Hallberg, A., Widdop, R. E., Jones, E. S., Wallinder, C., Namsolleck, P., Dahlöf, B., and Unger, T. (2011). Non-peptide AT2-receptor agonists. *Curr Opin Pharmacol*, 11(2), 187-192.

Zhang, T., Li, Z., Dang, H., Chen, R., Liaw, C., Tran, T.-A., Boatman, P. D., Connolly, D. T., and Adams, J. W. (2012). Inhibition of Mas G-protein signaling improves coronary blood flow, reduces myocardial infarct size, and provides long-term cardioprotection. *American Journal of Physiology—Heart and Circulatory Physiology*, 302(1), H299-H311.

What is claimed is:

1. A compound having the general formula 1:

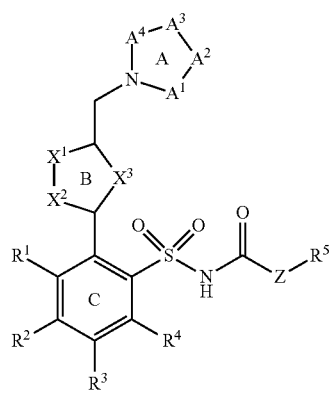

wherein:
ring A is a five-membered or six-membered heteroaryl or heterocyclyl ring containing either a combination of two non-adjacent nitrogen or oxygen atoms, or a combination of three or four nitrogen or oxygen atoms;

ring B is a five-membered or six-membered heteroaryl ring that contains at least one nitrogen atom;

$A^1, A^2, A^3, A^4$ are independently selected from a group consisting of $=N-$, $-C(=O)-$, $-C(R^a)=$, $=C(R^b)-$, $-C(R^c)(R^d)-N(R^e)-$, $-C(R^c)(R^d)-O-$, and $-[C(R^c)(R^d)]_n-$, wherein n is 1 or 2;

$X^1-X^2$ is $-(R^6)C=N-$, $-N=C(R^6)-$, $-N=N-$, $-N=O-$, $-O=N-$, $-N=S-$ or $-S=N-$;

$X^3$ is $-(R^7)C=C(R^8)-$, $-O-$, $-S-$, or $-N(R^9)-$;

Z is $-O-$, $-NH-$ or a bond to $R^5$;

$R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy, or $R^a$ and $R^b$, together with the atoms to which they are attached, form a ring of up to 6 atoms;

$R^c$ and $R^d$ are independently selected from a group consisting of hydrogen, alkyl, aryl, and heteroaryl, or $R^c$ and $R^d$, together with the atoms to which they are attached, form a ring of up to 6 atoms;

$R^e$ is hydrogen, alkyl, aryl, heteroaryl, acyl, alkoxyacyl, aminoacyl, dialkylaminoacyl, or dialkylaminoacyl;

$R^1, R^3, R^4, R^6, R^7$, and $R^8$ are independently selected from a group consisting of hydrogen, alkyl, alkenyl, alkynyl, aryl, heteroaryl, arylmethyl, heteroarylmethyl, fluoro, bromo, iodo, cyano, hydroxy, amino, alkylamino, alkoxy, aryloxy, alkoxyalkyl, and aryloxyalkyl;

$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;

$R^5$ is alkyl, aryl, heteroaryl, hydroxyalkyl, carboxyalkyl, alkoxyalkyl, or aryloxyalkyl; and $R^9$ is hydrogen, alkyl, aryl, heteroaryl, acyl, alkoxyacyl, aminoacyl, dialkylaminoacyl, or dialkylaminoacyl;

or a pharmaceutically acceptable salt thereof.

2. The compound of claim 1, wherein:
ring A is selected from a group consisting of:

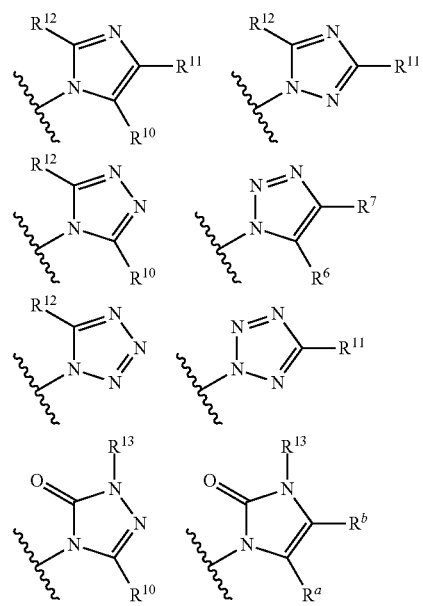

-continued

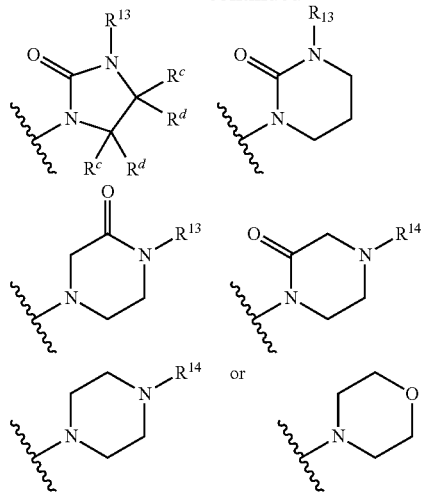

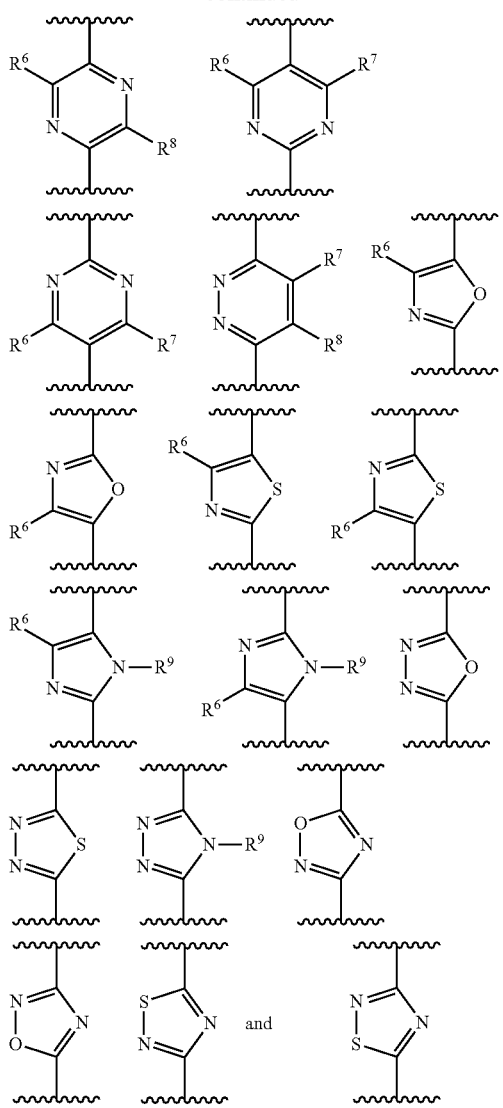

wherein:
R[10] and R[11] are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy, or R[10] and R[11], together with ring A to which they are attached, form:

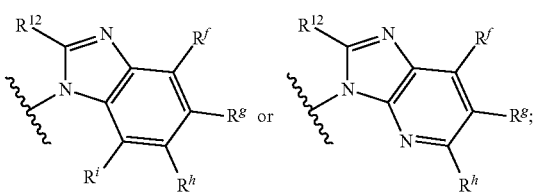

wherein
R[f], R[g], R[h], and R[i], are independently selected from hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, and aryloxyalkyl;

R[12] is hydrogen, alkyl, alkenyl, alkynyl, aryl, heteroaryl, halo, hydroxy, hydroxyalkyl, alkoxyalkyl, alkoxy, aryloxy, or acylamido;

R[13] is hydrogen, alkyl, aryl or heteroaryl;

R[14] is hydrogen, alkyl, aryl, heteroaryl, acyl, alkoxyacyl, aminoacyl, dialkylaminoacyl, or dialkylaminoacyl; and ring B is selected from a group consisting of:

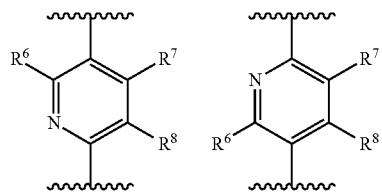

or a pharmaceutically acceptable salt thereof.

3. The compound of claim 2, having a general formula selected from a group consisting of:

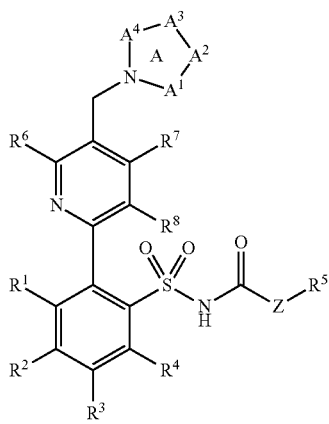

-continued
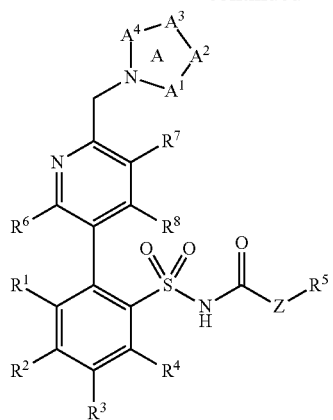
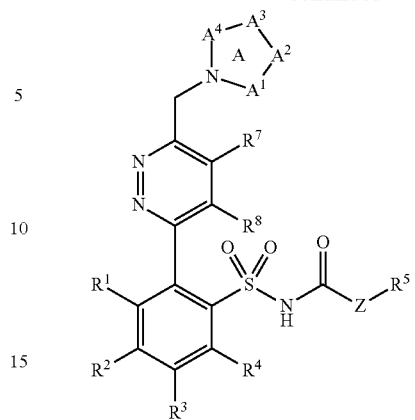
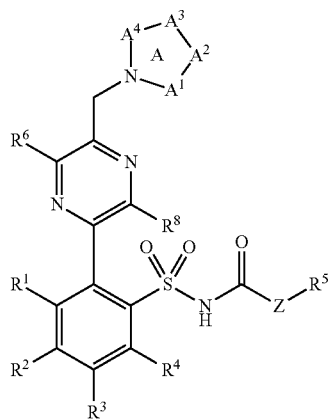
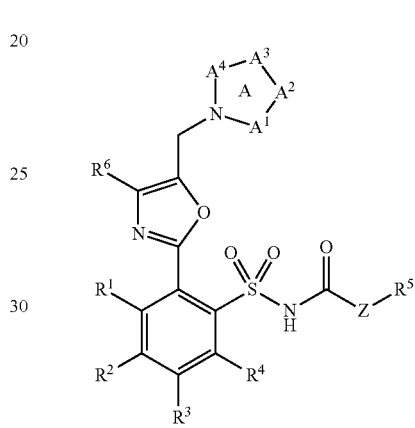
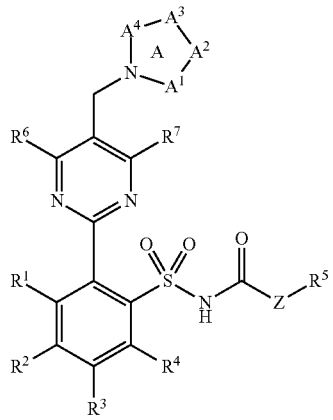
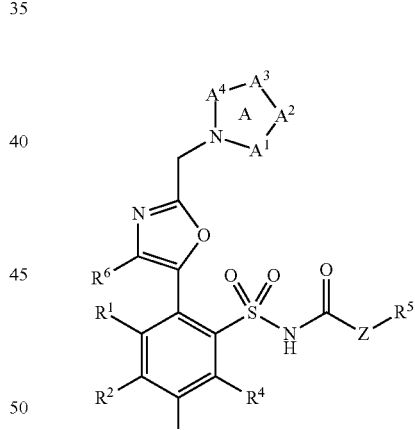
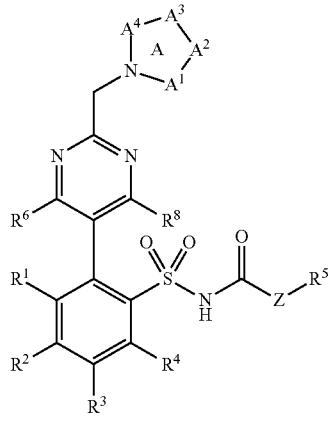
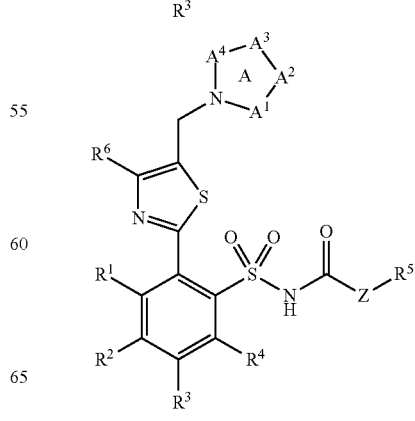

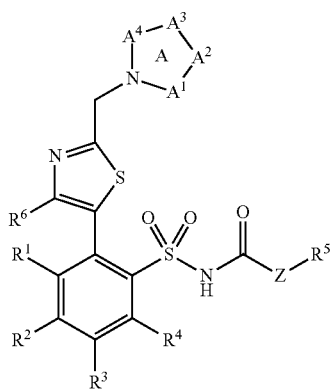
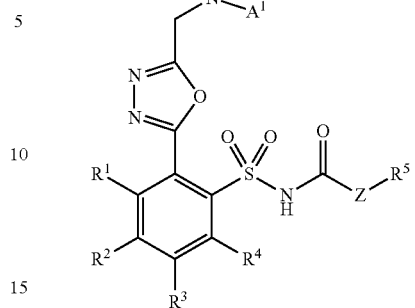
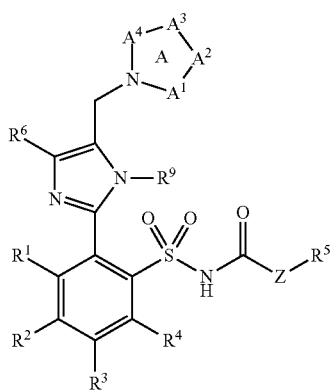
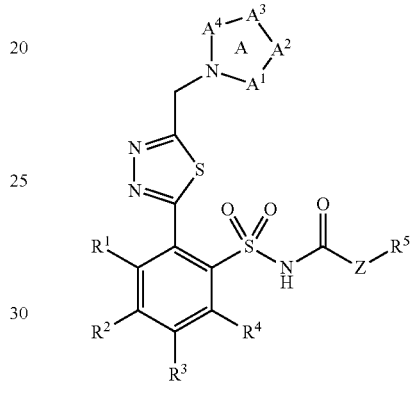
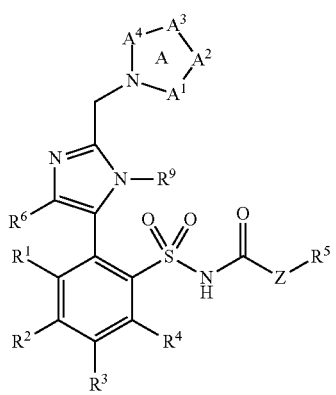
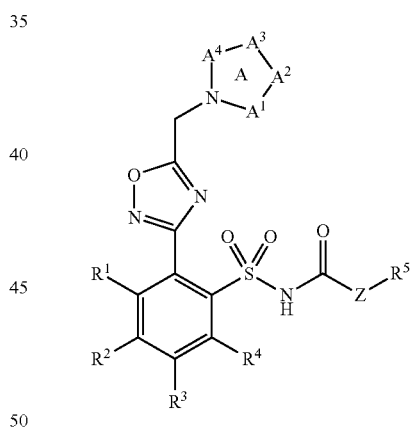
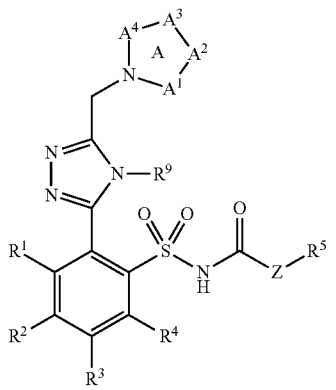
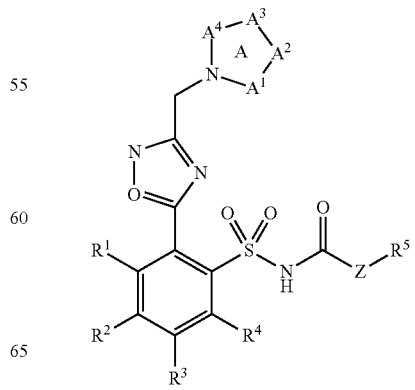

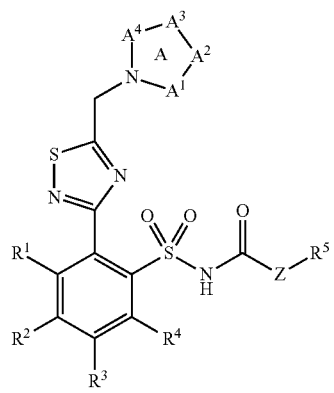
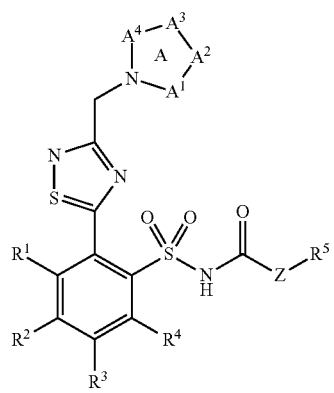
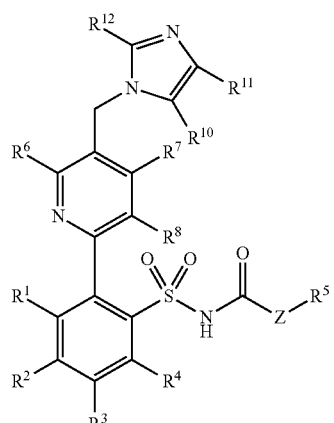
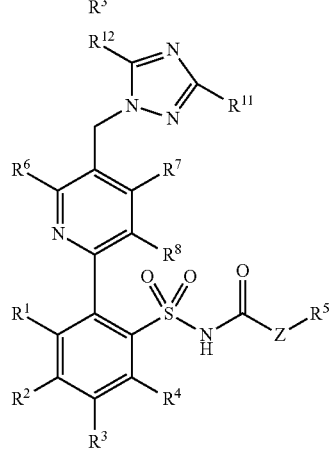
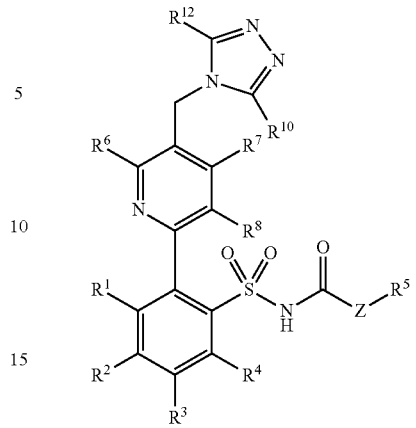
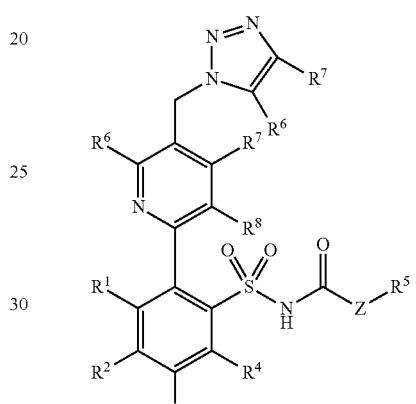
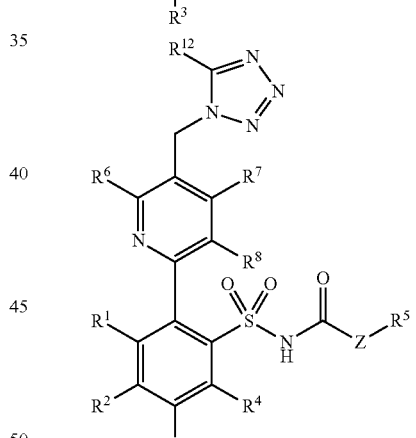
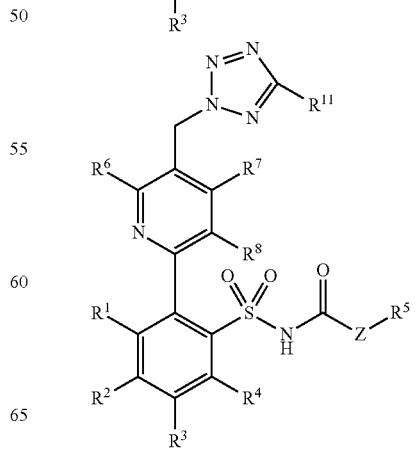

75
-continued
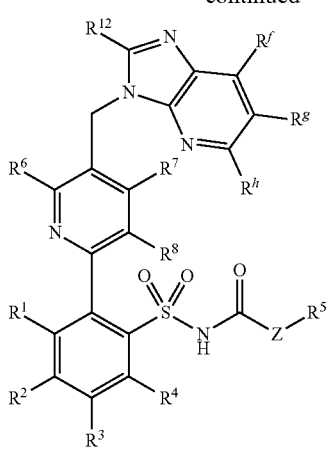
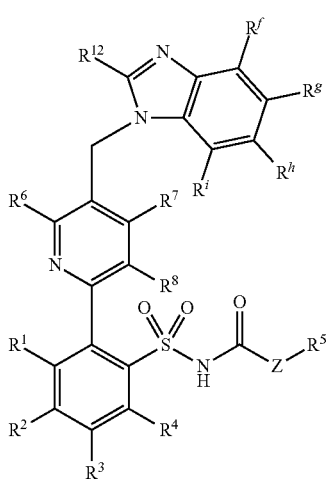
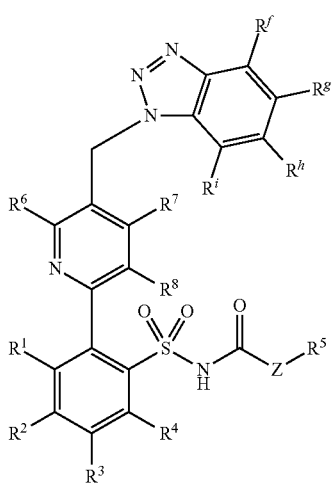
76
-continued
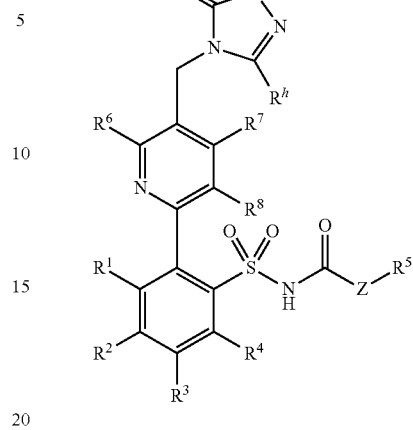
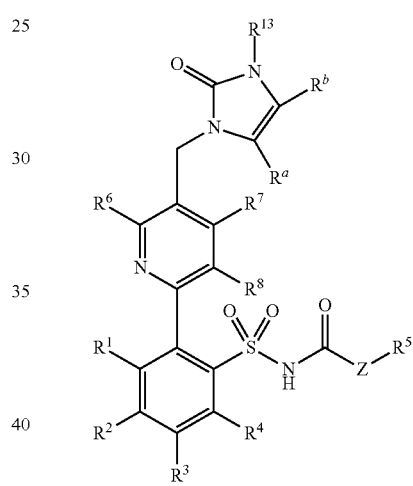
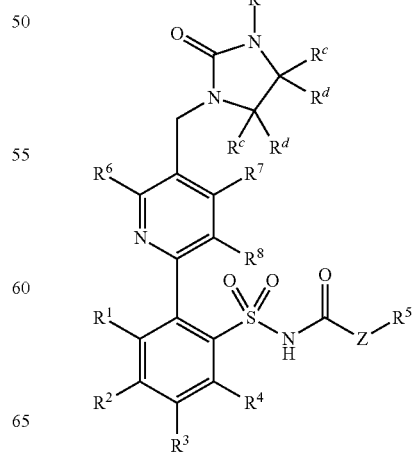

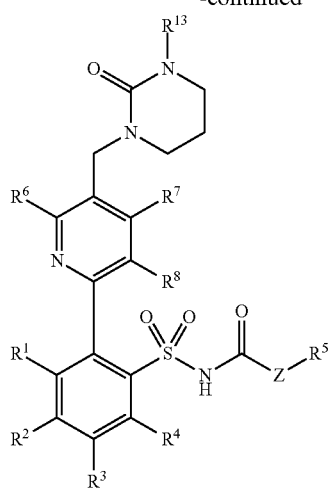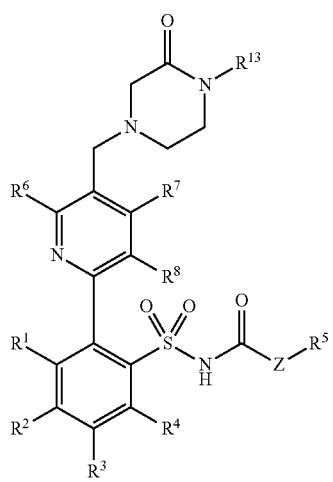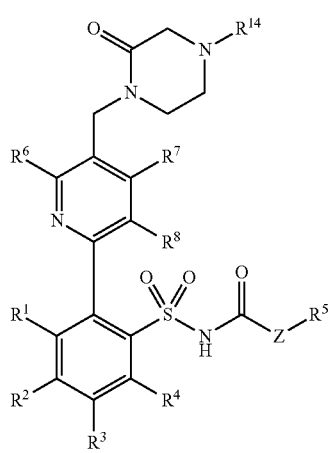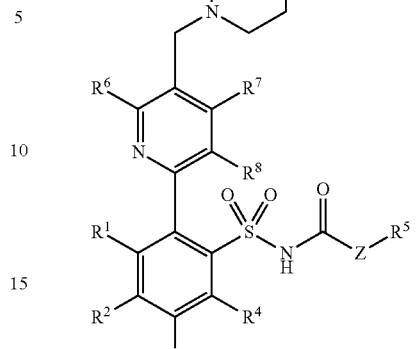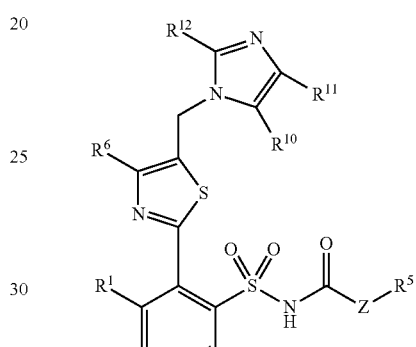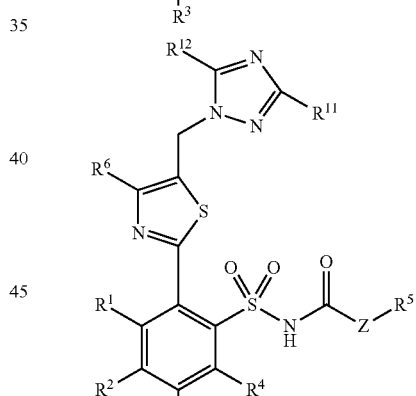

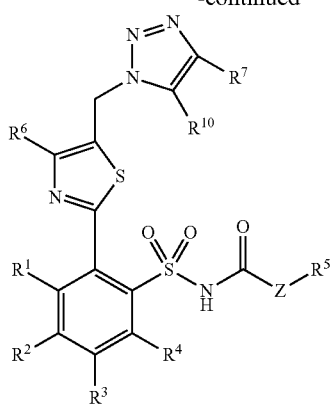
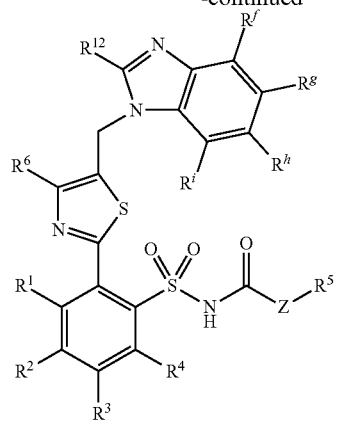
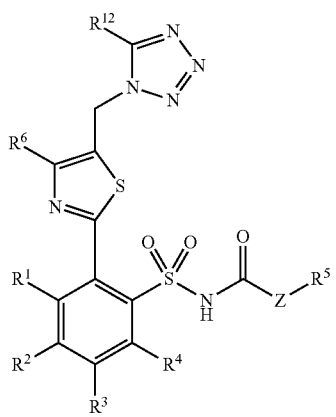
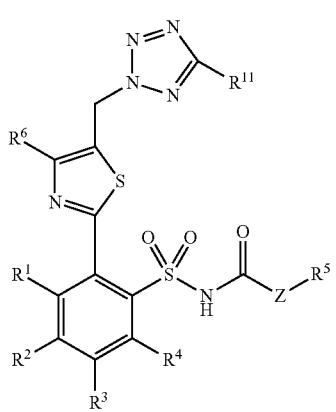
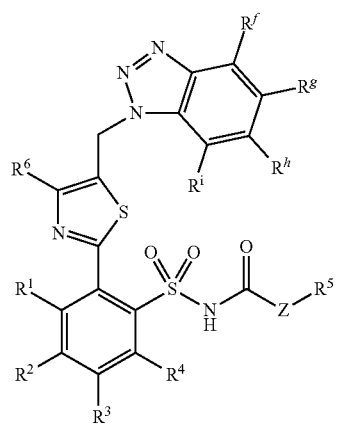
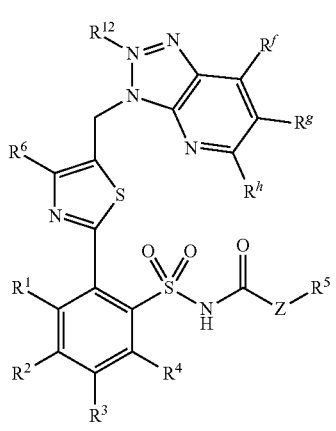
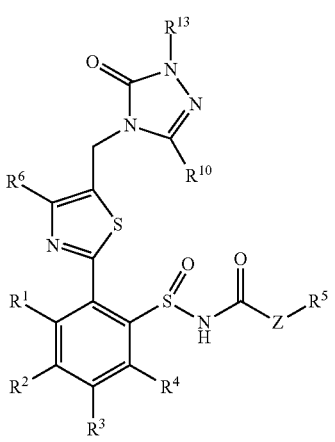

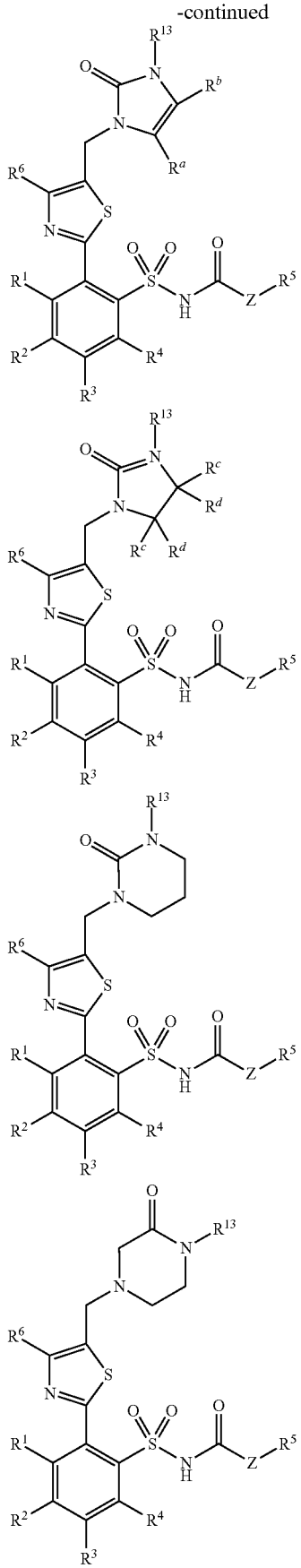
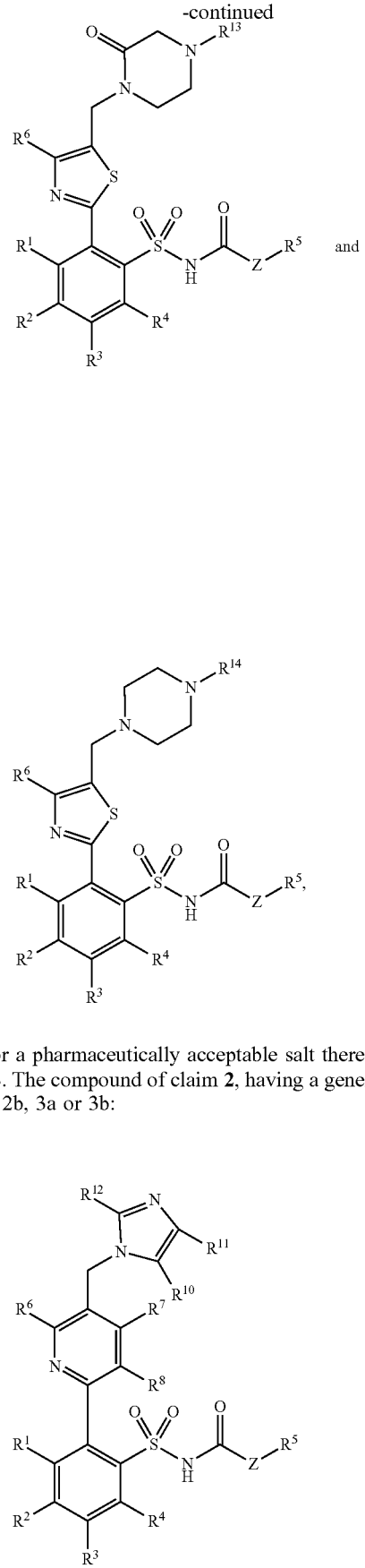
or a pharmaceutically acceptable salt thereof.
4. The compound of claim 2, having a general formula of 2a, 2b, 3a or 3b:
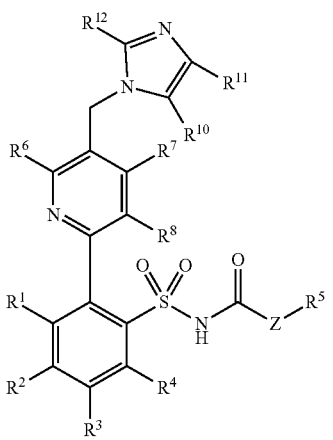
2a 2b 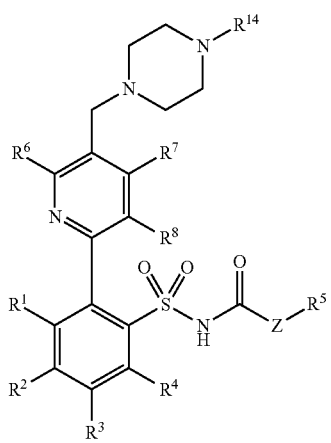
3a 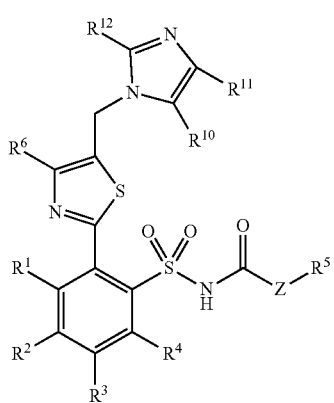
3b 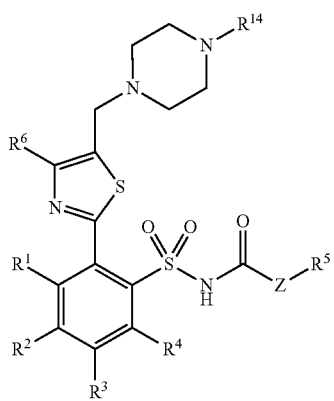
or a pharmaceutically acceptable salt thereof.
5. The compound of claim 2, having the general formula of 4a, 4b, 5a, 5b, 6a or 6b:
4a 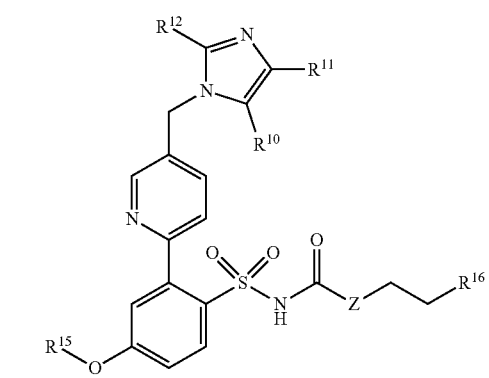
4b 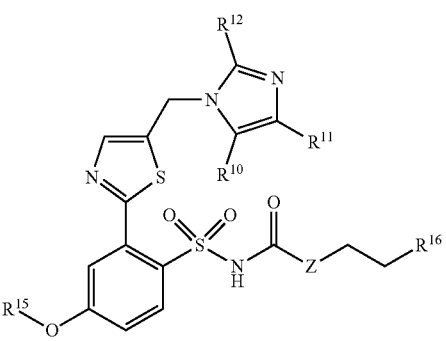
5a 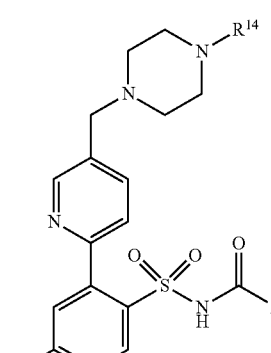
5b 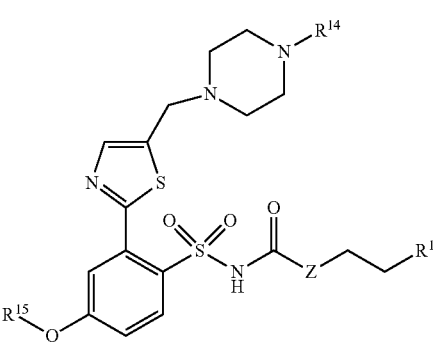

85

-continued

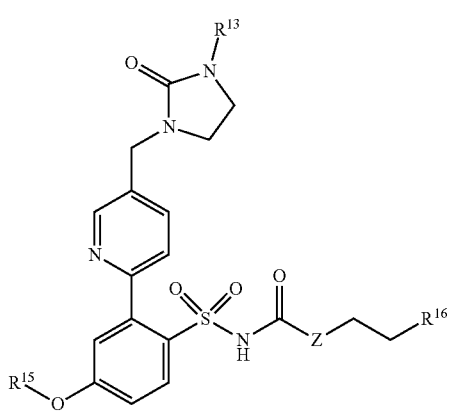

6a

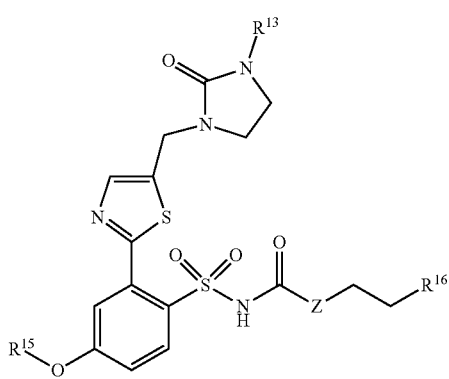

6b wherein
R[15] is alkyl, aryl, heteroaryl, arylmethyl, heteroarylmethyl, trifluoromethyl or pentafluoroethyl; and
R[16] is hydrogen, hydroxy, methoxy, alkoxy, alkyl, alkenyl, alkynyl, aryl, heteroaryl, amino, alkylamino, or dialkylamino;
or a pharmaceutically acceptable salt thereof.

6. The compound of claim 5, wherein R[10], R[11] and R[12] are hydrogen, or R[15] is trifluoromethyl, or R[16] is ethyl, or Z is selected from the group consisting of —O— and —NH—.

7. The compound of claim 2, wherein the compound is:

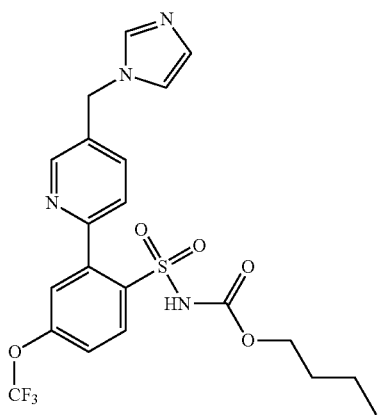 [SMILES: CCCCOC(=O)NS(=O)(=O)c1ccc(OC(F)(F)F)cc1-c1ccc(Cn2ccnc2)cn1]

or a pharmaceutically acceptable salt thereof.

8. The compound of claim 2, wherein the compound is selected from the group consisting of:

86

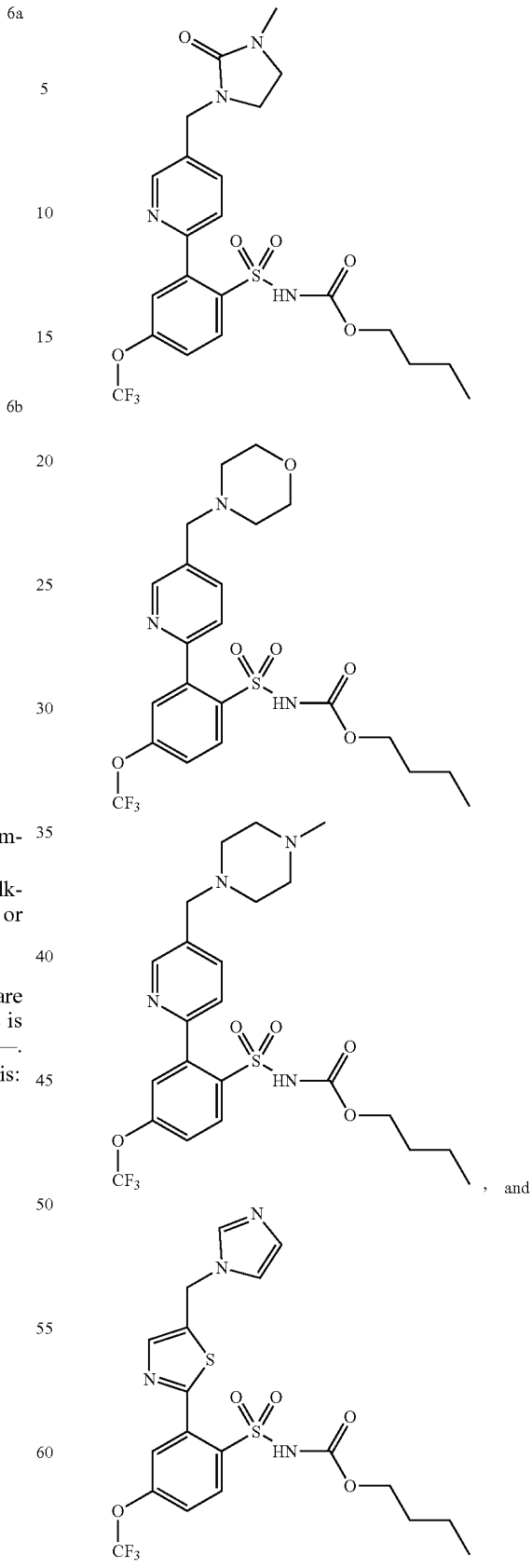

, and or a pharmaceutically acceptable salt thereof.

9. The compound of claim 2, wherein the compound is

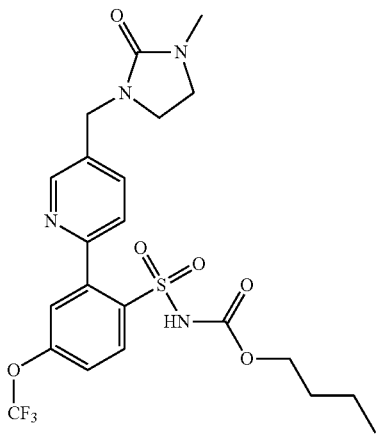 [SMILES: CCCCOC(=O)NS(=O)(=O)c1ccc(OC(F)(F)F)cc1-c1ccc(CN2CCN(C)C2=O)cn1]

or a pharmaceutically acceptable salt thereof.

10. The compound of claim 2, wherein the compound is

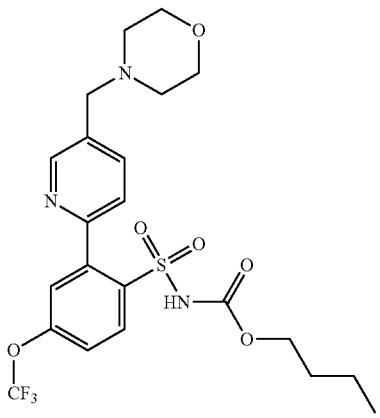 [SMILES: CCCCOC(=O)NS(=O)(=O)c1ccc(OC(F)(F)F)cc1-c1ccc(CN2CCOCC2)cn1]

or a pharmaceutically acceptable salt thereof.

11. The compound of claim 2, wherein the compound is

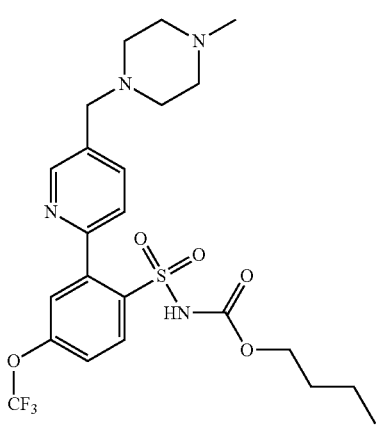 [SMILES: CCCCOC(=O)NS(=O)(=O)c1ccc(OC(F)(F)F)cc1-c1ccc(CN2CCN(C)CC2)cn1]

or a pharmaceutically acceptable salt thereof.

12. The compound of claim 2, wherein the compound is

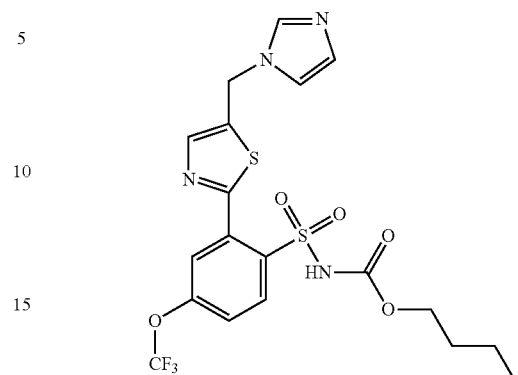

or a pharmaceutically acceptable salt thereof.

13. A pharmaceutical composition comprising a compound according to claim 1, or a pharmaceutically acceptable salt thereof, and a pharmaceutically acceptable carrier.

14. A method for treating hypertension, myelodysplastic syndrome, diabetes, fat accumulation or breast cancer in a patient in need thereof, comprising administering to the patient an effective amount of the compound of claim 1, or a pharmaceutically acceptable salt thereof, to treat the hypertension, myelodysplastic syndrome, diabetes, fat accumulation or breast cancer.

15. The method according to claim 14, wherein the method is for treating hypertension.

16. The method according to claim 14, wherein the method is for treating myelodysplastic syndrome.

17. The method according to claim 14, wherein the method is for treating diabetes mellitus.

18. The method according to claim 14, wherein the method is for treating fat accumulation.

19. The method according to claim 14, wherein the method is for treating breast cancer.

20. The method of claim 14, wherein the compound has general formula of 4a, 4b, 5a, 5b, 6a or 6b:

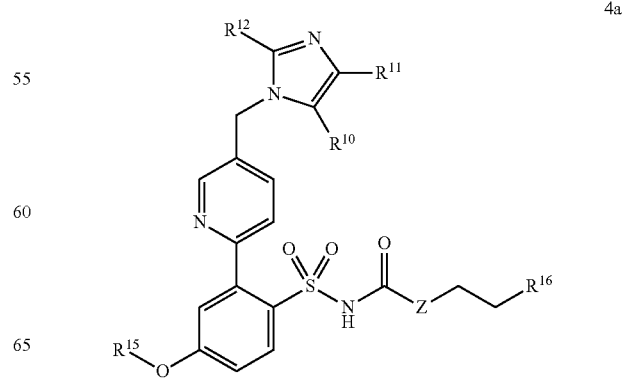

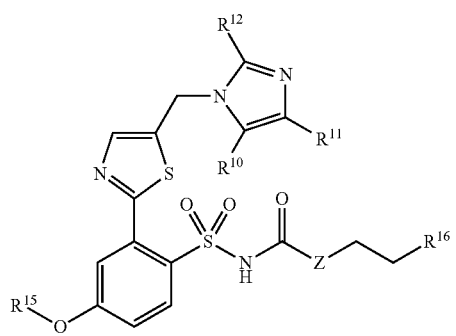
4b

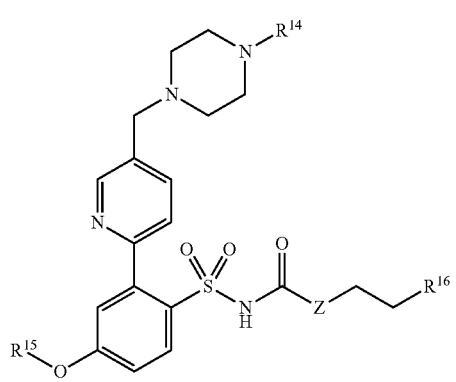
5a

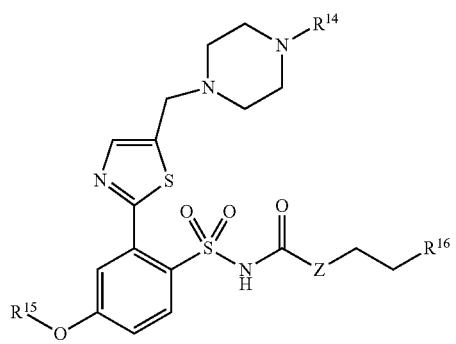
6a

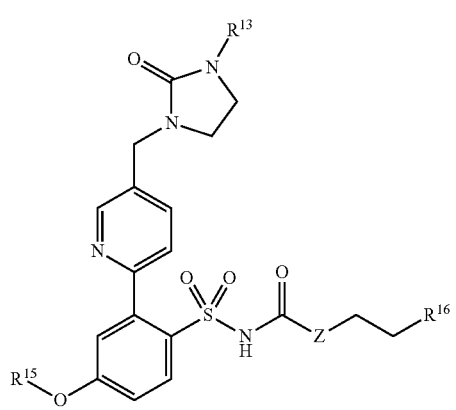

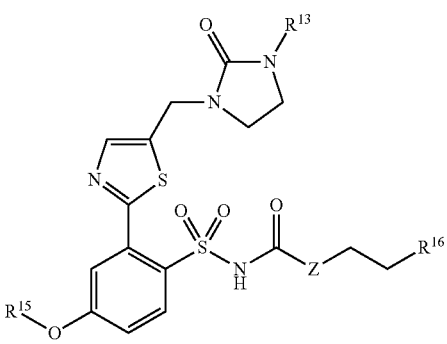
6b wherein
R$^{15}$ is alkyl, aryl, heteroaryl, arylmethyl, heteroarylmethyl, trifluoromethyl or pentafluoroethyl; and R$^{16}$ is hydrogen, hydroxy, methoxy, alkoxy, alkyl, alkenyl, alkynyl, aryl, heteroaryl, amino, alkylamino, or dialkylamino;

or a pharmaceutically acceptable salt thereof.

21. The method of claim 14, wherein the compound is selected from the group consisting of:

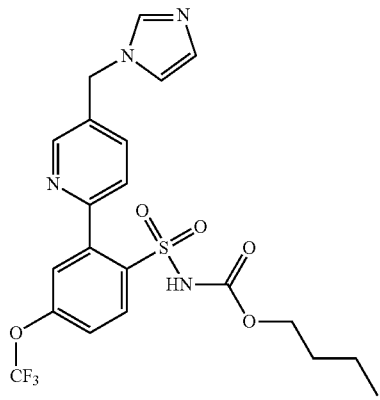

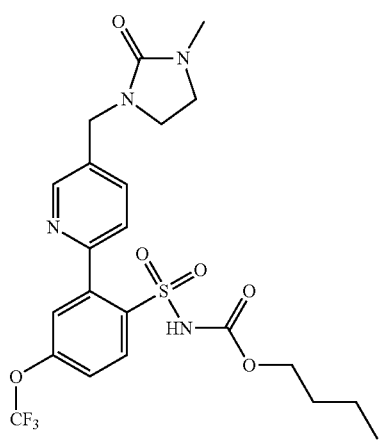

-continued
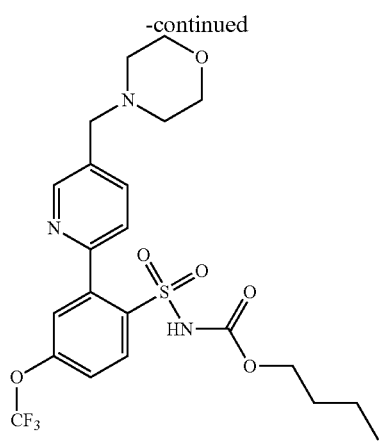
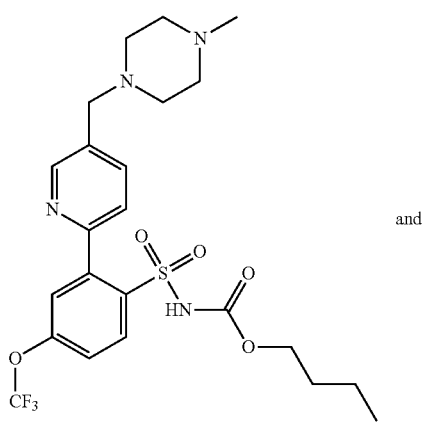
-continued
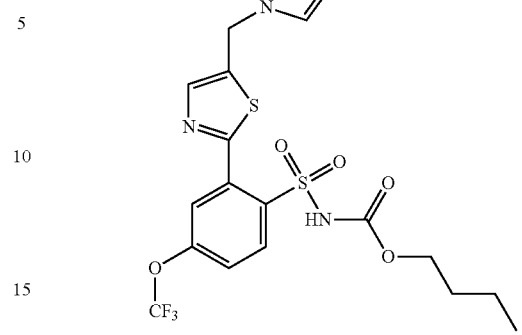
or a pharmaceutically acceptable salt thereof.
22. The method of claim 14, wherein the compound is
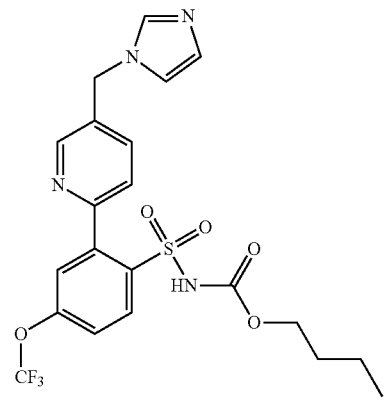
and
* * * * *